US011473143B2

(12) United States Patent
Heron et al.

(10) Patent No.: US 11,473,143 B2
(45) Date of Patent: Oct. 18, 2022

(54) GENE AND MUTATIONS THEREOF ASSOCIATED WITH SEIZURE AND MOVEMENT DISORDERS

(71) Applicants: ITEK VENTURES PTY LTD, Salisbury South (AU); The University of Melbourne, Melbourne (AU); Central Adelaide Local Health Network Incorporated, Adelaide (AU)

(72) Inventors: Sarah Elizabeth Heron, Highbury (AU); Leanne Michelle Dibbens, College Park (AU); Samuel Frank Berkovic, Melbourne (AU); Ingrid Eileen Scheffer, Melbourne (AU); John Charles Mulley, Firle (AU)

(73) Assignees: The University of Melbourne, Victoria (AU); Central Adelaide Local Health Network Incorporated, Adelaide (AU); Itek Ventures PTY Ltd (University of South Australia), Salisbury South (AU)

( * ) Notice: Subject to any disclaimer, the term of this patent is extended or adjusted under 35 U.S.C. 154(b) by 438 days.

(21) Appl. No.: 15/663,629

(22) Filed: Jul. 28, 2017

(65) Prior Publication Data

US 2018/0030536 A1 Feb. 1, 2018

Related U.S. Application Data

(63) Continuation of application No. 14/354,461, filed as application No. PCT/AU2012/001321 on Oct. 29, 2012, now Pat. No. 9,752,193.

(30) Foreign Application Priority Data

Oct. 28, 2011 (AU) .............................. 2011904493
Jan. 18, 2012 (AU) .............................. 2012900190

(51) Int. Cl.
| | | |
|---|---|---|
| *C12Q 1/68* | (2018.01) | |
| *C12P 19/34* | (2006.01) | |
| *C12Q 1/6883* | (2018.01) | |
| *C07K 14/705* | (2006.01) | |
| *C07K 14/47* | (2006.01) | |
| *C07K 16/18* | (2006.01) | |
| *G01N 27/447* | (2006.01) | |

(52) U.S. Cl.
CPC ............ *C12Q 1/6883* (2013.01); *C07K 14/47* (2013.01); *C07K 14/705* (2013.01); *C07K 16/18* (2013.01); *G01N 27/447* (2013.01); *C12Q 2600/118* (2013.01); *C12Q 2600/136* (2013.01); *C12Q 2600/156* (2013.01)

(58) Field of Classification Search
CPC ............ C12Q 1/6883; C12Q 2600/118; C12Q 2600/156
See application file for complete search history.

(56) References Cited

U.S. PATENT DOCUMENTS

| 5,331,573 | A | 7/1994 | Balaji et al. | |
|---|---|---|---|---|
| 5,579,250 | A | 11/1996 | Balaji et al. | |
| 9,752,193 | B2 | 9/2017 | Heron et al. | |
| 2001/0053519 | A1* | 12/2001 | Fodor | B01J 19/0046 435/6.11 |
| 2004/0214272 | A1* | 10/2004 | La Rosa | C07H 21/04 435/69.1 |
| 2018/0030536 | A1 | 2/2018 | Heron et al. | |

FOREIGN PATENT DOCUMENTS

| CN | 102296075 A | 12/2011 |
|---|---|---|
| EP | 0 235 726 | 5/1993 |
| WO | WO 84/03564 | 9/1984 |
| WO | WO 89/11548 | 11/1989 |

(Continued)

OTHER PUBLICATIONS

New England Biolabs (NEB) catalog (1998/1999), pp. 121 and 284 (Year: 1998).*
Rothstein et al. (1994) PNAS USA 91:4155-4159 (Year: 1994).*
GenBank Locus: BM122253 "L0507E05-3 NIA Mouse Newborn Heart cDNA Library Mus musculus cDNA clone L0507E05 3', mRNA sequence" Feb. 1, 2002. (Year: 2002).*
Hessner, M.J. et al. "Three color cDNA microarrays: quantitative assessment through the use of Fluorescein-labeled probes" Nucleic Acids Research, 2003, vol. 31, No. 4 (Year: 2003).*
Yadetie, F. et al. "Miniaturized fluorescent RNA dot blot method for rapid quantitation of gene expression" BMC Biotechnology 2004, 4. (Year: 2004).*

(Continued)

*Primary Examiner* — Stephen T Kapushoc
(74) *Attorney, Agent, or Firm* — Foley & Lardner LLP

(57) ABSTRACT

The present invention relates to the proline rich transmembrane protein 2 (PRRT2) gene, and the identification of mutations and variations in PRRT2 that give rise to seizure and movement disorders. Accordingly, the present invention provides methods for the diagnosis or prognosis of such disorders by identifying alterations in the PRRT2 gene. Identification of alterations in the PRRT2 gene also enables the identification of subjects with an increased likelihood of having an offspring predisposed to such disorders. The present invention also provides an isolated nucleic acid molecule comprising an alteration in the PRRT2 gene, wherein said alteration produces a seizure and/or movement disorder phenotype. Also provided is an isolated PRRT2 polypeptide that comprises an alteration which produces a seizure and/or movement disorder phenotype. Furthermore, the present invention provides kit for diagnosing or prognosing a seizure and/or movement disorder in a subject, or for identifying a subject with an increased likelihood of having an offspring predisposed to a seizure and/or movement disorder, wherein the kit includes one or more components for testing for the presence of an alteration in the PRRT2 gene in the subject.

4 Claims, 11 Drawing Sheets
Specification includes a Sequence Listing.

(56) References Cited

FOREIGN PATENT DOCUMENTS

| WO | WO 2009/004576 A1 | 1/2009 |
|---|---|---|
| WO | WO2013/059884 A1 | 5/2013 |

OTHER PUBLICATIONS

Office Action issued in co-pending Canadian Patent Application No. 2,852,631, dated Jun. 27, 2019.
*Homo sapiens* mRNAfor hypothetical protein LOC112476 variant,clone:FCC131H12, Accession No. GenBank:AK225785.1, Jul. 22, 2006, [online] [retrieved from internet], [Search date:Jun. 25, 2018], <https://www.ncbi.nlm.nih.gov/nuccore/AK225785.1.
Notice of Reasons for Refusal issued in co-pending Japanese Patent Application No. 2014-537429, dated Jul. 5, 2018.
Alderborn et al., "Determination of Single-Nucleotide Polymorphisms by Real-time Pyrophosphate DNA Sequencing," Genome, pp. 1249-1265 (2000).
Anderson, et al., "Reliable Gene Expression Measurements from Fine Needle Aspirates of Pancreatic Tumors," *Journ. of Mol. Diag.*, vol. 12, No. 5, pp. 566-575 (2010).
Chen et al., "Exome sequencing identifies truncating mutations in PRRT2 that cause paroxysmal kinesigenic dyskinesia," vol. 43, No. 12, *Nature Genetics*, pp. 1252-1255 (2011).
Cole, S.P. et al., "Human monoclonal antibodies," (1984) *Mol. Cell Biol.* 62:109-120.
Cole, R.J. et al., "Generation of human monoclonal antibodies reactive with cellular antig," (1983) *Proc. Natl. Acad. Sci. USA* 80:2026-2030.
Finkelstein et al., "Use of denaturing gradient gel electrophoresis for detection of mutation and prospective diagnosis in late onset ornithine transcarbamylase deficiency," *Genomics*, pp. 167-172 (1990) [Abstract].
Hage, et al., "Immunoassays," *Anal. Chem.*, 15, vol. 71, No. 12, pp. 294R-304R (1999).
Heron et al., "PRRT2 Mutations Cause Benign Familial Infantile Epilepsy and Infantile Convulsions with Choreoathetosis Syndrome," *The Amer. Journ. of Human Genetics*, vol. 90, pp. 152-160 (2012).
Huse, W.D. et al., "Generation of a Large Combinatorial Library of the Immunoglobulin Repertoire in Phage Lambda," (1989) *Science* 246:1275-1281.
Kinszler et al., "Identification of a Gene Located at Chromosome 5q21 that is Mutated in Colorectal Cancers," *Science*, vol. 251, pp. 1366-1370 (1991).
Kohler, G. et al., "Continuous Cultures of Fused Cells Secreting Antibody of Predefined Specificity," (1975) *Nature* 256:495-497.
Kozbor, D. et al., "Specific Immunoglobulin Production and Enhanced Tumorigenicity Following Ascites Growth of Human Hybridomas," *J. Immunol. Methods* 81:31-42 (1985).
Kunath et al., "Transgenic RNA interference in ES cell-derived embryos recapitulates a genetic null phenotype," vol. 21, No. 5, pp. 559-561 (2003) [Abstract].
Lee et al., "Mutations in the Gene PRRT2 Cause Paroxysmal Kinesigenic Dyskinesia with Infantile Convulsions," *Cell Reports*, vol. 1, pp. 2-12 (2012).
Li et al.,"Targeted genomic sequencing identifies PRRT2 mutations as a cuse of paroxysmal kinesigenic choreoathetosis," *J. Med. Genet.*, vol. 49, No. 2, pp. 76-78 (2012).
Lipinski et al., "Experimental and computational approaches to estimate solubility and permeability in drug discovery and development settings," *Adv. Drug. Deliv. Rev.*, vol. 46, No. 1-3, pp. 3-26 (2001).
Liu et al., "Mutations in PRRT2 result in paroxysmal dyskinesias with marked variability in clinical expression," *J. Med. Genet.*, vol. 49, No. 2, pp. 79-82 (2012).
Maxam et al., "A new method for sequencing DNA," *Proc. Natl. Acad, Sci.,*, vol. 74, No. 2, pp. 560-564 (1977).
Modrich, "Mechanisms and Biological Effects of Mismatch Repair," *Ann. Rev. Genet.*, vol. 25, pp. 229-253 (1991).
Orita et al., "Detection of polymorphisms of human DNA by gel electrophoresis as single-strand confirmation polymorphisms," *Proc. Natl. Acad. Sc.i*, vol. 86, pp. 2766-2770 (1989).
Orlandi, R. et al. "Cloning immunoglobulin variable domains for expression by the polymerase chain reaction," Proc. Natl. Acad. Sci. USA (1989) 86:3833-3837.
Palk et al., "A multigene Assay to Predict Recurrence of Tamoxifen-Treated, Node-Negative Breast Cancer," *NEJM* 351(27), pp. 2817-2826 (2004).
Pirogova et al., "Advances in methods for therapeutic peptide discovery, design and development," vol. 12, No. 8, pp. 1117-1127 (2011).
Rickert et al., "B lymphocyte-specific, Cre-mediated mutagenesis in mice," *Nucleic Acids Research*, vol. 25, No. 6, pp. 1317-1318 (1997).
Saiki et al., "Analysis of enzymatically amplified-globin and HLA-DQ DNA with allele-specific oligonucleotide probes," *Nature*, vol. 24, pp. 163-166 (1986) [Abstract].
Sanger et al., "DNA sequencing with chain-terminating inhibitors," *Proc. Natl. Acad. Sci.*, vol. 74, No. 12, pp. 5463-5467 (1977).
Schwenk et al., "A cre-transgenic mouse strain for the ubiquitous deletion of loxP-flanked gene segments including deletion in germ cells," *Nucleic Acids Researchi*, vol. 23, No. 24, pp. 5080-5081 (1995).
Sheffield et al., "Attachment of a 40-base-pair G+C-rich (GC-clamp) to genomic DNA fragments by the polymerase chain reaction results in improved detection of single-base changes," *Proc. Natl. Acad. Sci.*, vol. 86, pp. 232-236 (1989).
Strom, et al., "Technical validation of a multiplex platform to detect thirty mutations in eight genetic diseases prevalent in individuals of Ashkenazi Jewish desent," Genetics, vol. 7, No. 9, pp. 633-639 (2005).
Wang et al., "Identification of PRRT2 as the causative gene of paroxysmal kinesigenic dyskinesias," *Brain*, vol. 134, No. 12, pp. 3493-3501 (2011).
Wartell et al., "Detecting base pair substitutions in DNA fragments by temperature-gradient gel electrophoresis," *Nucl. Acids Res.*, vol. 18, No. 9, pp. 2699-2705 (1990).
Weber et al., "Genetics of Paroxysmal Dyskinesias," vol. 9, No. 3, pp. 206-211 (2009).
Winter, G. et al. "Review Article—Man-made antibodies," Nature (1991) 349:293-299.
International Preliminary Report on Patentability issued in related International Patent Application No. PCT/AU2012/001321, dated May 8, 2014.
International Search Report issued in related International Patent Application No. PCT/AU2012/001321, dated Jan. 14, 2013.
Ghebranious , et al., "A novel microdeletion at 16p11.2 harbors candidate genes for aortic valve development, seizure disorder, and mild mental retardation," *American Journal of Medical Genetics Part A*. 143A: 1462-1471 (2007).
Notice of Reasons for Refusal issued in related Japanese Patent Application No. 2014-537429, dated Nov. 7, 2016.
Bedoyan, JK et al., 2010. Duplication 16p11.2 in a child with infantile seizure disorder., Am J Med Genet Part A 152A; 1567-1574.
Juppner H., Bone vol. 17, No. 2, Supplement, Aug. 1995: 39S-42S.
Pennis, Science: Sep. 18, 1998; 281, 5384; pp. 1787-1789.
Liu, et al., Journal of Investigative Dermatology (2011), vol. 131, pp. 1570-1572.
Tsao, et al., Neuropsychiatric Disease and Treatment 2009: 5, pp. 289-299.
GenBank Locus NM_145239 (Aug. 15, 2011), from http://www.ncbi.nlm..nih.gov, pp. 1-4.
GenBank SNP linked to Gene (geneID: 112476) via Contig Annoation, printed from http://www.ncbi.nlm.nih.gov, Nov. 2, 2015, pp. 1-17.
Hegele, et al., Arterioscler Thromb Vasc. Biol., 2002; 22: 1058-1061.

(56) References Cited

OTHER PUBLICATIONS

Submitted SNP(ss) Report in Submission Format, NCBI Assay Id(ss#); ss136656564, May 11, 2009, printed from www.ncbi.nih.gov, pp. 1-2.
Tyagi, et a., Nature Biotechnology, (Mar. 1996) vol. 14, pp. 303-308.

* cited by examiner

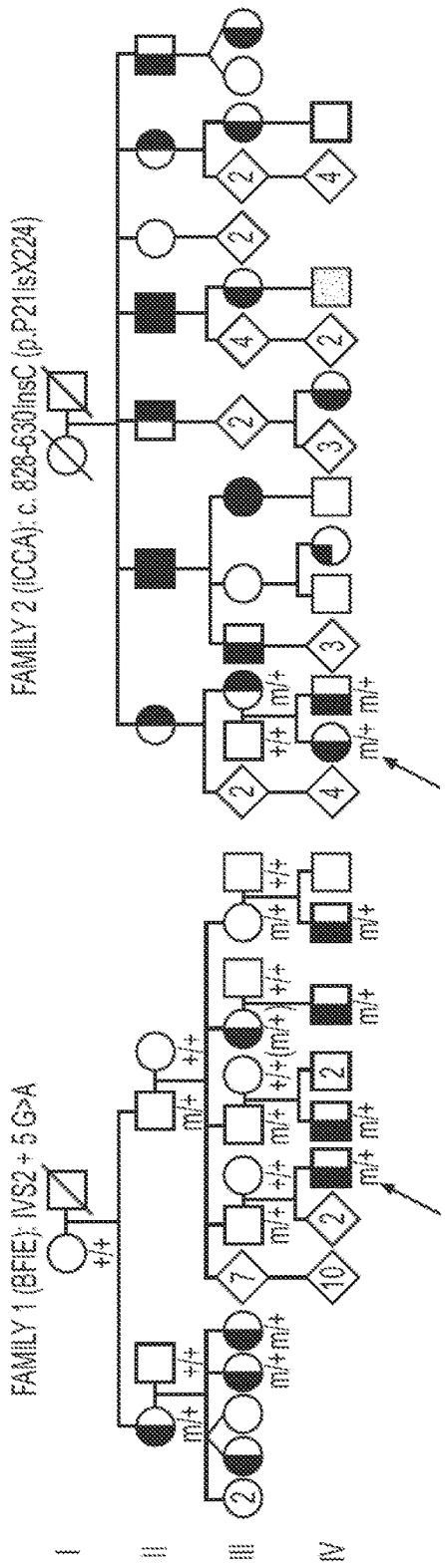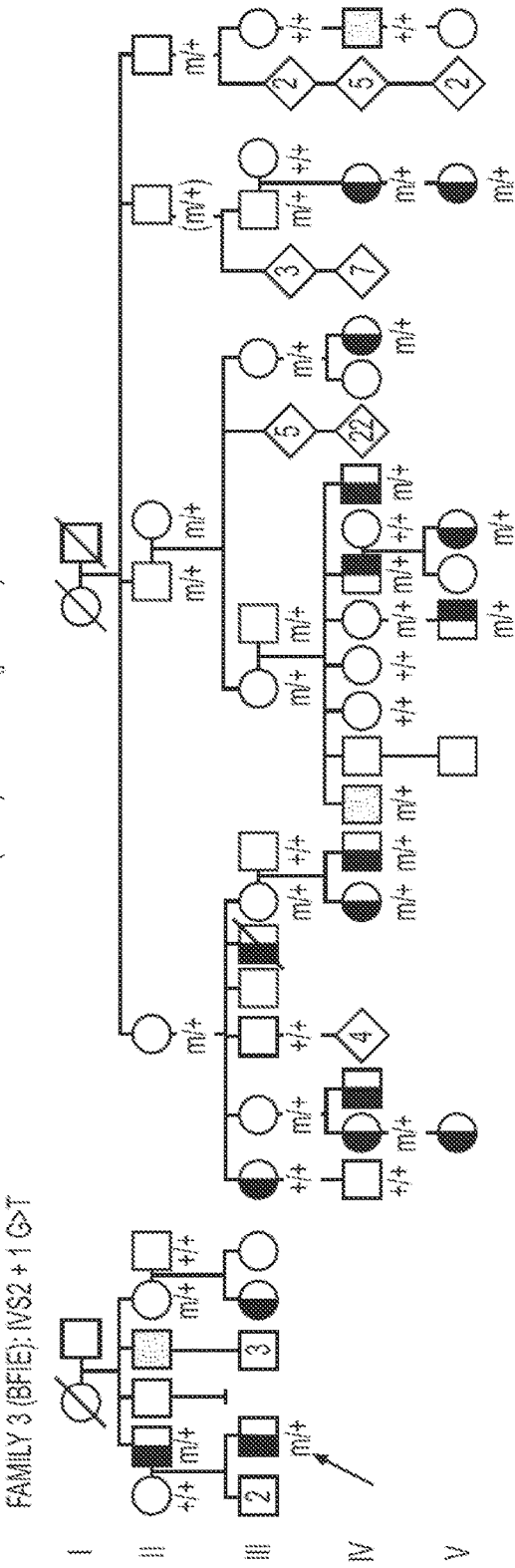
FIG. 1

FIGURE 3

```
cgggaggggccggggacttaagaaggaggcgtctctcctggaggcgcgcgtgagaaggggcagggaggggcgcgagtg
gtccccgggccggttgcctggGTAACGCGTGGCTCCCTTGGGCTGGCGGGAGGGGCCGGAGGCTCGCGAGGGGCGGGGG
CGGCGACGGCGGCGGAGCGTAGGGGAGGGGACCGGAGAGGAGGGGATGAGCACACGGGAGACGGACAAGAGGGAGACCCG    Exon 1
CCGCCTCCCTCCCTCCCTAGCTGACTTGCTCCCTCCCGGGCTGCGGCTGCTGCAAAAGCCAGCAGCGGCAGCGGGAGCT
GTCCGGAGGCCGGCGTCGAGgtgagacccgggcagactgaggctgcgggtaggagtggaccgaccgacggctgacgccg
ggcggactgcacgggaatgcgggtgtctggagggctggtggtggtgctgggcgggctgaaccatcgggaggaggcgcca
gcccaccgaaggcgagggaagccccgggagaggggctgacaggggatcgaaggagataaccaggtcccccagaaagggg
cgggagcgtcctcgccctaaacgcgcagcaagaaaacccgcaccgcctggagcccagggaggaggggaggatgcagag
ggagtggaatgcgaatgtcgggtcctctgcccagtcggcctgtcggagtgctatttgcacagctcgttgattttggggt
gctgggatctgagagtctggatcttgttggatggaccccagggagagaccctggagaaggtcctgtttacaaaagggtta
atcttcccagggctctccaagcagaagactttgagtagagcactcctccgcagggatgtcccaccctaaggcaaagg
aaaccccaactttcttcctctccctagaggcagtgcaaggctggccctgagacaggaatgtggcccaattgggcctgc
agtgctgagcgcctcttccctcctcaccccaagcctatctcctcctcttccagGTTTGCCGCTGTCTCTGCTATTCC
ATCCTCCCCATAGGGCTCTCTCCCCTCTCCCATCTCAAGATGGCAGCCAGCAGCTCTGAGATCTCTGAGATGAAGGGG
GTTGAGGAGAGTCCCAAGGTTCCAGGCGAAGGGCCTGGCCATTCTGAAGCTGAAACTGGCCCTCCCCAGGTCCTAGCAG
GGGTACCAGACCAGCCAGAGGCCCCGCAGCCAGGTCCAAACACCACTGCGGCCCCTGTGGACTCAGGGCCCAAGGCTGG
GCTGGCTCCAGAAACCACAGAGACCCCGGCTGGGGCCTCAGAAACAGCCCAGGCCACAGACCTCAGCTTAAGCCCAGGA
GGGGAATCAAAGGCCAACTGCAGCCCCGAAGACCCATGCCAAGAAACAGTGTCCAAACCAGAAGTGAGCAAAGAGGCCA    Exon 2
CTGCAGACCAGGGGTCCAGGCTGGAGTCTGCAGCCCCACCTGAACCAGCCCCAGAGCCTGCTCCCCAACCAGACCCCCG
GCCAGATTCCCAGCCTACCCCCAAGCCAGCCCTTCAACCAGAGCTCCCTACCCAGGAGGACCCCACCCCTGAGATTCTG
TCTGAGAGTGTAGGGGAAAAGCAAGAGAATGGGGCAGTGGTGCCCCTGCAGGCTGGTGATGGGGAAGAGGGCCCAGCCC
CTGAGCCTCACTCACCACCCTCAAAAAAAATCCCCCCCAGCCAATGGGGCCCCCCCCCGAGTGCTGCAGCAGCTGGTTGA
GGAGGATCGAATGAGAAGGGCACACAGTGGGCATCCAGGATCTCCCCGAGGTAGCCTGAGCCGCCACCCCAGCTCCCAG
CTGGCAGGTCCTGGGGTGGAGGGGGGTGAAGGCACCCAGAAACCTCGGGACTACATCATCCTTGCCATCCTGTCCTGCT
TCTGCCCCATGTGGCCTGTCAACATCGTGGCCTTCGCTTATGCTGTCATGgtgagcccatgggaccctagcccaggcc
tgctgtggctcccagcttcccgccagcgctgcaatagagcctctggagtaatcatgccttccttccctctcctctctg
catggatcccacctcccaattccagggcctttgtttgcctctccctaggacctaaccctctgagccaccactgccctg
cccctttgggtgggagggatatggaaacacgtgtcacacagcctcgctgacctgtgccctcctccccctgcccttcac
tcctcctcctccttacccgccatctatggggctggctctctctcttctggatgacttttccacctgatcccttctg
ggctggcttctcctgacccggctatgtgcctccaccctcgccctaaccccagTCCCGGAACAGCCTGCAGCAGGGGG    Exon 3
ACGTGGACGGGGCCCAGCGTCTGGGCCGGGTAGCCAAGCTCTTAAGCATCGTGGCGCTGGTGGGGGGAGTCCTCATCAT
CATCGCCTCCTGCGTCATCAACTTAGGCGgtgagtggggcttgggacaggcaggggaggaatggaagggttggcaagg
gcagctttactaaccctgccctgctctctcctgtctgtcctccttacctctcctttgtctctccttgtctcccctc
cccccgtctgtccttccctctcctctcccacagTGTATAAGTGAGGGGCTCTGCCCCGCATCCCAAGACTTTTCTTCCT
GTTGGGAGCTGCCTTGGGCCCATCCCTCCCCTGGGGGGAGCCCAACTGATGGCCCTGGCCCCCACCCCTAAGGACCAAG
GGAGCCTGAGCGGCCTTGTTTACAGCTTCTGTCCTGCTCCTGCATCTTGCCAGGCTCCTCTGCCAACTGTAGGCCTGCC
TCATCCCTGCACTGGTTCCAACCTCCCTGCACTAATGCCTGCATCCCCTCCGGCCTCTTGGCCCCCTATCCCTGCACTT
CTGGAAACCTCCCTGCACTCTGGAAACCTCCCTGAACACCTCCCCAACTCTGCGCTCTCCAGCCTCCCTGCATCTCTCCT
GGCCTCCCTGCACTTCTTCCAGCCCCCCAAATTCTCTGGACCTCCACCCTGCCGCCTCCTCCCAACTTTCATTGTCTT
GGCATCTCTCAACCCTCAGTCCTCTCTTCCTTCCCTTCTTTATCATCTCCCCTTTCCTCTCCACGTCCCGCCCCCTTCC
TCTTCCTGCCTCCTCATCTCCCTTAAGCATCCTCTTCTCCAACCTCCCGTCACCGTTTACTCTGCAAAATTGACAGCAC
TTAGACGAGGCTTGGGGGCAGGGAGCAGTGTTGGGAGAGGGCTCCCCAACCCCAGGCTCGGACTGTTCTCTGCTGGGAC    Exon 4
CACCCAGGGTCGGACACCCAAGGGTGCCTGGCAGGTCGCAGAGTTGGCAAGCCGGGCCTCGTATGGGACTCGGGTGAG
GGTGGCGAGTACTGGTTCCGAACGCACGCAGGGGAGAAGGGAGGGACGCGGCGCTGACCCTTCCAGGTCAGCTGGAGTT
GACCCGCCCACCTGGGCTTTTCAACCCCAGTCCGCGAGTTTCTTTCTTGAAGGTGTGGGGGCTAGATTCATTCACGTGC
TTCGTAATGAAATAATCCAAAAAATAGGACCAAAGCGCCCACTGGCAGGAGCGAGGGCGGGGCGCCGCGCTCTATAATT
ATTTTCTAAGATGATGGGGAGGTTTGTTGCACGCGACAGCCCGCTGAGGAGGCGGGGACCGAGCTACAACGCGGTTCG
GATTTGGCGGGGGTTTTTTTCCTTAAAAAAAAAAAAAAAAAAAAAAAAAAAAGTCTGGGGGAAGAAAAAAACTAAAATTC
TTAAAAAAAAAAAAAAAAAGGCTATTATCAAACTGATTTCTCCCTTTTTGTATGCCGGATGCTGCATGAGTCTGAAACAC
CAATAAACGGAGACTGCATGAGActcgcctccaatctcggttggttcctgcgttcgtcccgccggcccggcggtgctgc
ctttctggcagaaccttactgggtggtatacgcatgcgacttcc
```

FIGURE 4
A
Family 1 (ICCA): c.649-650insC (p.R217fsX224)
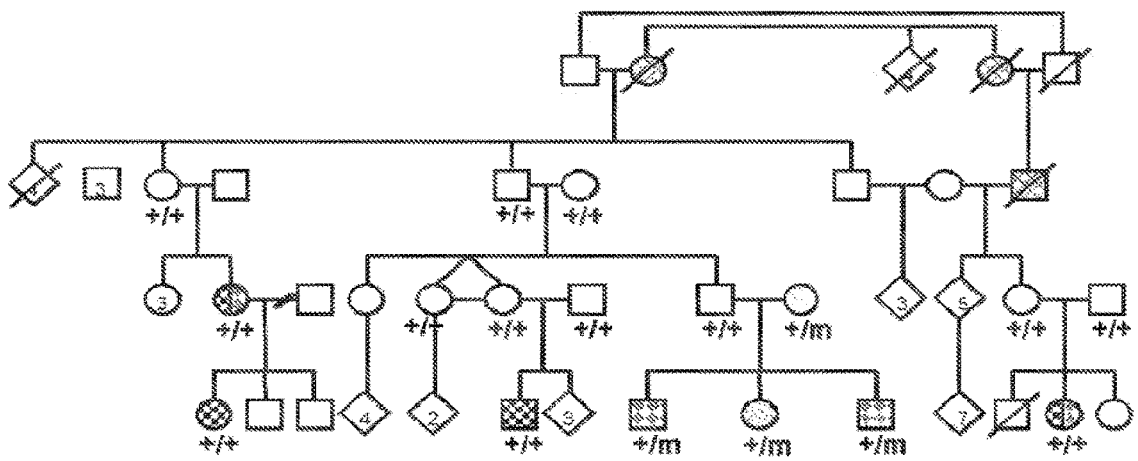
B
Family 2 (ICCA): c.649-650insC (p.R217fsX224)
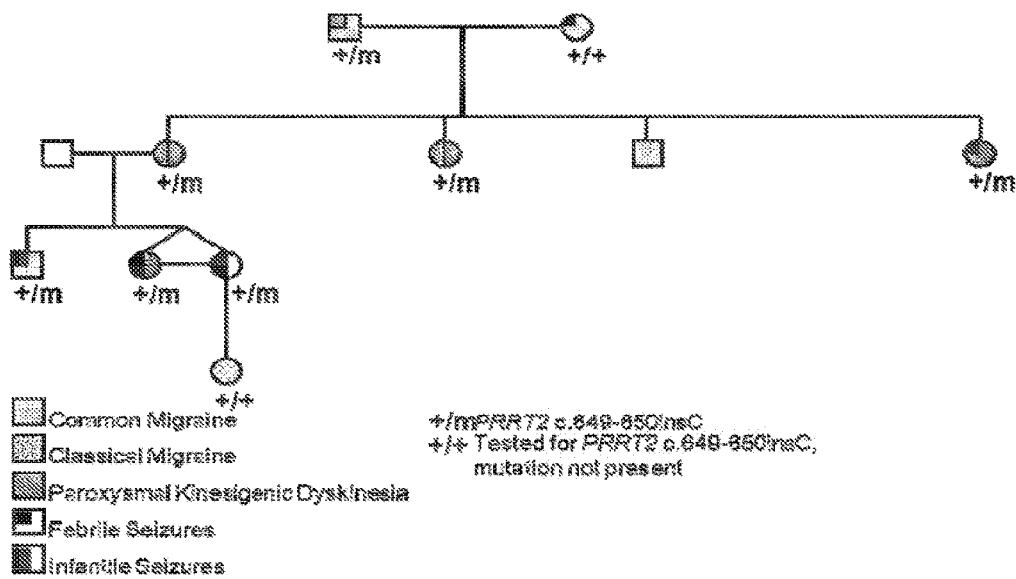

FIGURE 4 (Continued)
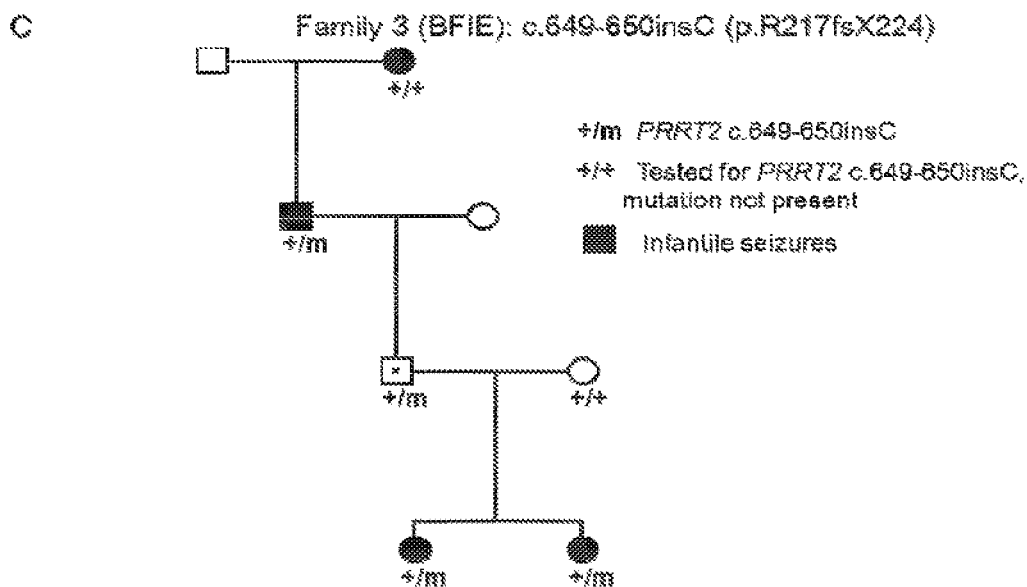
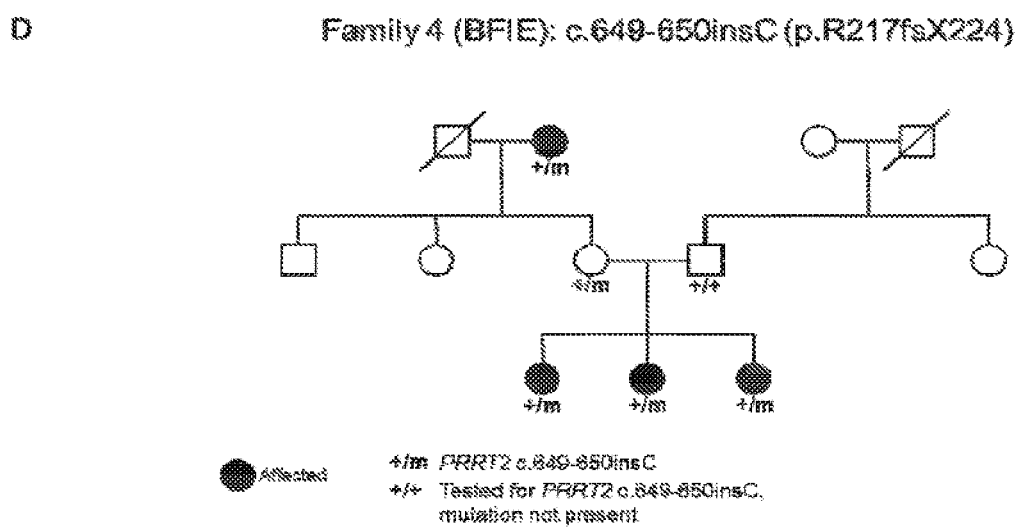

FIGURE 4 (Continued)
E    Family 5 (ICCA): c.649-650insC (p.R217fsX224)
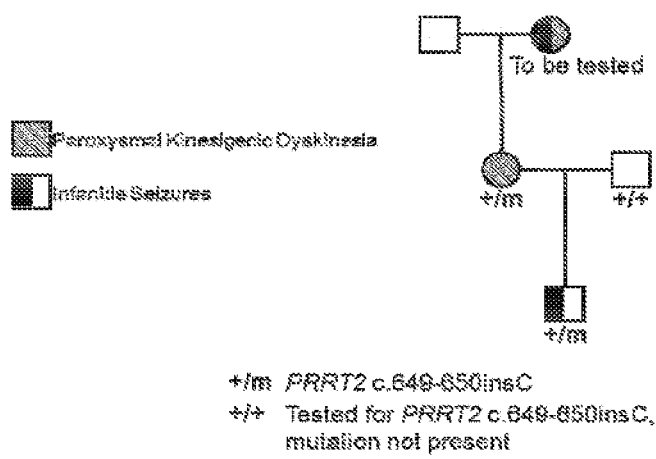
F    Family 6 (BFIE): c.649-650insC (p.R217fsX224)
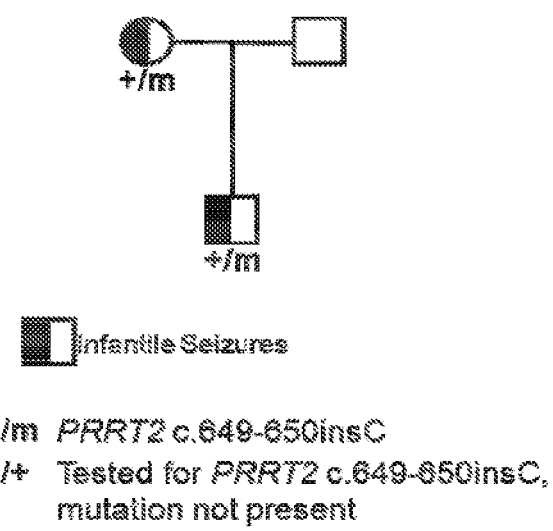

FIGURE 4 (Continued)
G  Family 7 (ICCA): c.649-650insC (p.R217fsX224)
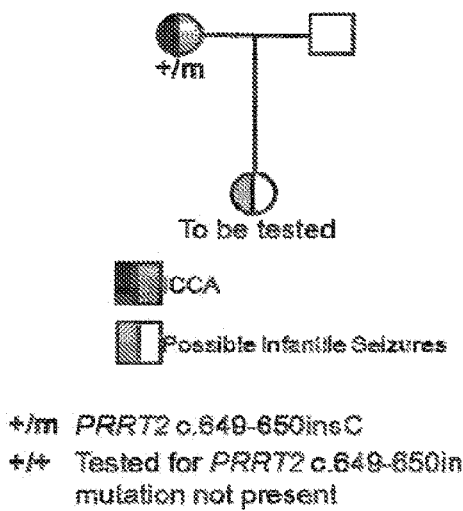
+/m  PRRT2 c.649-650insC
+/+  Tested for PRRT2 c.649-650insC, mutation not present
H  Family 8 (Sporadic Infantile Seizures): c.649-650insC (p.R217fsX224)
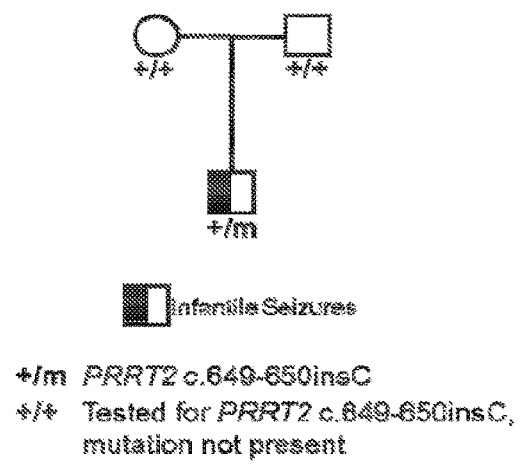
+/m  PRRT2 c.649-650insC
+/+  Tested for PRRT2 c.649-650insC, mutation not present FIGURE 4 (Continued)
I Family 9 (BFIE): c.649-650insC (p.R217fsX224)
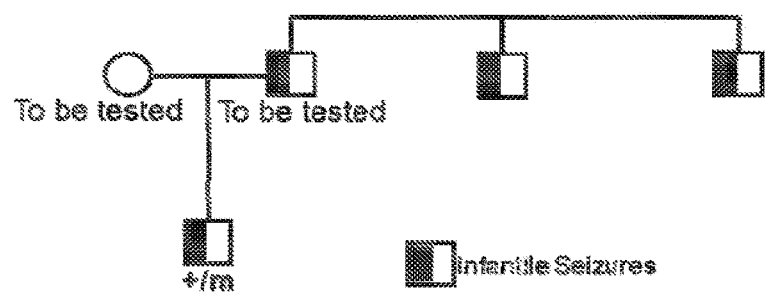
+/m  *PRRT2* c.649-650insC
+/+  Tested for *PRRT2* c.649-650insC,
     mutation not present
J Family 10 (ICCA): c.649-650insC (p.R217fsX224)
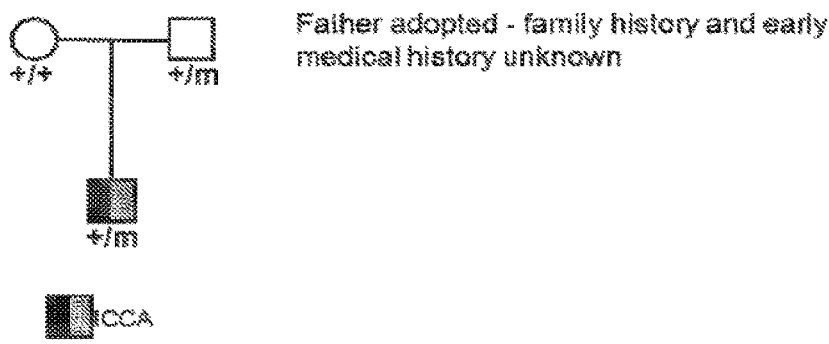
+/m  *PRRT2* c.649-650insC
+/+  Tested for *PRRT2* c.649-650insC,
     mutation not present K  Family 11 (Benign Infantile Seizures): c.649-650insC (p.R217fsX224)

+/m  *PRRT2* c.649-650insC
+/+  Tested for *PRRT2* c.649-650insC, mutation not present

SEQUENCE LISTING

```
<160> NUMBER OF SEQ ID NOS: 26

<210> SEQ ID NO 1
<211> LENGTH: 1021
<212> TYPE: DNA
<213> ORGANISM: Homo sapiens

<400> SEQUENCE: 1
atggcagcca gcagctctga gatctctgag atgaaggggg ttgaggagag tcccaaggtt      60
ccaggcgaag ggcctggcca ttctgaagct gaaactggcc ctccccaggt cctagcaggg     120
gtaccagacc agccagaggc cccgcagcca ggtccaaaca ccactgcggc ccctgtggac     180
tcagggccca aggctgggct ggctccagaa accacagaga ccccggctgg ggcctcagaa     240
acagcccagg ccacagacct cagcttaagc ccaggagggg aatcaaaggc caactgcagc     300
cccgaagacc catgccaaga aacagtgtcc aaaccagaag tgagcaaaga ggccactgca     360
gaccaggggt ccaggctgga gtctgcagcc ccacctgaac cagccccaga gcctgctccc     420
caaccagacc cccggccaga ttcccagcct acccccaagc cagcccttca accagagctc     480
```

```
cctacccagg aggaccccac ccctgagatt ctgtctgaga gtgtagggga aaagcaagag    540
aatggggcag tggtgcccct gcaggctggt gatggggaag agggcccagc ccctgagcct    600
cactcaccac cctcaaaaaa atccccgccc agccaatggg gccccccccc gagtgctgca    660
gcagctggtt gaggaggatc gaatgagaag ggcacacagt gggcatccag gatctccccg    720
aggtagcctg agccgccacc ccagctccca gctggcaggt cctggggtgg aggggggtga    780
aggcacccag aaacctcggg actacatcat ccttgccatc ctgtcctgct tctgccccat    840
gtggcctgtc aacatcgtgg ccttcgctta tgctgtcatg tcccggaaca gcctgcagca    900
gggggacgtg gacggggccc agcgtctggg ccgggtagcc aagctcttaa gcatcgtggc    960
gctggtgggg ggagtcctca tcatcatcgc ctcctgcgtc atcaacttag gcgtgtataa    1020
g                                                                  1021
```

<210> SEQ ID NO 2
<211> LENGTH: 223
<212> TYPE: PRT
<213> ORGANISM: Homo sapiens

<400> SEQUENCE: 2

```
Met Ala Ala Ser Ser Ser Glu Ile Ser Glu Met Lys Gly Val Glu Glu
1               5                   10                  15

Ser Pro Lys Val Pro Gly Glu Gly Pro Gly His Ser Glu Ala Glu Thr
            20                  25                  30

Gly Pro Pro Gln Val Leu Ala Gly Val Pro Asp Gln Pro Glu Ala Pro
        35                  40                  45

Gln Pro Gly Pro Asn Thr Thr Ala Ala Pro Val Asp Ser Gly Pro Lys
    50                  55                  60

Ala Gly Leu Ala Pro Glu Thr Thr Glu Thr Pro Ala Gly Ala Ser Glu
65                  70                  75                  80

Thr Ala Gln Ala Thr Asp Leu Ser Leu Ser Pro Gly Gly Glu Ser Lys
                85                  90                  95

Ala Asn Cys Ser Pro Glu Asp Pro Cys Gln Glu Thr Val Ser Lys Pro
            100                 105                 110

Glu Val Ser Lys Glu Ala Thr Ala Asp Gln Gly Ser Arg Leu Glu Ser
        115                 120                 125

Ala Ala Pro Pro Glu Pro Ala Pro Glu Pro Ala Pro Gln Pro Asp Pro
    130                 135                 140

Arg Pro Asp Ser Gln Pro Thr Pro Lys Pro Ala Leu Gln Pro Glu Leu
145                 150                 155                 160

Pro Thr Gln Glu Asp Pro Thr Pro Glu Ile Leu Ser Glu Ser Val Gly
                165                 170                 175

Glu Lys Gln Glu Asn Gly Ala Val Val Pro Leu Gln Ala Gly Asp Gly
            180                 185                 190

Glu Glu Gly Pro Ala Pro Glu Pro His Ser Pro Ser Lys Lys Ser
        195                 200                 205

Pro Pro Ser Gln Trp Gly Pro Pro Ser Ala Ala Ala Ala Gly
    210                 215                 220
```

<210> SEQ ID NO 3
<211> LENGTH: 1021
<212> TYPE: DNA
<213> ORGANISM: Homo sapiens

<400> SEQUENCE: 3

```
atggcagcca gcagctctga gatctctgag atgaagggg ttgaggagag tcccaaggtt      60
ccaggcgaag ggcctggcca ttctgaagct gaaactggcc ctccccaggt cctagcaggg    120
gtaccagacc agccagaggc cccgcagcca ggtccaaaca ccactgcggc ccctgtggac    180
tcagggccca aggctgggct ggctccagaa accacagaga ccccggctgg ggcctcagaa    240
acagcccagg ccacagacct cagcttaagc ccaggagggg aatcaaaggc caactgcagc    300
cccgaagacc catgccaaga aacagtgtcc aaaccagaag tgagcaaaga ggccactgca    360
gaccagggt ccaggctgga gtctgcagcc ccacctgaac cagccccaga gcctgctccc     420
caaccagacc cccggccaga ttcccagcct accccccaagc cagcccttca accagagctc   480
cctacccagg aggaccccac ccctgagatt ctgtctgaga gtgtagggga aaagcaagag   540
aatgggcag tggtgcccct gcaggctggt gatgggaag agggcccagc ccctgagcct     600
cactcaccac cctcaaaaaa atcccccca gccaatgggg ccccccccc gagtgctgca     660
gcagctggtt gaggaggatc gaatgagaag ggcacacagt gggcatccag gatctccccg   720
aggtagcctg agccgccacc ccagctccca gctggcaggt cctggggtgg aggggggtga   780
aggcacccag aaacctcggg actacatcat ccttgccatc ctgtcctgct tctgccccat    840
gtggcctgtc aacatcgtgg ccttcgctta tgctgtcatg tcccggaaca gcctgcagca   900
ggggacgtg acggggccc agcgtctggg ccgggtagcc aagctcttaa gcatcgtggc   960
gctggtgggg ggagtcctca tcatcatcgc ctcctgcgtc atcaacttag gcgtgtataa  1020
g                                                                 1021
```

<210> SEQ ID NO 4
<211> LENGTH: 223
<212> TYPE: PRT
<213> ORGANISM: Homo sapiens

<400> SEQUENCE: 4

```
Met Ala Ala Ser Ser Ser Glu Ile Ser Glu Met Lys Gly Val Glu Glu
1               5                   10                  15

Ser Pro Lys Val Pro Gly Glu Gly Pro Gly His Ser Glu Ala Glu Thr
            20                  25                  30

Gly Pro Pro Gln Val Leu Ala Gly Val Pro Asp Gln Pro Glu Ala Pro
        35                  40                  45

Gln Pro Gly Pro Asn Thr Thr Ala Ala Pro Val Asp Ser Gly Pro Lys
    50                  55                  60

Ala Gly Leu Ala Pro Glu Thr Thr Glu Thr Pro Ala Gly Ala Ser Glu
65                  70                  75                  80

Thr Ala Gln Ala Thr Asp Leu Ser Leu Ser Pro Gly Gly Glu Ser Lys
                85                  90                  95

Ala Asn Cys Ser Pro Glu Asp Pro Cys Gln Glu Thr Val Ser Lys Pro
            100                 105                 110

Glu Val Ser Lys Glu Ala Thr Ala Asp Gln Gly Ser Arg Leu Glu Ser
        115                 120                 125

Ala Ala Pro Glu Pro Ala Pro Glu Pro Ala Pro Gln Pro Asp Pro
    130                 135                 140

Arg Pro Asp Ser Gln Pro Thr Pro Lys Pro Ala Leu Gln Pro Glu Leu
145                 150                 155                 160

Pro Thr Gln Glu Asp Pro Thr Pro Glu Ile Leu Ser Glu Ser Val Gly
                165                 170                 175

Glu Lys Gln Glu Asn Gly Ala Val Val Pro Leu Gln Ala Gly Asp Gly
            180                 185                 190
```

Glu Glu Gly Pro Ala Pro Glu Pro His Ser Pro Ser Lys Lys Ser
    195                 200                 205

Pro Pro Ala Asn Gly Ala Pro Pro Ser Ala Ala Ala Ala Gly
    210                 215                 220

<210> SEQ ID NO 5
<211> LENGTH: 3994
<212> TYPE: DNA
<213> ORGANISM: Homo sapiens

<400> SEQUENCE: 5

| | | | | | |
|---|---|---|---|---|---|
| cgggaggggc | cggggactta | agaaggaggc | gtctctcctg | gaggcgcgcg | tgagaagggg | 60 |
| cagggagggg | gcgcgagtgg | tccccgggcc | ggttgcctgg | gtaacgcgtg | gctcccttgg | 120 |
| gctggcggga | ggggccggag | gctcgcgagg | ggcggggggcg | gcgacggcgg | cggagcgtag | 180 |
| gggaggggac | cggagaggag | gggatgagca | cacgggagag | gagaagaggg | agacccgccg | 240 |
| cctcccctccc | tccctagctg | acttgctccc | tcccggctg | cggctgctgc | aaaagccagc | 300 |
| agcggcagcg | ggagctgtcc | ggaggccggc | gtcgaggtga | gacccgggca | gactgaggct | 360 |
| gcgggtagga | gtggaccgac | cgacggctga | cgccgggcgg | actgcacggg | aatgcgggtg | 420 |
| tctggagggc | tggtggtggt | gctgggcggg | ctgaaccatc | gggaggaggc | gccagcccac | 480 |
| cgaaggcgag | ggaagccccg | ggagagggc | tgacagggga | tcgaaggaga | taaccaggtc | 540 |
| ccccagaaag | gggcgggagc | gtcctcgccc | taaacgcgca | gcaagaaaac | ccgcaccgcc | 600 |
| tgggagccca | gggaggaggg | gaggatgcag | agggagtgga | atgcgaatgt | cgggtccctct | 660 |
| gcccagtcgg | cctgtcggag | tgctatttgc | acagctcgtt | gattttgggg | tgctgggatc | 720 |
| tgagagtctg | gatcttgttg | gatggaccca | gggagagacc | ctggagaagg | tcctgtttac | 780 |
| aaaagggtta | atcttcccca | gggctctcca | agcagaagac | tttgagtaga | gcactcctcc | 840 |
| cgcagggatg | tcccacccta | aggcaaagga | aaccccaact | tttcttcctc | tcccctagagg | 900 |
| cagtgcaagg | ctggccctga | gacaggaatg | tggcccaatt | gggcctgcag | tgctgagcgc | 960 |
| cctcttccct | cctcacccca | agcctatctc | ctcctcttcc | agggtttgcc | gctgtctctg | 1020 |
| ctattccatc | ctccccatag | gggctctctc | ccctctccca | tctcaagatg | gcagccagca | 1080 |
| gctctgagat | ctctgagatg | aagggggttg | aggagagtcc | caaggttcca | ggcgaagggc | 1140 |
| ctggccattc | tgaagctgaa | actggccctc | cccaggtcct | agcaggggta | ccagaccagc | 1200 |
| cagaggcccc | gcagccaggt | ccaaacacca | ctgcggcccc | tgtggactca | gggcccaagg | 1260 |
| ctgggctggc | tccagaaacc | acagagaccc | cggctgggc | ctcagaaaca | gcccaggcca | 1320 |
| cagacctcag | cttaagccca | ggagggaat | caaaggccaa | ctgcagcccc | gaagacccat | 1380 |
| gccaagaaac | agtgtccaaa | ccagaagtga | gcaaagaggc | cactgcagac | caggggtcca | 1440 |
| ggctggagtc | tgcagcccca | cctgaaccag | cccagagcc | tgctccccaa | ccagaccccc | 1500 |
| ggccagattc | ccagcctacc | cccaagccag | cccttcaacc | agagctccct | acccaggagg | 1560 |
| accccacccc | tgagattctg | tctgagagtg | taggggaaaa | gcaagagaat | ggggcagtgg | 1620 |
| tgccctgca | ggctggtgat | ggggaagagg | gcccagcccc | tgagcctcac | tcaccaccct | 1680 |
| caaaaaaatc | cccccagcc | aatgggccc | cccccgagt | gctgcagcag | ctggttgagg | 1740 |
| aggatcgaat | gagaagggca | cacagtgggc | atccaggatc | tccccgaggt | agcctgagcc | 1800 |
| gccaccccag | ctcccagctg | gcaggtcctg | gggtggaggg | gggtgaaggc | acccagaaac | 1860 |
| ctcgggacta | catcatcctt | gccatcctgt | cctgcttctg | ccccatgtgg | cctgtcaaca | 1920 |

```
tcgtggcctt cgcttatgct gtcatgttga gccccatggg accctagccc aggcctgctg      1980
tggctcccag cttcccgcca gcgctgcaat agagcctctg gagtaatcat gccttccttc      2040
ccctctcctc tctgcatgga tcccacctcc ccaattccag ggcctttgtt tgcctctccc      2100
taggacctaa ccctctgagc caccactgcc ctgccccttt gggtgggagg gatatggaaa      2160
cacgtgtcac acagcctcgc tgacctgtgc cctcctcccc ctgccccttc actcctcctt      2220
cctcccttac ccgccatcta tggggctggc ctctctctct tctggatgac ttttccacct      2280
gatcccttct gggctggctt ctcctgaccc cggctatgtg cctccacccc tcgccctaac      2340
cccagtcccg gaacagcctg cagcagggg acgtggacgg ggcccagcgt ctgggccggg       2400
tagccaagct cttaagcatc gtggcgctgg tgggggagt cctcatcatc atcgcctcct       2460
gcgtcatcaa cttaggcggt gagtggggc ttgggacagg caggggagga atggaagggt       2520
tggcaagggc agctttacta accctgccc ctgctctctc ctgtctgtcc tccttacctc       2580
tcctttgtct ctccttgtct ccccctccc ccgtctgtcc ttccctctcc tctcccacag       2640
tgtataagtg aggggctctg ccccgcatcc caagactttt cttcctgttg ggagctgcct      2700
tgggcccatc cctcccctgg ggggagccca actgatggcc ctggccccca ccctaagga      2760
ccaagggagc ctgagcggcc ttgtttacag ctttctgtcct gctcctgcat cttgccaggc      2820
tcctctgcca actgtaggcc tgcctcatcc ctgcactggt tccaacctcc ctgcactaat      2880
gcctgcatcc cctccggcct cttggccccc tatccctgca cttctggaaa cctccctgca      2940
ctctggaaac ctccctgaac acctccccaa ctctgcgctc tcagcctccc tgcatctctc      3000
ctggcctccc tgcacttctt ccagcccccc aaattctctg acctccacc ctggccgcct       3060
cctcccaact ttcattgtct tggcatctct caaccctcag tcctctcttc cttcccttct      3120
ttatcatctc ccctttcctc tccacgtccc gccccttcc tcttcctgcc tcctcatctc       3180
ccttaagcat cctcttctcc aacctcccgt caccgtttac tctgcaaaat tgacagcact      3240
tagacgagc ttgggggcag ggagcagtgt tgggagaggg ctccccaacc ccaggctcgg       3300
actgttctct gctgggacca cccagggtcg gacacccaag ggtgcctggc aggtcgcaga      3360
gttggcaagc cgggcctcgt atggggactc gggtgagggt ggcgagtact ggttccgaac      3420
gcacgcaggg gagaagggag ggacgcggcg ctgacccttc caggtcagct ggagttgacc      3480
cgcccacctg gcttttcaa ccccagtccg cgagtttctt tcttgaaggt gtggggcta       3540
gattcattca cgtgcttcgt aatgaaataa tccaaaaaat aggaccaaag cgcccactgg      3600
caggagcgag ggcggggcgc cgcgctctat aattattttc taagatgatg ggggaggttt      3660
gttgcacgcg acagcccgct gaggaggcgg ggaccgagct acaacgcggt tcggatttgg      3720
cgggggtttt tttccttaaa aaaaaaaaaa aaaaaaaaa aaaagtctgg gggaagaaaa      3780
aaactaaaat tcttaaaaaa aaaaaaaaaa ggctattatc aaactgatttt ctcccttttt     3840
gtatgccgga tgctgcatga gtctgaaaca ccaataaacg gagactgcat gagactcgcc      3900
tccaatctcg gttggttcct gcgttcgtcc cgccggcccg gcggtgctgc ctttctggca      3960
gaaccttact gggtggtata cgcatgcgac ttcc                                  3994

<210> SEQ ID NO 6
<211> LENGTH: 3994
<212> TYPE: DNA
<213> ORGANISM: Homo sapiens

<400> SEQUENCE: 6
cgggaggggc cggggactta agaaggaggc gtctctcctg gaggcgcgcg tgagaagggg          60
```

```
cagggagggg gcgcgagtgg tccccgggcc ggttgcctgg gtaacgcgtg gctcccttgg    120
gctggcggga gggccggag gctcgcgagg gcgggggcg gcgacggcgg cggagcgtag     180
gggaggggac cggagaggag gggatgagca cacgggagag gagaagaggg agacccgccg    240
cctccctccc tccctagctg acttgctccc tcccgggctg cggctgctgc aaaagccagc    300
agcggcagcg ggagctgtcc ggaggccggc gtcgaggtga acccgggca gactgaggct     360 gcgggtagga gtggaccgac cgacggctga cgccgggcgg actgcacggg aatgcgggtg    420
tctggagggc tggtggtggt gctgggcggg ctgaaccatc gggaggaggc gccagcccac    480
cgaaggcgag ggaagccccg ggagagggc tgacagggga tcgaaggaga taaccaggtc     540
ccccagaaag gggcgggagc gtcctcgccc taaacgcgca gcaagaaaac ccgcaccgcc    600
tgggagccca gggaggaggg gaggatgcag agggagtgga atgcgaatgt cgggtcctct    660
gcccagtcgg cctgtcggag tgctatttgc acagctcgtt gattttgggg tgctgggatc    720
tgagagtctg gatcttgttg gatgaccca gggagagacc ctggagaagg tcctgtttac      780
aaaagggtta atcttcccca gggctctcca agcagaagac tttgagtaga gcactcctcc    840
cgcagggatg tcccacccta aggcaaagga accccaact tttcttcctc tcccctagagg    900 cagtgcaagg ctggccctga dacaggaatg tggcccaatt gggcctgcag tgctgagcgc    960
cctcttccct cctcacccca agcctatctc ctcctcttcc agggtttgcc gctgtctctg    1020
ctattccatc ctccccatag gggctctctc ccctctccca tctcaagatg gcagccagca    1080
gctctgagat ctctgagatg aagggggttg aggagagtcc caaggttcca ggcgaagggc    1140
ctggccattc tgaagctgaa actggccctc cccaggtcct agcagggta ccagaccagc     1200 cagaggcccc gcagccaggt ccaaacacca ctgcggcccc tgtggactca gggcccaagg    1260
ctgggctggc tccagaaacc acagagaccc cggctggggc ctcagaaaca gcccaggcca    1320
cagacctcag cttaagccca ggaggggaat caaaggccaa ctgcagcccc gaagacccat    1380
gccaagaaac agtgtccaaa ccagaagtga gcaaagaggc cactgcagac caggggtcca    1440
ggctggagtc tgcagcccca cctgaaccag cccagagcc tgctcccaa ccagaccccc      1500 ggccagattc ccagcctacc cccaagccag cccttcaacc agagctccct acccaggagg    1560
accccacccc tgagattctg tctgagagtg taggggaaaa gcaagagaat ggggcagtgg    1620
tgcccctgca ggctggtgat ggggaagagg gcccagcccc tgagcctcac tcaccaccct    1680
caaaaaaatc cccccagcc aatggggccc cccccgagt gctgcagcag ctggttgagg      1740
aggatcgaat gagaagggca cacagtgggc atccaggatc tccccgaggt agcctgagcc    1800 gccacccag ctcccagctg gcaggtcctg gggtggaggg gggtgaaggc acccagaaac     1860
ctcgggacta catcatcctt gccatcctgt cctgcttctg ccccatgtgg cctgtcaaca    1920
tcgtggcctt cgcttatgct gtcatggtga accccatggg accctagccc aggcctgctg    1980
tggctcccag cttcccgcca gcgctgcaat agagcctctg gagtaatcat gccttccttc    2040
ccctctcctc tctgcatgga tcccacctcc ccaattccag ggcctttgtt tgcctctccc    2100
taggacctaa ccctctgagc caccactgcc ctgccccttt gggtgggagg gatatggaaa    2160
cacgtgtcac acagcctcgc tgacctgtgc cctcctcccc ctgccccttc actcctcctt    2220
cctcccttac ccgccatcta tggggctggc ctctctctct tctggatgac ttttccacct    2280
gatcccttct gggctggctt ctcctgaccc cggctatgtg cctccacccc tcgccctaac    2340
cccagtcccg gaacagcctg cagcagggg acgtggacgg ggcccagcgt ctgggccggg    2400
```

-continued

```
tagccaagct cttaagcatc gtggcgctgg tgggggagt cctcatcatc atcgcctcct      2460
gcgtcatcaa cttaggcggt gagtgggggc ttgggacagg caggggagga atggaagggt      2520
tggcaagggc agctttacta acccctgccc ctgctctctc ctgtctgtcc tccttacctc      2580
tcctttgtct ctccttgtct cccctcccc ccgtctgtcc ttccctctcc tctcccacag      2640
tgtataagtg aggggctctg ccccgcatcc caagactttt cttcctgttg ggagctgcct      2700
tgggcccatc cctcccctgg ggggagccca actgatggcc ctggccccca ccctaaggga      2760
ccaagggagc ctgagcggcc ttgtttacag cttctgtcct gctcctgcat cttgccaggc      2820
tcctctgcca actgtaggcc tgcctcatcc ctgcactggt tccaacctcc ctgcactaat      2880
gcctgcatcc cctccggcct cttggccccc tatccctgca cttctggaaa cctccctgca      2940
ctctggaaac ctccctgaac acctcccaa ctctgcgctc tcagcctccc tgcatctctc      3000
ctggcctccc tgcacttctt ccagccccc aaattctctg gacctccacc ctggccgcct      3060
cctcccaact ttcattgtct tggcatctct caaccctcag tcctctcttc cttcccttct      3120
ttatcatctc ccctttcctc tccacgtccc gccccttcc tcttcctgcc tcctcatctc      3180
ccttaagcat cctcttctcc aacctcccgt caccgtttac tctgcaaaat tgacagcact      3240
tagacgaggc ttgggggcag ggagcagtgt tgggagaggg ctccccaacc ccaggctcgg      3300
actgttctct gctgggacca cccagggtcg acacccaag ggtgcctggc aggtcgcaga      3360
gttggcaagc cgggcctcgt atggggactc gggtgagggt ggcgagtact ggttccgaac      3420
gcacgcaggg gagaagggag ggacgcggcg ctgacccttc caggtcagct ggagttgacc      3480
cgcccacctg ggcttttcaa ccccagtccg cgagtttctt tcttgaaggt gtggggcta      3540
gattcattca cgtgcttcgt aatgaaataa tccaaaaat aggaccaaag cgcccactgg      3600
caggagcgag ggcggggcgc cgcgctctat aattattttc taagatgatg ggggaggttt      3660
gttgcacgcg acagcccgct gaggaggcgg ggaccgagct acaacgcggt tcggatttgg      3720
cgggggtttt tttccttaaa aaaaaaaaaa aaaaaaaaaa aaaagtctgg gggaagaaaa      3780
aaactaaaat tcttaaaaaa aaaaaaaaaa ggctattatc aaactgattt ctcccttttt      3840
gtatgccgga tgctgcatga gtctgaaaca ccaataaacg gagactgcat gagactcgcc      3900
tccaatctcg gttggttcct gcgttcgtcc cgccggcccg gcggtgctgc ctttctggca      3960
gaaccttact gggtggtata cgcatgcgac ttcc                                 3994
```

<210> SEQ ID NO 7
<211> LENGTH: 1023
<212> TYPE: DNA
<213> ORGANISM: Homo sapiens

<400> SEQUENCE: 7

```
atggcagcca gcagctctga gatctctgag atgaagggg ttgaggagag tcccaaggtt        60
ccaggcgaag ggcctggcca ttctgaagct gaaactggcc ctccccaggt cctagcaggg      120
gtaccagacc agccagaggc cccgcagcca ggtccaaaca ccactgcggc ccctgtggac      180
tcagggccca aggctgggct ggctccagaa accacagaga ccccggctgg ggcctcagaa      240
acagcccagg ccacagacct cagcttaagc ccaggagggg aatcaaaggc caactgcagc      300
cccgaagacc catgccaaga aacagtgtcc aaaccagaag tgagcaaaga ggccactgca      360
gaccaggggt ccaggctgga gtctgcagcc ccacctgaac cagccccaga gcctgctccc      420
caaccagacc cccggccaga ttcccagcct acccccaagc cagcccttca accagagctc      480
cctacccagg aggaccccac ccctgagatt ctgtctgaga gtgtagggga aaagcaagag      540
```

-continued

```
aatgggcag tggtgccct gcaggctggt gatggggaag agggcccagc ccctgagcct      600
cactcaccac cctcaaaaaa atcccccca gccaatgggg ccccccccg agtgctgcag      660
cagctggttg aggaggatcg aatgagaagg gcacacagtg ggcatccagg atctccccga   720
ggtagcctga gccgccaccc cagctcccag ctggcaggtc ctggggtgga gggggtgaa    780
ggcacccaga aacctcggga ctacatcatc cttgccatcc tgtcctgctt ctgccccatg  840
tggcctgtca acatcgtggc cttcgcttat gctgtcatgt cccggaacag cctgcagcag  900
ggggacgtgg acgggcccca gcgtctgggc cgggtagcca agctcttaaa catcgtggcg  960
ctggtgggg gagtcctcat catcatcgcc tcctgcgtca tcaacttagg cgtgtataag  1020
tga                                                                 1023
```

<210> SEQ ID NO 8
<211> LENGTH: 340
<212> TYPE: PRT
<213> ORGANISM: Homo sapiens

<400> SEQUENCE: 8

```
Met Ala Ala Ser Ser Ser Glu Ile Ser Glu Met Lys Gly Val Glu Glu
1               5                   10                  15

Ser Pro Lys Val Pro Gly Glu Gly Pro Gly His Ser Glu Ala Glu Thr
            20                  25                  30

Gly Pro Pro Gln Val Leu Ala Gly Val Pro Asp Gln Pro Glu Ala Pro
        35                  40                  45

Gln Pro Gly Pro Asn Thr Thr Ala Ala Pro Val Asp Ser Gly Pro Lys
    50                  55                  60

Ala Gly Leu Ala Pro Glu Thr Thr Glu Thr Pro Ala Gly Ala Ser Glu
65                  70                  75                  80

Thr Ala Gln Ala Thr Asp Leu Ser Leu Ser Pro Gly Gly Glu Ser Lys
                85                  90                  95

Ala Asn Cys Ser Pro Glu Asp Pro Cys Gln Glu Thr Val Ser Lys Pro
            100                 105                 110

Glu Val Ser Lys Glu Ala Thr Ala Asp Gln Gly Ser Arg Leu Glu Ser
        115                 120                 125

Ala Ala Pro Glu Pro Ala Pro Glu Pro Ala Pro Gln Pro Asp Pro
    130                 135                 140

Arg Pro Asp Ser Gln Pro Thr Pro Lys Pro Ala Leu Gln Pro Glu Leu
145                 150                 155                 160

Pro Thr Gln Glu Asp Pro Thr Pro Glu Ile Leu Ser Glu Ser Val Gly
                165                 170                 175

Glu Lys Gln Glu Asn Gly Ala Val Val Pro Leu Gln Ala Gly Asp Gly
            180                 185                 190

Glu Glu Gly Pro Ala Pro Glu Pro His Ser Pro Ser Lys Lys Ser
        195                 200                 205

Pro Pro Ala Asn Gly Ala Pro Pro Arg Val Leu Gln Gln Leu Val Glu
    210                 215                 220

Glu Asp Arg Met Arg Arg Ala His Ser Gly His Pro Gly Ser Pro Arg
225                 230                 235                 240

Gly Ser Leu Ser Arg His Pro Ser Ser Gln Leu Ala Gly Pro Gly Val
                245                 250                 255

Glu Gly Gly Glu Gly Thr Gln Lys Pro Arg Asp Tyr Ile Ile Leu Ala
            260                 265                 270

Ile Leu Ser Cys Phe Cys Pro Met Trp Pro Val Asn Ile Val Ala Phe
```

```
            275                 280                 285
Ala Tyr Ala Val Met Ser Arg Asn Ser Leu Gln Gln Gly Asp Val Asp
    290                 295                 300

Gly Ala Gln Arg Leu Gly Arg Val Ala Lys Leu Leu Asn Ile Val Ala
305                 310                 315                 320

Leu Val Gly Gly Val Leu Ile Ile Ile Ala Ser Cys Val Ile Asn Leu
                325                 330                 335

Gly Val Tyr Lys
            340

<210> SEQ ID NO 9
<211> LENGTH: 1023
<212> TYPE: DNA
<213> ORGANISM: Homo sapiens

<400> SEQUENCE: 9
atggcagcca gcagctctga gatctctgag atgaagggg ttgaggagag tcccaaggtt        60
ccaggcgaag ggcctggcca ttctgaagct gaaactggcc ctccccaggt cctagcaggg      120
gtaccagacc agccagaggc cccgcagcca ggtccaaaca ccactgcggc ccctgtggac      180
tcagggccca aggctgggct ggctccagaa accacagaga cccggctgg ggcctcagaa       240 acagcccagg ccacagacct cagcttaagc ccaggagggg aatcaaaggc caactgcagc      300
cccgaagacc catgccaaga aacagtgtcc aaaccgaaag tgagcaaaga ggccactgca      360 gaccagggt ccaggctgga gtctgcagcc ccacctgaac cagccccaga gcctgctccc       420
caaccagacc cccggccaga ttcccagcct acccccaagc cagcccttca accagagctc      480
cctacccagg aggaccccac ccctgagatt ctgtctgaga gtgtagggga aaagcaagag      540
aatggggcag tggtgcccct gcaggctggt gatggggaag agggcccagc ccctgagcct      600
cactcaccac cctcaaaaaa atcccccca gccaatgggg ccccccccg agtgctgcag        660 cagctggttg aggaggatcg aatgagaagg gcacacagtg ggcatccagg atctccccga      720
ggtagcctga gccgccaccc cagctcccag ctggcaggtc ctggggtgga ggggggtgaa      780
ggcacccaga aacctcggga ctacatcatc cttgccatcc tgtcctgctt ctgccccatg      840
tggcctgtca acatcgtggc cttcgcttat gctgtcatgt cccggaacag cctgcagcag      900
ggggacgtgg acgggcccaa gcgtctgggc cgggtagcca agctcttaag catcgtggcg      960
ctggtggggg gagtcctcat catcatcgcc tcctgcgtca tcaacttagg cgtgtataag     1020
tga                                                                   1023

<210> SEQ ID NO 10
<211> LENGTH: 340
<212> TYPE: PRT
<213> ORGANISM: Homo sapiens

<400> SEQUENCE: 10

Met Ala Ala Ser Ser Glu Ile Ser Glu Met Lys Gly Val Glu Glu
1               5                   10                  15

Ser Pro Lys Val Pro Gly Glu Gly Pro Gly His Ser Glu Ala Glu Thr
            20                  25                  30

Gly Pro Pro Gln Val Leu Ala Gly Val Pro Asp Gln Pro Glu Ala Pro
        35                  40                  45

Gln Pro Gly Pro Asn Thr Thr Ala Ala Pro Val Asp Ser Gly Pro Lys
    50                  55                  60

Ala Gly Leu Ala Pro Glu Thr Thr Glu Thr Pro Ala Gly Ala Ser Glu
```

```
                    65                  70                  75                  80
            Thr Ala Gln Ala Thr Asp Leu Ser Leu Ser Pro Gly Gly Glu Ser Lys
                            85                  90                  95
            Ala Asn Cys Ser Pro Glu Asp Pro Cys Gln Glu Thr Val Ser Lys Pro
                       100                 105                 110
            Glu Val Ser Lys Glu Ala Thr Ala Asp Gln Gly Ser Arg Leu Glu Ser
                       115                 120                 125
            Ala Ala Pro Pro Glu Pro Ala Pro Glu Pro Ala Pro Gln Pro Asp Pro
            130                 135                 140
            Arg Pro Asp Ser Gln Pro Thr Pro Lys Pro Ala Leu Gln Pro Glu Leu
            145                 150                 155                 160
            Pro Thr Gln Glu Asp Pro Thr Pro Glu Ile Leu Ser Glu Ser Val Gly
                            165                 170                 175
            Glu Lys Gln Glu Asn Gly Ala Val Val Pro Leu Gln Ala Gly Asp Gly
                       180                 185                 190
            Glu Glu Gly Pro Ala Pro Glu Pro His Ser Pro Ser Lys Lys Ser
                       195                 200                 205
            Pro Pro Ala Asn Gly Ala Pro Pro Arg Val Leu Gln Gln Leu Val Glu
            210                 215                 220
            Glu Asp Arg Met Arg Arg Ala His Ser Gly His Pro Gly Ser Pro Arg
            225                 230                 235                 240
            Gly Ser Leu Ser Arg His Pro Ser Ser Gln Leu Ala Gly Pro Gly Val
                            245                 250                 255
            Glu Gly Gly Glu Gly Thr Gln Lys Pro Arg Asp Tyr Ile Ile Leu Ala
                       260                 265                 270
            Ile Leu Ser Cys Phe Cys Pro Met Trp Pro Val Asn Ile Val Ala Phe
                       275                 280                 285
            Ala Tyr Ala Val Met Ser Arg Asn Ser Leu Gln Gln Gly Asp Val Asp
            290                 295                 300
            Gly Ala Gln Arg Leu Gly Arg Val Ala Lys Leu Leu Ser Ile Val Ala
            305                 310                 315                 320
            Leu Val Gly Gly Val Leu Ile Ile Ile Ala Ser Cys Val Ile Asn Leu
                            325                 330                 335
            Gly Val Tyr Lys
                       340

<210> SEQ ID NO 11
<211> LENGTH: 3994
<212> TYPE: DNA
<213> ORGANISM: Homo sapiens

<400> SEQUENCE: 11
cgggaggggc cggggactta agaaggaggc gtctctcctg gaggcgcgcg tgagaagggg        60
cagggagggg gcgcgagtgg tccccgggcc ggttgcctgg gtaacgcgtg gctcccttgg       120
gctggcggga gggccggag gctcgcgagg ggcgggggcg cgacggcgg cggagcgtag         180 gggagggggac cggagaggag gggatgagca cacgggagag gagaagaggg agacccgccg      240
cctccctccc tccctagctg acttgctccc tcccgggctg cggctgctgc aaaagccagc      300
agcggcagcg ggagctgtcc ggaggccggc gtcgaggtga gacccgggca gactgaggct      360
gcgggtagga gtgaccgac cgacggctga cgccgggcgg actgcacggg aatgcgggtg       420
tctggagggc tggtggtggt gctggcgggg ctgaaccatc gggaggaggc gccagcccac      480
cgaaggcgag ggaagccccg ggagagggc tgacagggga tcgaaggaga taaccaggtc       540
```

```
ccccagaaag gggcgggagc gtcctcgccc taaacgcgca gcaagaaaac ccgcaccgcc      600
tgggagccca gggaggaggg gaggatgcag agggagtgga atgcgaatgt cgggtcctct      660
gcccagtcgg cctgtcggag tgctatttgc acagctcgtt gattttgggg tgctgggatc      720
tgagagtctg gatcttgttg gatgacccca gggagagacc ctggagaagg tcctgtttac      780
aaaagggtta atcttcccca gggctctcca agcagaagac tttgagtaga gcactcctcc      840
cgcagggatg tcccacccta aggcaaagga aaccccaact tttcttcctc tccctagagg      900
cagtgcaagg ctggccctga acaggaatg tggcccaatt gggcctgcag tgctgagcgc       960
cctcttccct cctcacccca agcctatctc ctcctcttcc agggtttgcc gctgtctctg     1020
ctattccatc ctccccatag gggctctctc ccctctccca tctcaagatg gcagccagca     1080
gctctgagat ctctgagatg aagggggttg aggagagtcc caaggttcca ggcgaagggc     1140
ctggccattc tgaagctgaa actggccctc cccaggtcct agcagggggta ccagaccagc     1200 cagaggcccc gcagccaggt ccaaacacca ctgcggcccc tgtggactca gggcccaagg     1260
ctgggctggc tccagaaacc acagagaccc cggctggggc ctcagaaaca gcccaggcca     1320
cagacctcag cttaagccca ggaggggaat caaaggccaa ctgcagcccc gaagacccat     1380
gccaagaaac agtgtccaaa ccagaagtga gcaaagaggc cactgcagac caggggtcca     1440
ggctggagtc tgcagcccca cctgaaccag ccccagagcc tgctccccaa ccagaccccc     1500
ggccagattc ccagcctacc cccaagccag cccttcaacc agagctccct acccaggagg     1560
accccacccc tgagattctg tctgagagtg taggggaaaa gcaagagaat ggggcagtgg     1620
tgcccctgca ggctggtgat ggggaagagg gcccagcccc tgagcctcac tcaccaccct     1680
caaaaaaatc ccccccagcc aatggggccc ccccccgagt gctgcagcag ctggttgagg     1740
aggatcgaat gagaagggca cacagtgggc atccaggatc tccccgaggt agcctgagcc     1800
gccaccccag ctcccagctg gcaggtcctg gggtggaggg gggtgaaggc acccagaaac     1860
ctcgggacta catcatcctt gccatcctgt cctgcttctg ccccatgtgg cctgtcaaca     1920
tcgtggcctt cgcttatgct gtcatggtga gccccatggg accctagccc aggcctgctg     1980
tggctcccag cttcccgcca gcgctgcaat agagcctctg gagtaatcat gccttccttc     2040
ccctctcctc tctgcatgga tcccacctcc ccaattccag ggcctttgtt tgcctctccc     2100
taggacctaa ccctctgagc caccactgcc ctgccccttt gggtgggagg gatatggaaa     2160
cacgtgtcac acagcctcgc tgacctgtgc cctcctcccc ctgcccccttc actcctcctt     2220 cctcccttac ccgccatcta tggggctggc ctctctctct tctggatgac ttttccacct     2280
gatcccttct gggctggctt ctcctgaccc cggctatgtg cctccacccc tcgccctaac     2340
cccagtcccg gaacagcctg cagcagggg acgtggacgg ggcccagcgt ctgggccggg     2400
tagccaagct cttaagcatc gtggcgctgg tggggggagt cctcatcatc atcgcctcct     2460
gcgtcatcaa cttaggcggt gagtggggc ttgggacagg caggggagga atggaagggt      2520
tggcaagggc agctttacta accctgccc ctgctctctc ctgtctgtcc tccttacctc      2580
tcctttgtct ctccttgtct ccccctcccc ccgtctgtcc ttccctctcc tctcccacag     2640
tgtataagtg aggggctctg ccccgcatcc caagacttt cttcctgttg ggagctgcct      2700
tgggcccatc cctcccctgg ggggagccca actgatggcc ctgccccca cccctaagga      2760 ccaagggagc ctgagcggcc ttgtttacag cttctgtcct gctcctgcat cttgccaggc     2820
tcctctgcca actgtaggcc tgcctcatcc ctgcactggt tccaacctcc ctgcactaat     2880
gcctgcatcc cctccggcct cttggccccc tatccctgca cttctggaaa cctccctgca     2940
```

```
ctctggaaac ctccctgaac acctccccaa ctctgcgctc tcagcctccc tgcatctctc    3000
ctggcctccc tgcacttctt ccagccccca aaattctctg acctccacc ctggccgcct     3060 cctcccaact ttcattgtct tggcatctct caaccctcag tcctctcttc cttcccttct    3120
ttatcatctc cccttttcctc tccacgtccc gccccttcc tcttcctgcc tcctcatctc    3180
ccttaagcat cctcttctcc aacctcccgt caccgtttac tctgcaaaat tgacagcact    3240
tagacgaggc ttgggggcag ggagcagtgt tgggagaggg ctccccaacc ccaggctcgg    3300
actgttctct gctgggacca cccagggtcg acacccaag ggtgcctggc aggtcgcaga     3360
gttggcaagc cgggcctcgt atggggactc gggtgagggt ggcgagtact ggttccgaac    3420
gcacgcaggg gagaagggag ggacgcggcg ctgacccttc caggtcagct ggagttgacc    3480
cgcccacctg ggcttttcaa ccccagtccg cgagtttctt tcttgaaggt gtgggggcta    3540
gattcattca cgtgcttcgt aatgaaataa tccaaaaaat aggaccaaag cgcccactgg    3600
caggagcgag ggcggggcgc cgcgctctat aattatttc taagatgatg ggggaggttt     3660
gttgcacgcg acagcccgct gaggaggcgg ggaccgagct acaacgcggt tcggatttgg    3720
cggggggttt tttccttaaa aaaaaaaaa aaaaaaaaa aaaagtctgg gggaagaaaa      3780
aaactaaaat tcttaaaaaa aaaaaaaaa ggctattatc aaactgattt ctccctttt     3840 gtatgccgga tgctgcatga gtctgaaaca ccaataaacg gagactgcat gagactcgcc    3900
tccaatctcg gttggttcct gcgttcgtcc cgccggcccg gcggtgctgc ctttctggca    3960
gaaccttact gggtggtata cgcatgcgac ttcc                                3994

<210> SEQ ID NO 12
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 12
tcactcacca ccctcaaa                                                  18

<210> SEQ ID NO 13
<211> LENGTH: 18
<212> TYPE: DNA
<213> ORGANISM: Artificial Sequence
<220> FEATURE:
<223> OTHER INFORMATION: Oligonucleotide primer

<400> SEQUENCE: 13
cattcgatcc tcctcaac                                                  18

<210> SEQ ID NO 14
<211> LENGTH: 85
<212> TYPE: DNA
<213> ORGANISM: Homo sapiens

<400> SEQUENCE: 14
tcactcacca ccctcaaaaa aatcccccc agccaatggg gcccccccc gagtgctgca      60 gcagctggtt gaggaggatc gaatg                                          85

<210> SEQ ID NO 15
<211> LENGTH: 51
<212> TYPE: DNA
<213> ORGANISM: Artificial Sequence
<220> FEATURE:
```

<223> OTHER INFORMATION: LPO probe - MLPA analysis exon 1

<400> SEQUENCE: 15 gggttccta agggttggat gggatgagca cacgggagag gagaagaggg a      51

<210> SEQ ID NO 16
<211> LENGTH: 53
<212> TYPE: DNA
<213> ORGANISM: Artificial Sequence
<220> FEATURE:
<223> OTHER INFORMATION: RPO probe - MLPA analysis exon 1 (5'
      phosphorylated)

<400> SEQUENCE: 16
gacccgccgc ctccctccct ccctagctga tctagattgg atcttgctgg cac      53

<210> SEQ ID NO 17
<211> LENGTH: 55
<212> TYPE: DNA
<213> ORGANISM: Artificial Sequence
<220> FEATURE:
<223> OTHER INFORMATION: LPO probe - MLPA analysis exon 2-1

<400> SEQUENCE: 17 gggttccta agggttggat tctatctcct cctcttccag ggtttgccgc tgtct      55

<210> SEQ ID NO 18
<211> LENGTH: 58
<212> TYPE: DNA
<213> ORGANISM: Artificial Sequence
<220> FEATURE:
<223> OTHER INFORMATION: RPO probe - MLPA analysis exon 2-1 (5'
      phosphorylated)

<400> SEQUENCE: 18
ctgctattcc atcctcccca tagggctct ctctttctag attggatctt gctggcac      58

<210> SEQ ID NO 19
<211> LENGTH: 47
<212> TYPE: DNA
<213> ORGANISM: Artificial Sequence
<220> FEATURE:
<223> OTHER INFORMATION: LPO probe - MLPA analysis exon 2-2

<400> SEQUENCE: 19 gggttccta agggttggat ctacccagga ggaccccacc cctgaga      47

<210> SEQ ID NO 20
<211> LENGTH: 52
<212> TYPE: DNA
<213> ORGANISM: Artificial Sequence
<220> FEATURE:
<223> OTHER INFORMATION: RPO probe - MLPA analysis exon 2-2 (5'
      phosphorylated)

<400> SEQUENCE: 20
ttctgtctga gagtgtaggg gaaaagcatt ctagattgga tcttgctggc ac      52

<210> SEQ ID NO 21
<211> LENGTH: 72
<212> TYPE: DNA
<213> ORGANISM: Artificial Sequence
<220> FEATURE:
<223> OTHER INFORMATION: LPO probe - MLPA analysis exon 2-3

<400> SEQUENCE: 21

```
gggttccta agggttggag actacatcat ccttgccatc ctgtcctgct tctgccccat    60
gtggcctgtc aa                                                      72
```

<210> SEQ ID NO 22
<211> LENGTH: 52
<212> TYPE: DNA
<213> ORGANISM: Artificial Sequence
<220> FEATURE:
<223> OTHER INFORMATION: RPO probe - MLPA analysis exon 2-3 (5'
     phosphorylated)

<400> SEQUENCE: 22

```
catcgtggcc ttcgcttatg ctgtcatggt ctagattgga tcttgctggc ac           52
```

<210> SEQ ID NO 23
<211> LENGTH: 64
<212> TYPE: DNA
<213> ORGANISM: Artificial Sequence
<220> FEATURE:
<223> OTHER INFORMATION: LPO probe - MLPA analysis exon 3

<400> SEQUENCE: 23

```
gggttccta agggttggat agccaagctc ttaagcatcg tggcgctggt gggggagtc    60 ctca                                                               64
```

<210> SEQ ID NO 24
<211> LENGTH: 54
<212> TYPE: DNA
<213> ORGANISM: Artificial Sequence
<220> FEATURE:
<223> OTHER INFORMATION: RPO probe - MLPA analysis exon 3 (5'
     phosphorylated)

<400> SEQUENCE: 24

```
tcatcatcgc ctcctgcgtc atcaacttag ttctagattg gatcttgctg gcac         54
```

<210> SEQ ID NO 25
<211> LENGTH: 71
<212> TYPE: DNA
<213> ORGANISM: Artificial Sequence
<220> FEATURE:
<223> OTHER INFORMATION: LPO probe - MLPA analysis exon 4

<400> SEQUENCE: 25

```
gggttccta agggttggag accaagggag cctgagcggc ttgtttaca gcttctgtcc    60 tgctcctgca t                                                       71
```

<210> SEQ ID NO 26
<211> LENGTH: 62
<212> TYPE: DNA
<213> ORGANISM: Artificial Sequence
<220> FEATURE:
<223> OTHER INFORMATION: RPO probe - MLPA analysis exon 4 (5'
     phosphorylated)

<400> SEQUENCE: 26

```
cttgccaggc tcctctgcca actgtaggcc tgcctcatct ctagattgga tcttgctggc    60
ac                                                                  62
```

GENE AND MUTATIONS THEREOF ASSOCIATED WITH SEIZURE AND MOVEMENT DISORDERS

PRIORITY CLAIM

This application is a continuation of U.S. patent application Ser. No. 14/354,461, filed Apr. 25, 2014, which is the National Phase of International Patent Application No. PCT/AU2012/001321, filed Oct. 29, 2012, which claims priority from Australia Patent Application Nos. 2011904493, filed Oct. 28, 2011, and 2012900190, filed Jan. 18, 2012. The contents of these applications are incorporated herein by reference in their entirety.

FIELD OF THE INVENTION

The present invention relates to the proline rich transmembrane protein 2 gene (hereinafter "PRRT2"), and the identification of mutations and variations in PRRT2 that give rise to seizure disorders such as epilepsy, as well as movement and similarly related disorders. In view of the finding that PRRT2 plays a role in these disorders, the present invention enables methods for the diagnosis or prognosis of seizure and movement disorders, and enables use of the PRRT2 gene and its encoded polypeptide in drug screening assays for the identification of therapeutics for the treatment and/or prevention of such disorders.

BACKGROUND OF THE INVENTION

Seizure and movement disorders can be broadly characterised as those disorders which arise when the brain's electrical activity is periodically disturbed, resulting in some degree of temporary brain dysfunction. The boundaries between seizure disorders (such as epilepsy for example) and movement disorders are difficult to define; some syndromes or diseases may combine the two and many manifestations of one are similar to the other. Furthermore, the diagnosis of epilepsy for example can be indicative for the future development of a movement disorder. Despite that, from a clinical perspective, seizure and movement disorders are distinct from each other.

Epilepsies constitute a diverse collection of seizure disorders that affect about 3% of the population at some time in their lives. An epileptic seizure can be defined as an episodic change in behaviour caused by the disordered firing of populations of neurons in the central nervous system. This results in varying degrees of involuntary muscle contraction and often a loss of consciousness. Epilepsy syndromes have been classified into more than 40 distinct types based upon characteristic symptoms, types of seizure, cause, age of onset and Electroencephalography (EEG) patterns (Commission on Classification and Terminology of the International League Against Epilepsy, 1989). However, the single feature that is common to all epileptic syndromes is the persistent increase in neuronal excitability that is both occasionally and unpredictably expressed as a seizure.

A genetic contribution to the aetiology of epilepsy has been estimated to be present in approximately 40% of affected individuals. As epileptic seizures may be the endpoint of a number of molecular aberrations that ultimately disturb neuronal synchrony, the genetic basis for epilepsy is likely to be heterogeneous. There are over 200 Mendelian diseases which include epilepsy as part of the phenotype. In these diseases, seizures are symptomatic of underlying neurological involvement such as disturbances in brain structure or function. In contrast, there are also a number of "pure" epilepsy syndromes in which epilepsy is the sole manifestation in the affected individuals. These syndromes are termed idiopathic and account for over 60% of all epilepsy cases.

Idiopathic epilepsies have been further divided into partial and generalized sub-types. Partial (focal or local) epileptic fits arise from localized cortical discharges, so that only certain groups of muscles are involved and consciousness may be retained. However, in generalized epilepsy, EEG discharge shows no focus such that all subcortical regions of the brain are involved. Although the observation that generalized epilepsies are frequently inherited is understandable, the mechanism by which genetic defects, presumably expressed constitutively in the brain, give rise to partial seizures is less clear.

In neonates and infants, probably because brain myelination is incomplete, the distinction between partial and generalized epilepsies is less clear from clinical and neurobiological standpoints. Epilepsies in the first year of life were previously viewed as largely due to acquired perinatal factors. However, two benign autosomal dominant epilepsy syndromes are now well recognised in the first year of life. The first is benign familial neonatal epilepsy (BFNE) which usually presents around the third day of life and is characterised by tonic or clonic seizures. These seizures stop within a few weeks of age, with 5% of individuals having later febrile seizures and 11% later epilepsy. Studies have shown that the genetic basis for this syndrome in many cases is due to mutations in the potassium channel genes KCNQ2 and KCNQ3.

The second is benign familial infantile epilepsy (BFIE) which is an autosomal dominant seizure disorder of infancy in which seizure onset occurs at a mean age of 6 months with clusters of tonic or clonic partial or generalised seizures over a few days. Seizures are usually offset by around 2 years of age but it may be associated with paroxysmal dyskinesias (movement disorders) in later childhood in some individuals. Whilst no genes have been definitively identified to be causative of BFIE, a general linkage to chromosomes 19, 1 and 16 has previously been reported, with the vast majority of families showing linkage to the pericentromeric region of chromosome 16 at 16p11-16q12.1.

Movement disorders encompass a wide variety of neurological conditions affecting motor control and muscle tone. These conditions are typified by the inability to control certain bodily actions. Accordingly, these conditions pose a significant quality of life issue for patients. Nonlimiting examples of movement disorders include dyskinesias, Parkinson's syndrome, dystonias, myoclonus, chorea, tics, and tremor. Dystonia is a neurological disorder characterized by sustained, involuntary movements. These movements typically produce twisting postures. A large number of conditions produce dystonia, including genetic causes, toxin or drug-induced causes, and degenerative illnesses in which dystonia is manifested.

Essential tremor is another type of movement disorder, separate from dystonia, and is the most common cause of tremor in the adult population. Patients with essential tremor exhibit involuntary, rhythmic tremor, or shaking, of a body part. Commonly, essential tremor affects the hands, head, or voice, but it can also affect the tongue, legs, or trunk. In tasks which involve fine motor control, patients with essential tremor may have difficulty performing these skills. For example, a severe tremor in the hands makes eating, drinking, writing, and dressing, difficult. Whilst the exact cause of essential tremor is unknown, it is often inherited.

Yet another movement disorder is paroxysmal kinesigenic choreoathetosis (PKC), also known as paroxysmal kinesigenic dyskinesia (PKD). This condition is characterized by unilateral or bilateral involuntary movements precipitated by other sudden movements such as standing up from a sitting position, being startled, or changes in velocity; attacks include combinations of dystonia, choreoathetosis, and ballism, are sometimes preceded by an aura, and do not involve loss of consciousness. Attacks can be as frequent as 100 per day to as few as one per month. Attacks are usually a few seconds to five minutes in duration but can last several hours. Age of onset is typically in childhood and adolescence. Currently, the cause of familial PKC/PKD is unknown.

Infantile Convulsions and Choreoathetosis (ICCA) syndrome is a seizure and movement disorder. In ICCA, family members may have infantile seizures, PKC/PKD, or both. Families with ICCA or familial (autosomal dominant) PKC/PKD alone also show linkage to the large pericentromeric region of chromosome 16. The shared linkage region and co-occurrence of these disorders in families with ICCA has previously led to speculation that BFIE, PKC/PKD, and ICCA may be allelic.

There is a need for the identification of the causative gene(s) for the aforementioned disorders. Genes involved in these disorders will form the basis of diagnostic and therapeutic applications for patients with the disorders. This will enable proper management of affected individuals and will avoid over-investigation and over-treatment of patients.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed before the priority date of each claim of this application.

BRIEF DESCRIPTION OF THE FIGURES

For a further understanding of the aspects and advantages of the present invention, reference should be made to the following detailed description, taken in conjunction with the accompanying drawings.

FIG. 3—Nucleotide sequence of genomic DNA encompassing the PRRT2 gene. Nucleotide bases corresponding to exons are shown in uppercase, and nucleotide bases corresponding to introns, the 5' UTR and the 3'UTR are shown in lowercase. The start and stop codons are underlined.

Figure 1:
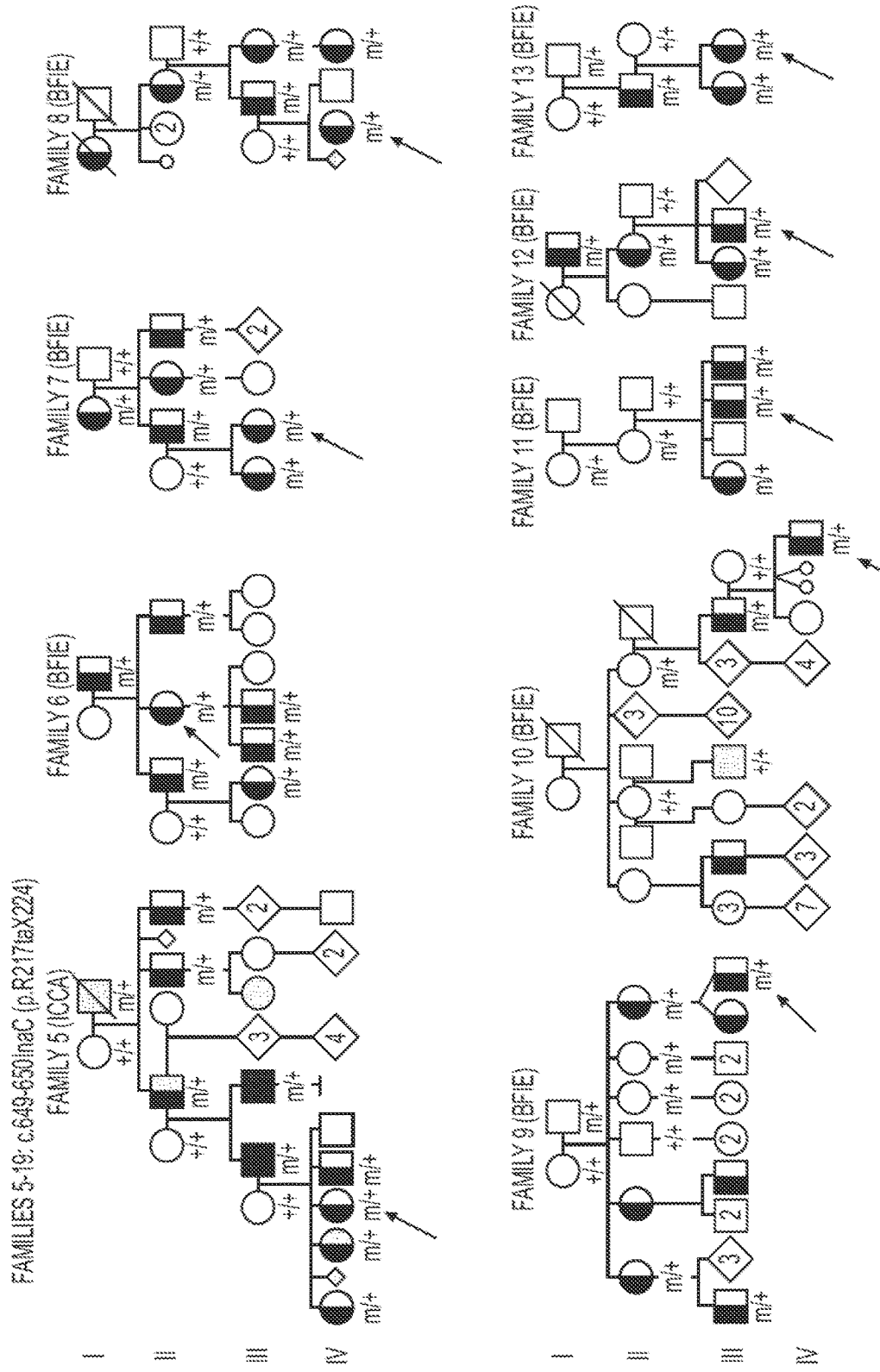
FIG. 1—Pedigrees of the 19 families with BFIE or ICCA as examined in Example 1, showing the segregation of the PRRT2 mutation within each family. Individuals with a mutation in PRRT2 are indicated by m/+ and individuals tested for mutations and found to be negative are indicated by +/+. Individuals for whom the presence of a mutation was inferred based on its presence in relatives are indicated by (m/4).
Figure 1:
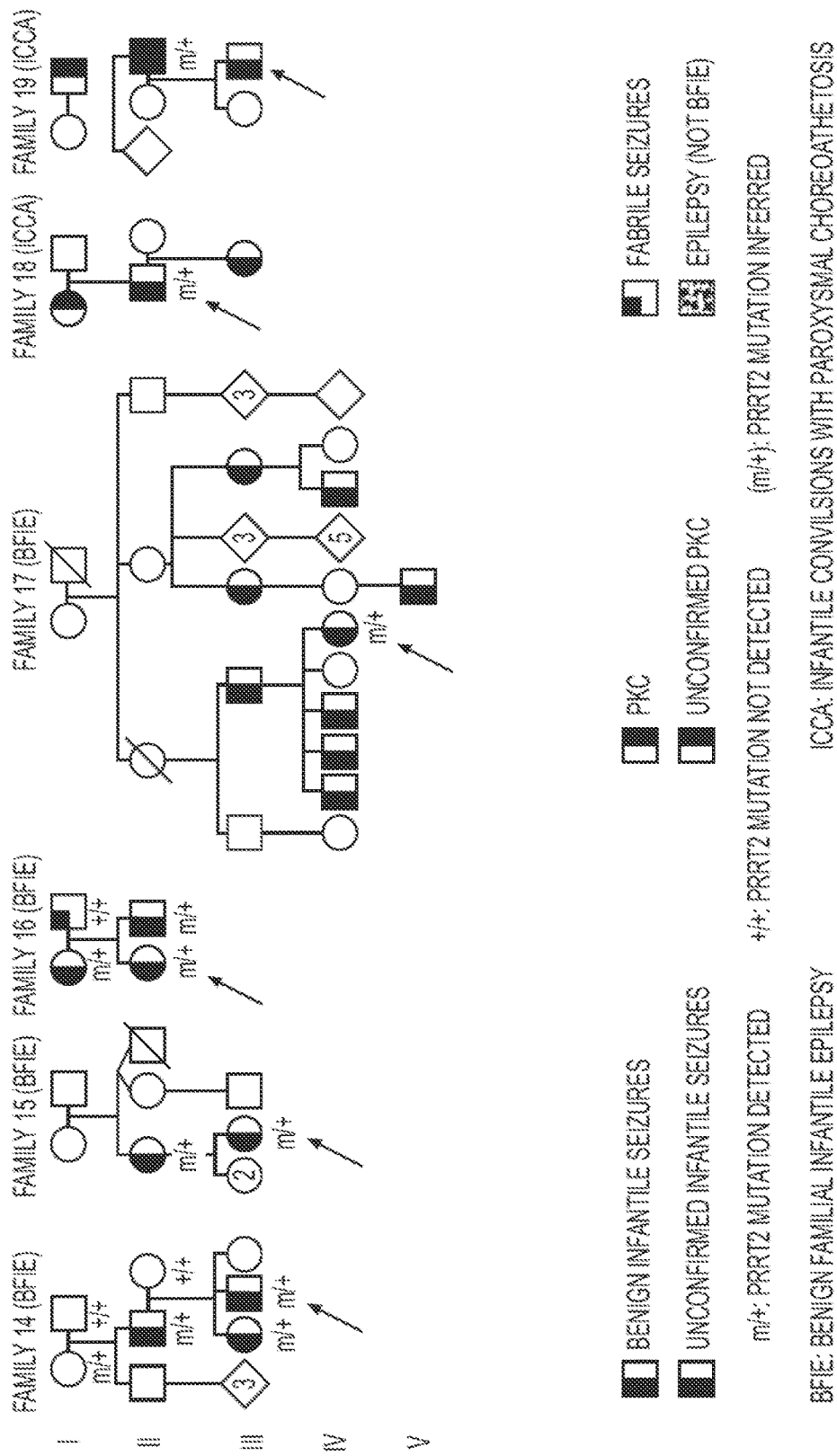

Nucleotide and polypeptide sequences are referred to herein by a sequence identifier number (SEQ ID NO:). A summary of the sequence identifiers is provided in Table 1. A sequence listing is also provided at the end of the specification.

TABLE 1

Summary of Sequence Identifiers

| Sequence Identifier | Description |
| --- | --- |
| SEQ ID NO: 1 | PRRT2 frameshift mutation (c.629-630insC) - nucleotide sequence |
| SEQ ID NO: 2 | Amino acid sequence of c.629-630insC frameshift mutation |
| SEQ ID NO: 3 | PRRT2 frameshift mutation (c.649-650insC) - nucleotide sequence |
| SEQ ID NO: 4 | Amino acid sequence of c.649-650insC frameshift mutation |
| SEQ ID NO: 5 | PRRT2 splice site mutation (IVS2 + 1G > T) - nucleotide sequence |
| SEQ ID NO: 6 | PRRT2 splice site mutation (IVS2 + 5G > A) - nucleotide sequence |
| SEQ ID NO: 7 | PRRT2 missense mutation (c.950G > A) - nucleotide sequence |
| SEQ ID NO: 8 | Amino acid sequence of c.950G > A missense mutation |
| SEQ ID NO: 9 | PRRT2 wild-type nucleotide sequence - coding region |
| SEQ ID NO: 10 | PRRT2 wild-type amino acid sequence |
| SEQ ID NO: 11 | PRRT2 wild-type nucleotide sequence - genomic |
| SEQ ID NO: 12 | F Primer for PCR amplification of the PRRT2 c.649-650insC mutation |
| SEQ ID NO: 13 | R Primer for PCR amplification of the PRRT2 c.649-650insC mutation |
| SEQ ID NO: 14 | Sequence of PCR product amplified using the F and R primer |
| SEQ ID NO: 15 | MLPA analysis-LPO Probe - PRRT2 exon 1 |
| SEQ ID NO: 16 | MLPA analysis-RPO Probe - PRRT2 exon 1 |
| SEQ ID NO: 17 | MLPA analysis-LPO Probe - PRRT2 exon 2-1 |
| SEQ ID NO: 18 | MLPA analysis-RPO Probe - PRRT2 exon 2-1 |
| SEQ ID NO: 19 | MLPA analysis-LPO Probe - PRRT2 exon 2-2 |
| SEQ ID NO: 20 | MLPA analysis-RPO Probe - PRRT2 exon 2-2 |
| SEQ ID NO: 21 | MLPA analysis-LPO Probe - PRRT2 exon 2-3 |
| SEQ ID NO: 22 | MLPA analysis-RPO Probe - PRRT2 exon 2-3 |
| SEQ ID NO: 23 | MLPA analysis-LPO Probe - PRRT2 exon 3 |
| SEQ ID NO: 24 | MLPA analysis-RPO Probe - PRRT2 exon 3 |
| SEQ ID NO: 25 | MLPA analysis-LPO Probe - PRRT2 exon 4 |
| SEQ ID NO: 26 | MLPA analysis-RPO Probe - PRRT2 exon 4 |

SUMMARY OF THE INVENTION

The present invention is predicated in part on the identification of a causative gene for both seizure disorders and movement disorders. The inventors have identified mutations in the praline-rich transmembrane protein 2 (PRRT2) gene in individuals with benign familial infantile epilepsy and in individuals with infantile convulsions and choreoathetosis (ICCA) syndrome. This enables methods for the diagnosis or prognosis of seizure and movement disorders, and enables screening methods based on PRRT2 for the identification of potential new therapeutic agents for the treatment of these disorders.

Accordingly, in a first aspect the present invention provides a method for the diagnosis or prognosis of a seizure and/or movement disorder in a subject, the method including testing for the presence of an alteration in the praline rich transmembrane protein 2 (PRRT2) gene in the subject.

In one embodiment, the presence of an alteration in the PRRT2 gene in the subject establishes a diagnosis or prognosis which will indicate a high probability of the disorder in the subject. In one embodiment, the presence of an alteration in the PRRT2 gene in the subject which is also present in an affected parent or relative of the subject, establishes a diagnosis or prognosis which will indicate a very high probability of the disorder in the subject.

In a second aspect, the present invention provides a method for identifying a subject with an increased likelihood of having an offspring predisposed to a seizure and/or movement disorder, the method including testing for the presence of an alteration in the PRRT2 gene in the subject.

In one embodiment, the presence of an alteration in the PRRT2 gene in the subject identifies the subject as a subject with an increased likelihood of having an offspring predisposed to a seizure and/or movement disorder. In one embodiment, the presence of an alteration in the PRRT2 gene in the subject which is also present in an affected parent or relative of the subject identifies the subject as a subject with very high likelihood of having an offspring predisposed to a seizure and/or movement disorder.

In some embodiments of the first and second aspects of the invention, the seizure disorder is epilepsy. In one embodiment, the epilepsy is benign familial infantile epilepsy (BFIE). In some embodiments, the seizure disorder is infantile convulsions and choreoathetosis (ICCA) syndrome. In some embodiments, the movement disorder is paroxysmal kinesigenic choreoathetosis (PKC).

In some embodiments of the first and second aspects of the invention the method includes performing one or more assays to test for the presence of an alteration in the PRRT2 gene and to identify the nature of the alteration.

In some embodiments of the first and second aspects of the invention the method includes: (1) performing one or more assays to test for the presence of an alteration in the PRRT2gene; and, if the results indicate the presence of an alteration in the PRRT2 gene, (2) performing one or more assays to identify the nature of the PRRT2 alteration.

In some embodiments, the one or more assays are selected from the group consisting of DNA sequencing, DNA hybridisation, high performance liquid chromatography, an electrophoretic assay. SSCP analysis, RNase protection, DGGE, an enzymatic assay, MLPA, and an immunoassay.

In some embodiments of the first and second aspects of the invention the PRRT2 alteration is a frameshift mutation in PRRT2. In one embodiment, the frameshift mutation is in exon 2 of PRRT2.

In some embodiments, the frameshift mutation is the result of an insertion of a cytosine (C) nucleotide residue after the nucleotide residue at position 629 of the coding sequence of the PRRT2 gene (c.629-630insC), said coding sequence of the PRRT2 gene set forth in SEQ ID NO: 9 and represented in GenBank Accession No. NM_145239.2. In one embodiment, the coding sequence of PRRT2 comprising the frameshift mutation is set forth in SEQ ID NO: 1. In one embodiment, the frameshift mutation encodes a truncated PRRT2 polypeptide (p.P210fsX224) comprising the amino acid sequence set forth in SEQ ID NO: 2.

In some embodiments, the frameshift mutation is the result of an insertion of a cytosine (C) nucleotide residue after the nucleotide residue at position 649 of the coding sequence of the PRRT2 gene (c.649-650insC), said coding sequence of the PRRT2 gene set forth in SEQ ID NO: 9 and represented in GenBank Accession No. NM_145239.2. In one embodiment, the coding sequence of PRRT2 comprising the frameshift mutation is set forth in SEQ ID NO: 3. In one embodiment, the frameshift mutation encodes a truncated PRRT2 polypeptide (p.R217fsX224) comprising the amino acid sequence set forth in SEQ ID NO: 4.

In some embodiments of the first and second aspects of the invention the PRRT2 alteration is a splice site mutation. In one embodiment, the splice site mutation occurs in intron 2 of PRRT2.

In some embodiments, the splice site mutation is the result of a guanine (G) to thymine (T) nucleotide substitution at position +1 of intron 2 of PRRT2 (IVS2+1G>T), wherein the nucleotide sequence of intron 2 is represented in SEQ ID NO: 11. In one embodiment, the nucleotide sequence of PRRT2 comprising the splice site mutation is set forth in SEQ ID NO: 5.

In some embodiments, the splice site mutation is the result of a guanine (G) to adenine (A) nucleotide substitution at position +5 of intron 2 of PRRT2 (IVS2+5G>A), wherein the nucleotide sequence of intron 2 is represented in SEQ ID NO: 11. In one embodiment, the nucleotide sequence of PRRT2 comprising the splice site mutation is set forth in SEQ ID NO: 6.

In some embodiments of the first and second aspects of the invention the PRRT2 alteration is a missense mutation. In one embodiment, the missense mutation occurs in exon 3 of PRRT2.

In some embodiments, the mutation is the result of a guanine (G) to adenine (A) nucleotide substitution at position 950 of the coding sequence of the PRRT2 gene (c.950G>A), said coding sequence of the PRRT2 gene set forth in SEQ ID NO: 9 and represented in GenBank Accession No. NM_145239.2. In one embodiment, the coding sequence of PRRT2 comprising the missense mutation is set forth in SEQ ID NO: 7. In one embodiment, the missense mutation encodes a PRRT2 polypeptide comprising a serine (S) to asparagine (N) amino acid substitution at amino acid position 317 (p.S317N), said polypeptide comprising the amino acid sequence set forth in SEQ ID NO: 8.

In a third aspect, the present invention provides an isolated nucleic acid molecule comprising an alteration in the PRRT2 gene, wherein said alteration produces a seizure and/or movement disorder phenotype.

In one embodiment, the alteration is a frameshift mutation in PRRT2. In one embodiment, the frameshift mutation is in exon 2 of PRRT2. In some embodiments, the nucleic acid molecule comprises the sequence set forth in SEQ ID NO: 1. In one embodiment, the nucleic acid molecule encodes a PRRT2 polypeptide comprising the amino acid sequence set forth in SEQ ID NO: 2. In some embodiments, the nucleic acid molecule comprises the sequence set forth in SEQ ID NO: 3. In one embodiment, the nucleic acid molecule encodes a PRRT2 polypeptide comprising the amino acid sequence set forth in SEQ ID NO: 4.

In one embodiment of the third aspect of the invention, the alteration is a splice site mutation in PRRT2. In one embodiment, the splice site mutation occurs in intron 2 of PRRT2. In some embodiments, the nucleic acid molecule comprises the sequence set forth in SEQ ID NO: 5 or SEQ ID NO: 6.

In one embodiment of the third aspect of the invention, the alteration is a missense mutation in PRRT2. In one embodiment, the missense mutation occurs in exon 3 of PRRT2. In one embodiment, the nucleic acid molecule comprises the sequence set forth in SEQ ID NO: 7. In one embodiment, the nucleic acid molecule encodes a PRRT2 polypeptide comprising the amino acid sequence set forth in SEQ ID NO: 8.

In some embodiments of the third aspect of the invention, the seizure disorder is epilepsy. In one embodiment, the epilepsy is benign familial infantile epilepsy (BFIE). In some embodiments, the seizure disorder is infantile convulsions and choreoathetosis (ICCA) syndrome. In some embodiments, the movement disorder is paroxysmal kinesigenic choreoathetosis (PKC).

In a fourth aspect, the present invention provides an isolated nucleic acid molecule comprising a fragment of the PRRT2 gene, wherein said nucleic acid molecule includes a mutation in PRRT2, said mutation selected from the group consisting of c.629-630insC, c.649-650insC, IVS2+1G>T, IVS245G>A, and c.950G>A.

In one embodiment, the nucleic acid molecule comprises a nucleotide sequence at least 95% identical to at least about 20 contiguous nucleotides of SEQ ID NO: 1 and includes the c.629-630insC mutation. In one embodiment, the nucleic acid molecule comprises a nucleotide sequence at least 95% identical to at least about 20 contiguous nucleotides of SEQ ID NO: 3 and includes the c.649-650insC mutation. In one embodiment, the nucleic acid molecule comprises a nucleotide sequence at least 95% identical to at least about 20 contiguous nucleotides of SEQ ID NO: 5 and includes the IVS2+1G>T mutation. In one embodiment, the nucleic acid molecule comprises a nucleotide sequence at least 95% identical to at least about 20 contiguous nucleotides of SEQ ID NO: 6 and includes the IVS2+5G>A mutation. In one embodiment, the nucleic acid molecule comprises a nucleotide sequence at least 95% identical to at least about 20 contiguous nucleotides of SEQ ID NO: 7 and includes the c.950G>A mutation.

In a fifth aspect, the present invention provides an isolated polypeptide, wherein said polypeptide is a PRRT2 polypeptide comprising an alteration, wherein said alteration produces a seizure and/or movement disorder phenotype. In one embodiment, the alteration is a truncation mutation. In some embodiments, the polypeptide comprises the amino acid sequence set forth in SEQ ID NO: 2 or SEQ ID NO: 4. In one embodiment, the alteration is an amino acid substitution mutation. In one embodiment, the polypeptide comprises the amino acid sequence set forth in SEQ ID NO: 8.

In some embodiments of the fifth aspect of the invention, the seizure disorder is epilepsy. In one embodiment, the epilepsy is benign familial infantile epilepsy (BFIE). In some embodiments, the seizure disorder is infantile convulsions and choreoathetosis (ICCA) syndrome. In some embodiments, the movement disorder is paroxysmal kinesigenic choreoathetosis (PKC).

In a sixth aspect, the present invention provides an isolated polypeptide comprising a fragment of the PRRT2 polypeptide, wherein said polypeptide includes a mutation in PRRT2, said mutation selected from the group consisting of a truncated PRRT2 polypeptide encoded by an IVS2+1G>T mutation (p.P210fsX224), a truncated PRRT2 polypeptide encoded by an IVS2+5G>A mutation (p.R217fsX224), or S317N.

In one embodiment, the isolated polypeptide comprises an amino acid sequence at least 95% identical to at least about 20 contiguous amino acids of SEQ ID NO: 8 and includes the S317N mutation. In one embodiment, the isolated polypeptide comprises a truncated PRRT2 polypeptide with an amino acid sequence that is at least 95% identical to SEQ ID NO: 2 or SEQ ID NO: 4.

In a seventh aspect, the present invention provides a genetically modified non-human animal comprising a nucleic acid molecule according to a third or fourth aspect of the invention. In one embodiment, the non-human animal is selected from the group consisting of rats, mice, hamsters, guinea pigs, rabbits, dogs, cats, goats, sheep, pigs and non-human primates.

In an eighth aspect, the present invention provides an antibody or fragment thereof which specifically binds to a polypeptide according to a fifth or sixth aspect of the invention.

In a ninth aspect, the present invention provides an antibody or fragment thereof which detects a polypeptide according to a fifth or sixth aspects of the invention, wherein said polypeptide comprises a truncation mutation, and wherein said antibody or fragment thereof binds to the truncated region of said polypeptide.

In a tenth aspect, the present invention provides a kit for diagnosing or prognosing a seizure and/or movement disorder in a subject, or for identifying a subject with an increased likelihood of having an offspring predisposed to a seizure and/or movement disorder, said kit including one or more components for testing for the presence of an alteration in the PRRT2 gene in the subject. In one embodiment, the one or more components are selected from the group consisting of: (i) an antibody or fragment thereof which specifically binds to a polypeptide according to a fifth or sixth aspect of the invention; (ii) an antibody or fragment thereof which detects a polypeptide according to a fifth or sixth aspect of the invention, wherein said polypeptide comprises a truncating mutation, and wherein said antibody or fragment thereof binds to the truncated region of said polypeptide; and (iii) a nucleic acid molecule which specifically hybridises to a nucleic acid molecule according to a third or fourth aspect of the invention.

DETAILED DESCRIPTION OF THE INVENTION

As indicated above, the inventors have identified a gene mutated in seizure and movement disorders. Specifically, through the analysis of affected individuals from families with probable or possible benign familial infantile epilepsy (BFIE), or with infantile convulsions and choreoathetosis (ICCA), the present inventors have identified mutations in the PRRT2 gene that result in, or have the potential to result in, changes to the encoded PRRT2 polypeptide.

Information relating to the PRRT2 gene can be found in the GenBank database of the National Center for Biotechnology Information (www.ncbi.nlm.nih.gov). For example, the Gene ID number for human PRRT2 is 112476, and the content of this GenBank record is incorporated herein by reference. PRRT2 encodes a 340 amino acid proline-rich transmembrane protein of unknown function. Messenger RNA expression data (ensembl) in human tissues shows expression of PRRT2 primarily in the brain, with high expression in the cerebral cortex and cerebellum (GeneNote) which is likely to be related to the clinical expression of BFIE and paroxysmal kinesigenic choreoathetosis (PKC), a manifestation of ICCA. Clues to its biological role come from yeast two hybrid studies demonstrating that PRRT2 interacts with synaptosomal associated protein 25 Da (SNAP25). SNAP25 is a pre-synaptic plasma membrane-bound protein involved in neurotransmitter release from synaptic vesicles. Without wishing to be bound by theory, its binding partner PRRT2 may regulate this process.

The present inventors have identified five different PRRT2 mutations in families with BFIE and in families with ICCA. Furthermore, the inventors have identified de novo mutations in PRRT2 in individuals with sporadic infantile seizures. Collectively, the mutations comprised the following:

two frameshift mutations, namely c.629-630insC, p.P210fsX224 (as represented by SEQ ID NOs: 1 and 2) and c.649-650insC, p.R217fsX224 (as represented by SEQ ID NOs: 3 and 4);

two splice site mutations, namely IVS2+1G>T (as represented by SEQ ID NO: 5) and IVS2+5G>A (as represented by SEQ ID NO: 6) which are each predicted to cause protein truncation (see FIG. 2); and a missense mutation, namely c.950G>A, S317N (as represented by SEQ ID NOs: 7 and 8), which alters an amino acid residue in a transmembrane domain which has been evolutionarily conserved from humans to zebrafish, with the protein only found in vertebrates. In determining the nature of each mutation, sequence comparisons were made to wild-type PRRT2 nucleotide and amino acid sequences. Wild-type PRRT2 nucleotide and amino acid sequences are encompassed in GenBank Accession Numbers NM_145239 and NP_660282, respectively, and are set forth in SEQ ID NOs: 9, 10 and 11 (see Table 1 for an explanation).

Therefore, the present invention enables methods for the diagnosis or prognosis of seizure and movement disorders, such as epilepsy (including BFIE and other neonatal and infantile epilepsies) and ICCA, based on testing for the presence of alterations/mutations in PRRT2, including those identified above.

Accordingly, in a first aspect the present invention provides a method for the diagnosis or prognosis of a seizure and/or movement disorder in a subject, the method including testing for the presence of an alteration in the PRRT2 gene in the subject.

As used herein the word "diagnosis" refers to distinguishing or identifying a disease, disorder or condition or distinguishing or identifying a subject having a particular disease, disorder or condition. The term "prognosis" as used herein refers to a prediction of the probable outcome that an alteration will have with respect to the development of a particular disease, disorder or condition. In this instance, the disease, disorder or condition is a seizure and/or movement disorder.

Whilst the present invention has been described in the context of a human "subject", the invention is not limited so. Therefore, as used herein, the term "subject" should be taken to refer to any animal (e.g., a mammal), including, but not limited to humans, non-human primates, dogs, cats, horses, cattle, sheep, deer, pigs, rodents, and any other animal known to display seizure and/or movement disorders. Therefore, whilst human PRRT2 nucleotide and amino acid sequences have been referred to herein, it should be appreciated that the methods of the present invention are not limited to humans. Details of associated PRRT2 nucleic acid and amino acid sequences for different species may be readily accessed from the GenBank (www.ncbi.nlm.nih.gov) and UniProt (www.uniprot.org) databases. For example, the Gene ID number for mouse PRRT2 is 69017, and the mouse PRRT2 nucleotide and amino acid sequences are encompassed in GenBank Accession Numbers NM_001102563.1 and NP_001096033, respectively.

As used herein, the term "seizure disorder" is taken to mean a disorder which results is an episodic change in behaviour caused by the disordered firing of populations of neurons in the central nervous system. This results in varying degrees of involuntary muscle contraction and often a loss of consciousness. Examples of seizure disorders include, but are not limited to, the epilepsies (including the infantile epilepsies such as benign familial infantile epilepsy—BFIE). The single feature that is common to all epileptic syndromes is the persistent increase in neuronal excitability that is both occasionally and unpredictably expressed as a seizure. The term "movement disorder" as used herein is taken to refer to a neurological condition affecting motor control and muscle tone. Examples of movement disorders include, but are not limited to, dyskinesias (including paroxysmal kinesigenic choreoathetosis (PKC)—also referred to herein as paroxysmal kinesigenic dyskinesia (PKD)), Parkinson's syndrome, dystonias, myoclonus, chorea, tics, and tremor. Some disorders may be classed as constituting both a seizure disorder and a movement disorder. An example includes infantile convulsions and choreoathetosis (ICCA) syndrome.

The terms "alteration" or "mutation" in PRRT2 as used herein are taken to be synonymous. That is, an "alteration" or a "mutation" in PRRT2 is reference to a change in the nucleotide or amino acid sequence of PRRT2 compared to the nucleotide or amino acid sequence of wild-type PRRT2, or to the nucleotide or amino acid sequence of PRRT2 in an individual who does not suffer from a seizure or movement disorder. As indicated above, the nucleotide and amino acid sequences of wild-type human PRRT2, are encompassed in GenBank Accession Numbers NM_145239 and NP_660282, respectively, and are set forth in SEQ ID NOs: 9 and 10, respectively. The genomic DNA encompassing the PRRT2 gene is also set forth in SEQ ID NO: 11 and shown in FIG. 3.

With respect to a change in the nucleotide sequence of PRRT2, the change may not only occur in the nucleotide residues coding for the PRRT2 polypeptide, but may occur in genomic nucleotide sequence which is associated with the coding region. Such genomic nucleotide sequence includes regulatory regions (e.g. promoter regions), introns, untranslated regions and other functional and/or non-functional sequence regions associated with the coding region.

As described in detail below, of the families screened for alterations in the PRRT2 gene, 19 of 24 (79%) families with a seizure disorder (in this case BFIE) that were screened had a mutation in PRRT2, and 10/11 (91%) families with a movement disorder (in this case ICCA) that were screened had a mutation in PRRT2. Accordingly, in one embodiment, the presence of an alteration in the PRRT2 gene establishes a diagnosis or prognosis which will indicate a high probability of the disorder in the subject.

Through the analysis of families with seizure and movement disorders, the present inventors have found that the presence of a particular PRRT2 alteration in a subject is also found in affected relatives of the subject. Accordingly, in some embodiments of the first aspect of the invention, an alteration in the PRRT2 gene in the subject which is also present in an affected parent or relative of the subject, establishes a diagnosis or prognosis which will indicate a very high probability of the disorder in the subject.

Furthermore, the identification of a PRRT2 alteration in a subject that has previously been clinically diagnosed with a probable or possible seizure and/or movement disorder increases the likelihood that the subject has that disorder. Still further, with respect to epilepsy (and in particular BFIE), information concerning the age of onset that may be used to suggest a diagnosis of BFIE or other related familial epilepsy syndrome may be ruled out through failure to identify a PRRT2 alteration. This information is important for initiating the correct treatment regimen for a subject and avoids unnecessary testing and associated trauma to the subject.

The inheritance of mutations in the PRRT2 gene enables the screening of subjects to determine their genetic carrier status. A subject that is a genetic carrier of a disease, disorder or condition is a subject that has inherited a genetic trait or mutation, but who either does not display that trait or show symptoms of the disease, disorder or condition, or has been unaware that they have manifested symptoms of the disease, disorder or condition in the past. The subject is however, able to pass the genetic trait or mutation onto their offspring, who may then develop the disease, disorder or condition. Determining carrier status is useful for example for couples who are contemplating having children.

Accordingly, in a second aspect the present invention provides a method for identifying a subject with an increased likelihood of having an offspring predisposed to a seizure and/or movement disorder, the method including testing for the presence of an alteration in the PRRT2 gene in the subject. It follows that presence of an alteration in the PRRT2 gene in the subject identifies the subject as a subject with an increased likelihood of having an offspring predisposed to a seizure and/or movement disorder. Furthermore, the presence of an alteration in the PRRT2 gene in the subject which is also present in an affected parent or relative of the subject identifies the subject as a subject with very high likelihood of having an offspring predisposed to a seizure and/or movement disorder.

The nature of the alterations in the PRRT2 gene may encompass all forms of gene sequence variations including deletions, insertions, rearrangements and point mutations in the coding and non-coding regions such as the promoter, introns or untranslated regions. Deletions may be of the entire gene or only a portion of the gene, whereas point mutations and insertions may result in the introduction of stop codons, frameshifts or amino acid substitutions. A frameshift in the PRRT2 gene may lead to the translation of a truncated PRRT2 polypeptide, which may or may not be unstable, or may result in little or no translation of PRRT2 protein at all. Point mutations occurring in the regulatory regions of PRRT2, such as in the promoter, may lead to loss or a decrease of expression of PRRT2 mRNA or may abolish proper mRNA processing leading to a decrease in mRNA stability or translation efficiency.

In some embodiments of the aforementioned aspects of the present invention, the method includes performing one or more assays to test for the presence of an alteration in the PRRT2 gene and to identify the nature of the alteration.

In some embodiments, the method includes performing one or more assays to test for the presence of an alteration in the PRRT2 gene; and, if the results indicate the presence of an alteration in the PRRT2 gene, performing one or more assays to identify the nature of the PRRT2 alteration.

In some embodiments, the presence of an alteration in the PRRT2 gene in the subject is determined from an analysis of a biological sample taken from the subject. The term "sample" is meant to include biological samples such as cells (including those present in blood or cheek), tissues (including tissue biopsy, surgical specimen or autopsy material), exosomes, and bodily fluids. "Bodily fluids" may include, but are not limited to, blood, serum, plasma, saliva, cerebral spinal fluid, pleural fluid, tears, lactal duct fluid, lymph, sputum, urine, amniotic fluid, and semen. A sample may include a bodily fluid that is "acellular." An "acellular bodily fluid" includes less than about 1% (w/w) whole cellular material. Plasma or serum is an example of an acellular bodily fluid. In addition, prenatal testing can be accomplished by testing fetal cells, placental cells or amniotic fluid.

In some embodiments, nucleic acid or protein is first isolated from the sample before testing for the presence of an alteration in the PRRT2 gene. The nucleic acid (DNA or RNA) or protein may be isolated from the sample according to any methods well known to those of skill in the art, for example see Sambrook et al. (*Molecular Cloning—A Laboratory Manual*, $3^{rd}$ Ed., Cold Spring Harbor Laboratory Press, 2000).

As would be understood by a person skilled in the art, there exist a number of assay systems that can be used to test for the presence of PRRT2 alterations and to determine the nature of the alterations, and the invention is not limited by the examples that are provided below.

For example, in one embodiment an assay system employed may rely on the analysis of PRRT2 nucleic acid in a sample taken from a subject in comparison to wild-type PRRT2 nucleic acid. In some embodiments, genomic DNA may be used for the analysis and may be obtained from a number of sources as described above. The genomic DNA may be isolated and used directly for an assay or may be amplified by the polymerase chain reaction (PCR) prior to analysis. Similarly, mRNA or cDNA may also be used, with or without PCR amplification.

In one embodiment, a nucleic acid hybridisation assay may be employed. One such assay may look at a series of Southern blots of DNA that has been digested with one or more restriction enzymes. Each blot may contain a series of digested DNA samples from normal individuals and a series of digested DNA samples from one or more subjects being tested. Samples displaying hybridisation fragments that differ in length from normal DNA when probed with sequences near or including the PRRT2 gene will indicate a possible PRRT2 mutation. If restriction enzymes that produce very large restriction fragments are used then pulsed field gel electrophoresis (PFGE) may be employed.

Hybridisation assays that are specific for a PRRT2 gene exon may also be employed. This type of probe-based assay will utilise at least one probe which specifically and selectively hybridises to an exon of the PRRT2 gene in its wild-type form. Thus, the lack of formation of a duplex nucleic acid hybrid containing the nucleic acid probe is indicative of the presence of mutation in the gene. Because of the high specificity of probe-based tests, any negative result is highly indicative of the presence of a mutation however further investigational assays should be employed to identify the nature of the mutation, as set out further below.

Figure 2:
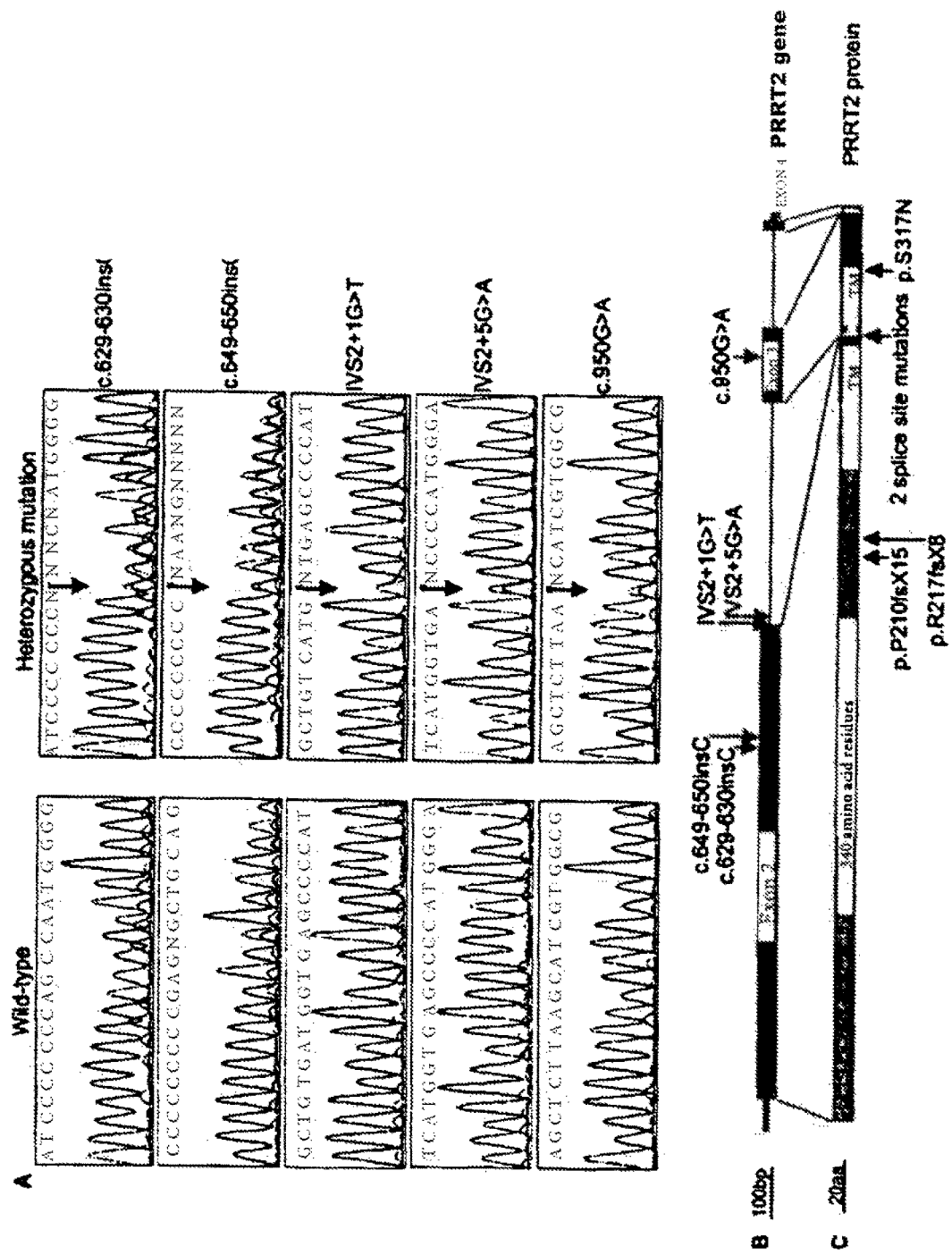
FIG. 2—A: Sequence traces showing the five mutations identified in the 19 BFIE and ICCA families of Example 1. B: Gene structure of the coding exons of PRRT2 (exons 2 to 4), showing the locations of the five mutations in BFIE and ICCA families. C: Structure of the PRRT2 protein, also showing the locations of the five mutations. The transmembrane (TM) domains are indicated in purple. In B and C the frameshift mutations are marked in light blue, the splice site mutations in dark blue and the missense mutation in pink. The lines between B and C indicate which regions of the protein are coded by the PRRT2 coding exons.

A PRRT2 exon specific probe used for the abovementioned assay may be derived from: (1) PCR amplification of each exon of the PRRT2 gene using intron specific primers flanking each exon; (2) cDNA probes specific for each exon; or (3) a series of oligonucleotides that collectively represent an exon under investigation. The genomic structure of the PRRT2 gene is shown in FIG. 2 (with respect to the coding exons—exons 2 to 4) and the nucleotide sequence of each exon and intron of PRRT2 is shown in FIG. 3 and SEQ ID NO: 11.

In a further embodiment, an assay to analyse heteroduplex formation may be employed. By mixing denatured wild-type PRRT2 DNA with a DNA sample from a subject, any change in the PRRT2 sequence between the two samples will lead to the formation of a mixed population of heteroduplexes and homoduplexes during reannealing of the DNA. Analysis of this mixed population can be achieved through the use of such techniques as high performance liquid chromatography (HPLC), which is performed under partially denaturing temperatures. In this manner, heteroduplexes will elute from the HPLC column earlier than the homoduplexes because of their reduced melting temperature.

In a further embodiment, patient nucleic acid samples may be subject to electrophoretic-based assays. For example electrophoretic assays that determine PRRT2 fragment length differences may be employed. Fragments of genomic DNA from a subject to be tested are amplified with PRRT2 gene intron specific primers. The amplified regions of the gene therefore include the exon of interest, the splice site junction at the exon/intron boundaries, and a short portion of intron at either end of the amplification product. The amplification products may be run on an electrophoresis size-separation gel and the lengths of the amplified fragments are compared to known and expected standard lengths from the wild-type gene to determine if an insertion or deletion mutation is found in the patient sample. This procedure can advantageously be used in a "multiplexed" format, in which primers for a plurality of exons are co-amplified, and evaluated simultaneously on a single electrophoretic gel. This is made possible by careful selection of the primers for each exon. The amplified fragments spanning each exon are designed to be of different sizes and therefore distinguishable on an electrophoresis/size separation gel. The use of this technique has the advantage of detecting both normal and mutant alleles in heterozygous individuals.

Additional electrophoretic assays may be employed. These may include the single-stranded conformational polymorphism (SSCP) procedure (Orita et al., 1989, *Proc. Natl. Acad. Sci. USA*, 86: 2766-70). As mentioned above, fragments of subject genomic DNA are PCR amplified with PRRT2 gene intron specific primers such that individual exons of the gene are amplified and may be analysed individually. Exon-specific PCR products are then subjected to electrophoresis on non-denaturing polyacrylamide gels such that DNA fragments migrate through the gel based on their conformation as dictated by their sequence composition. Exon-specific fragments that vary in sequence from wild-type sequence will have a different secondary structure conformation and therefore migrate differently through the gel. Aberrantly migrating PCR products in patient samples are indicative of an alteration in the exon and should be analysed further in assays such as DNA sequencing to identify the nature of the alteration.

Additional electrophoretic assays that may be employed include RNase protection assays (Finkelstein et al., 1990, *Genomics* 7: 167-172; Kinszler et al., 1991, *Science* 251: 1366-1370) and denaturing gradient gel electrophoresis (DGGE) (Wartell et al., 1990, *Nucleic Acids Res.* 18: 2699-2705; Sheffield et al., 1989, *Proc. Natl. Acad. Sci. USA* 86: 232-236). RNase protection involves cleavage of a mutant polynucleotide into two or more smaller fragments whereas DGGE detects differences in migration rates of mutant sequences compared to wild-type sequences, using a denaturing gradient gel.

In the RNase protection assay a labelled riboprobe which is complementary to the wild-type PRRT2 gene coding sequence is hybridised with either mRNA or DNA isolated from the patient and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene under investigation but can be a segment of either. If the riboprobe comprises only a segment of the mRNA or gene, it will be desirable to use a number of these probes to screen the whole mRNA sequence for mismatches.

In a further embodiment, enzymatic based assays may be used in the methods of the invention. Such assays include the use of Si nuclease, ribonuclease, T4 endonuclease VII, MutS (Modrich, 1991, *Ann. Rev. Genet.* 25: 229-253), Cleavase and MutY. In the MutS assay, the protein binds only to sequences that contain a nucleotide mismatch in a heteroduplex between mutant and wild-type sequences.

In instances where a seizure or movement disorder is associated with abnormal expression of the PRRT2 gene, alternative assays are required. Firstly, a normal or standard profile for PRRT2 expression is established. This may be accomplished by combining body fluids or cell extracts taken from normal subjects, with a sequence, or a fragment thereof, encoding the PRRT2 gene, under conditions suitable for hybridisation or amplification. Standard hybridisation may be quantified by comparing the values obtained from normal subjects with values from an experiment in which a known amount of a substantially purified polynucleotide is used. Another method to identify a normal or standard profile for expression is through quantitative RT-PCR studies. RNA isolated from body cells of a normal subject is reverse transcribed and real-time PCR using oligonucleotides specific for PRRT2 is conducted to establish a normal level of expression of the gene. Standard values obtained in both these examples may be compared with values obtained from samples from patients who are symptomatic for the disorder. Deviation from standard values is used to establish the presence of the disorder.

Methods for measuring the expression level of a gene are generally known in the art. Techniques may include, but are not limited to, Northern blotting, RNA in situ hybridisation, reverse-transcriptase PCR (RT-PCR), real-time (quantitative) RT-PCR, microarrays, or "tag based" technologies such as SAGE (serial analysis of gene expression). Microarrays and SAGE may be used to simultaneously quantitate the expression of more than one gene. Primers or probes may be designed based on nucleotide sequence of the PRRT2 gene. Methodology similar to that disclosed in Paik et al., 2004 (*NEJM* 351(27): 2817-2826) or Anderson et al., 2010 (*J. Mol. Diagnostics* 12(5): 566-575) may be used to measure the expression of the PRRT2 gene. Many methods are also disclosed in standard molecular biology text books such as Sambrook et al. (*Molecular Cloning—A Laboratory Manual*, 3$^{rd}$ Ed., Cold Spring Harbor Laboratory Press, 2000).

With respect to RT-PCR, the first step is typically the isolation of total RNA from a sample obtained from the subject under investigation. Messenger RNA (mRNA) may be subsequently purified from the total RNA sample. The total RNA sample (or purified mRNA) is then reverse transcribed into cDNA using a suitable reverse transcriptase. The reverse transcription step is typically primed using oligo-dT primers, random hexamers, or primers specific for the PRRT2 gene, depending on the RNA template. The cDNA derived from the reverse transcription reaction then serves as a template for a typical PCR reaction. In this regard, two oligonucleotide PCR primers specific for the PRRT2 gene are used to generate a PCR product. A third oligonucleotide, or probe, designed to detect a nucleotide sequence located between the other two PCR primers is also used in the PCR reaction. The probe is non-extendible by the Taq DNA polymerase enzyme used in the PCR reaction, and is labelled with a reporter fluorescent dye and a quencher fluorescent dye. Any laser-induced emission from the reporter dye is quenched by the quenching dye when the two dyes are located close together, as they are on the probe. During the PCR amplification reaction, the Taq DNA polymerase enzyme cleaves the probe in a template-dependent manner. The resultant probe fragments disassociate in solution, and signal from the released reporter dye is freed from the quenching effect of the second fluorophore. One molecule of reporter dye is liberated for each new molecule synthesized, and detection of the unquenched reporter dye provides the basis for quantitative interpretation of the data.

In real-time RT-PCR the amount of product formed, and the timing at which the product is formed, in the PCR reaction correlates with the amount of starting template. RT-PCR product will accumulate quicker in a sample having an increased level of mRNA compared to a standard or "normal" sample. Real-time RT-PCR measures either the fluorescence of DNA intercalating dyes such as Sybr Green into the synthesized PCR product, or can measure PCR product accumulation through a dual-labelled fluorigenic probe (i.e. TaqMan probe). The progression of the RT-PCR reaction can be monitored using PCR machines such as the Applied Biosystems' Prism 7000 or the Roche LightCycler which measure product accumulation in real-time. Real-time RT-PCR is compatible both with quantitative competitive PCR and with quantitative comparative PCR. The former uses an internal competitor for each target sequence for normalization, while the latter uses a normalization gene contained within the sample, or a housekeeping gene for RT-PCR.

The production and application of microarrays for measuring the level of expression of the PRRT2 gene may be used and are well known in the art. In general, in a microarray, a nucleotide sequence (for example an oligonucleotide, a cDNA, or genomic DNA) representing a portion, or all, of the PRRT2 gene occupies a known location on a substrate. A nucleic acid target sample (for example total RNA or mRNA) obtained from a subject of interest is then hybridized to the microarray and the amount of target nucleic acid hybridized to each probe on the array is quantified and compared to the hybridisation which occurs to a standard or "normal" sample. One exemplary quantifying method is to use confocal microscope and fluorescent labels. The Affymetrix GeneChip™ Array system (Affymetrix, Santa Clara, Calif.) and the Atlas™ Human cDNA Expression Array system are particularly suitable for quantifying the hybridization; however, it will be apparent to those of skill in the art that any similar systems or other effectively equivalent detection methods can also be used.

Fluorescently labelled cDNA probes may also represent the nucleic acid target sample. Such probes can be generated through incorporation of fluorescent nucleotides during reverse transcription of total RNA or mRNA extracted from a sample of the subject to be tested. Labelled cDNA probes applied to the microarray will hybridize with specificity to the equivalent spot of DNA on the array. Quantitation of hybridization of each arrayed element allows for assessment of corresponding mRNA abundance in the sample compared to the abundance observed in a standard or "normal" sample. With dual colour fluorescence, separately labelled cDNA probes generated from two sources of RNA are hybridized pairwise to the array. The relative abundance of the transcripts from the two sources corresponding to the PRRT2 gene is thus determined simultaneously. Such methods have been shown to have the sensitivity required to detect at least approximately two-fold differences in the expression levels.

Another assay which may be used to identify an alteration in the PRRT2 gene is the Multiplex Ligation-Dependent Probe Amplification (MLPA) assay. MLPA is a variation of multiplex polymerase chain reactions that permit multiple targets to be amplified with only a single primer pair. Each probe used in the assay consists of two oligonucleotides which recognise adjacent target sites on the PRRT2 DNA. When the probe oligonucleotides correctly hybridize to the target sequence they are ligated by a thermo-stable ligase to form a complete probe. The advantage of splitting the probe into two parts is that only the ligated oligonucleotides, but not the unbound probe oligonucleotides, are amplified during the PCR reaction. Each complete probe has a unique length, so that its resulting amplicons can be separated and identified by capillary electrophoresis. This avoids the resolution limitations of multiplex PCR. Given that one of the probe oligonucleotides is labeled with a fluorescent dye, each amplicon generates a fluorescent peak which can be detected by a capillary sequencer. A difference in the peak pattern obtained on a given sample with that obtained for a reference sample (for example a sample from a wild-type PRRT2 gene), will indicate the presence of an alteration in the complete probe (i.e. an alteration in the PRRT2 gene).

The most definitive assay to identify the presence of an alteration in the PRRT2 gene, and/or to identify the nature of the mutation is DNA sequencing. Comparison of the wild-type nucleotide sequence of PRRT2 with the PRRT2 nucleotide sequence from a subject to be tested provides both high specificity and high sensitivity. The general methodology employed involves amplifying (for example with PCR) DNA fragments of the PRRT2 gene from subject DNA as described above; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained. While such methods, which are based on the original dideoxysequencing method disclosed by Sanger et al., 1977 (*Proc. Natl. Acad. Sci. USA* 74: 5463-5467) are useful in the present invention, the final assay is not limited to such methods. For example, other methods for determining the sequence of the PRRT2 gene may also be employed. Alternative methods include those described by Maxam and Gilbert, 1977 (*Proc. Natl. Acad. Sci. USA* 74: 560-564) and variations of the dideoxy method and methods which do not rely on chain-terminating nucleotides at all such as that disclosed in U.S. Pat. No. 4,971,903, which is incorporated herein by reference. Other alternative methods include Pyrosequencing (Pyrosequencing, Westborough, Mass.), protocols for which can be found in Alderborn et al., 2000 (*Genome Res.* 10: 1249-1265). Sequencing by dideoxy chain termination method can be performed using Thermo Sequenase (Amersham Pharmacia, Piscataway, N.J.), Sequenase reagents from US Biochemicals or Sequatherm sequencing kit (Epicenter Technologies, Madison, Wis.). Sequencing may also be carried out by the "RR dRhodamine Terminator Cycle Sequencing Kit" from PE Applied Biosystems (product no. 403044, Weiterstadt, Germany), Taq DyeDeoxy™ Terminator Cycle Sequencing kit and method (Perkin-Elmer/Applied Biosystems) in two directions using an Applied Biosystems Model 373 A DNA or in the presence of dye terminators CEQ™ Dye Terminator Cycle Sequencing Kit, (Beckman 608000). Any sequence differences (other than benign polymorphisms) in exons of a test subject when compared to that of the wild-type sequence indicate a potential disease-causing mutation.

In one embodiment an assay system employed may be the analysis of PRRT2 polypeptide obtained from a subject protein sample in comparison to wild-type PRRT2 polypeptide. For example, any differences in the electrophoretic mobility of a mutant PRRT2 polypeptide compared to wild-type PRRT2 can be exploited as the basis for identifying a mutated PRRT2 polypeptide. Such an approach will be particularly useful in identifying mutants in which charge substitutions are present, or in which insertions, deletions, truncations or substitutions have resulted in a significant change in the electrophoretic migration of the resultant protein. Antibodies (or fragments thereof) may also be useful in identifying mutant PRRT2 polypeptide, particularly if the antibody (or fragment thereof) can specifically hybridise to the mutant PRRT2 polypeptide and not to the wild-type PRRT2 polypeptide. Alternatively, an antibody (or fragment thereof) which detects the presence of a truncated PRRT2 polypeptide may be one that binds to the truncated region so that it in effect only recognises and binds to the wild-type PRRT2 polypeptide. In other embodiments, differences in the proteolytic cleavage patterns of normal and mutant PRRT2 polypeptide may be determined, or differences in molar ratios of the various amino acid residues may be determined. Amino acid sequence determination may also be used to compare a PRRT2 polypeptide obtained from a subject sample to wild-type PRRT2 polypeptide.

As indicated above, the inventors have identified 5 specific mutations in the PRRT2 gene that are causative for seizure and movement disorders (BFIE and ICCA). These include two frameshift mutations in exon 2 (c.629-630insC and c.649-650insC), two splice site mutations (IVS2+1G>T and IVS2+5G>A), and one missense mutation (c.950G>A). Accordingly, in one embodiment of the first and second aspects of the invention, these specific mutations may form the basis of assays which test for the presence of only these mutations in subjects. For example, the c.649-650insC mutation has been found to be present in a large number of affected individuals from different families, wherein these individuals are not suspected to be related. The c.649-650insC mutation may therefore be one example of a PRRT2 mutation which is tested for in the wider population or as a primary first-pass mutation screen in subjects being tested.

The assays referred to above may be used to test for the presence of these five mutations in subjects. However, additional assays may also be employed given that the nature of the mutation is known. Assays which are based on a known PRRT2 mutation include those which utilise allele-specific primers and probes, for example PCR-based approaches that use oligonucleotide primers which specifically bind to the PRRT2 mutation being tested for. Such oligonucleotides which detect single nucleotide variations in target sequences may be referred to by such terms as "allele-specific probes", or "allele-specific primers". The design and use of allele-specific probes for detecting known sequence variations (in this instance in PRRT2) is described in, for example, Mutation Detection A Practical Approach, ed. Cotton et a. Oxford University Press, 1998; Saiki et al., 1986 (*Nature,* 324: 163-166); EP235726; and WO 89/11548. In one example, a probe or primer may be designed to hybridize to a segment of PRRT2 target DNA such that the mutation site in PRRT2 aligns with either the 5' most end or the 3' most end of the probe or primer. In some assays, the amplification may include a labeled primer, thereby allowing detection of the amplification product of that primer. In one example, the amplification may include a multiplicity of labeled primers; typically, such primers are distinguishably labeled, allowing the simultaneous detection of multiple amplification products.

In one type of PCR-based assay, an allele-specific primer hybridizes to a region on a target PRRT2 nucleic acid molecule that overlaps with the mutation site (e.g. c.629-630insC, c.649-650insC, IVS2+1G>T, IVS2+5G>A and c.950G>A) and only primes amplification of an allelic form to which the primer exhibits perfect complementarity (Gibbs, 1989, *Nucleic Acid Res.* 17:2427-2448). Typically, the primer's 3'-most nucleotide is aligned with and complementary to the mutation site of the target nucleic acid molecule. This primer is used in conjunction with a second primer that hybridizes at a distal site. Amplification proceeds from the two primers, producing a detectable product that indicates which allelic form is present in the test sample. A control is usually performed with a second pair of primers, one of which shows a single base mismatch at the mutation site and the other of which exhibits perfect complementarity to a distal site. The single-base mismatch prevents amplification or substantially reduces amplification efficiency, so that either no detectable product is formed or it is formed in lower amounts or at a slower pace. The method generally works most effectively when the mismatch is at the 3'-most position of the oligonucleotide (i.e. the 3'-most position of the oligonucleotide aligns with the target mutation position) because this position is most destabilizing to elongation from the primer (see for example WO 93/22456). A person skilled in the art would readily be able to design allele-specific primer sequences for detecting the c.629-630insC, c.649-650insC, IVS2+1G>T, IVS2+5G>A and c.950G>A PRRT2 mutations referred to above, or any other PRRT2 mutation identified in the future.

In one example, a primer contains a sequence substantially complementary to a segment of a mutation-containing target nucleic acid molecule except that the primer has a mismatched nucleotide in one of the three nucleotide positions at the 3'-most end of the primer, such that the mismatched nucleotide does not base pair with a particular allele at the mutation site. The mismatched nucleotide in the primer can be the first, second or the third nucleotide from the last nucleotide at the 3'-most position of the primer. In some examples, primers and/or probes are labeled with detectable labels.

In an alternative approach, tagged allele specific primer pairs can be used to detect a known mutation in PRRT2 (Strom et al., 2005, *Genet. Med.* 7:633-63). In one example, two tagged allele-specific primers overlap the mutation site in the target DNA; however, only the correctly hybridized primer(s) will be extended to generate a labeled product(s). A non-complementary primer will not be extended or labeled due to the 3' mismatched base. The labeled extended product can be detected based on the detectable label. The tagged extended primers can also be captured on a solid support such as beads that are coupled to anti-tag sequences. The immobilized extended primer product can be detected by commercially available means such as Luminex 100 LabMAP™ (Luminex Corporation, Austin Tex.).

Assays which detect previously identified PRRT2 polypeptide mutations, including those listed herein, are also known in the art. For example, detection of mutant PRRT2 polypeptide in a protein population obtained from a sample of the subject could be by resolution of the proteins by SDS polyacrylamide gel electrophoresis (SDS PAGE), followed by staining the proteins with suitable stain for example, Coomassie Blue. PRRT2 polypeptide with and without a mutation can be differentiated from each other and also from other proteins based on their molecular weight and migration on SDS PAGE.

Detection of the presence of known mutations in a PRRT2 polypeptide can also be accomplished using, for example, antibodies, aptamers, ligands/substrates, other proteins or protein fragments, other protein-binding agents, or mass spectrometry analysis of fragments. Preferably, protein detection agents are specific for a mutated PRRT2 polypeptide and can therefore discriminate between a mutated protein and the wild-type protein or another variant form. This can generally be accomplished by, for example, selecting or designing detection agents that bind to the region of a protein that differs between the variant and wild-type protein.

One preferred agent for detecting a mutated PRRT2 polypeptide is an antibody capable of specifically binding to the mutated PRRT2 polypeptide. Antibodies that are capable of distinguishing between wild-type and mutated PRRT2 polypeptide may be created by any suitable method known in the art (see below). The antibodies may be monoclonal or polyclonal antibodies, single chain or double chain, chimeric or humanized antibodies, or fragments of said antibodies (i.e. portions of immunoglobulin molecules containing the antigen binding regions of PRRT2).

Antibodies, or fragments thereof, useful for detecting the presence of a truncated PRRT2 polypeptide identified by the inventors (i.e. p.P210fsX224 or p.R217fsX224) may be those that recognise and bind to the region of the polypeptide that is deleted (i.e. amino acids 217-340 of PRRT2) so that it in effect they only recognise and bind to the wild-type PRRT2 polypeptide.

In vitro methods for detection of a known PRRT2 polypeptide mutation also include, for example, enzyme linked immunosorbent assays (ELISAs), radioimmunoassays (RIA), Western blots, immunoprecipitations, immunofluorescence, and protein arrays/chips (e.g., arrays of antibodies or aptamers). For further information regarding immunoassays and related protein detection methods, see Current Protocols in Immunology, John Wiley & Sons, N.Y; and Hage, 1999, *Anal. Chem.* 15; 71(12): 294R-304R. Additional methods of detecting amino acid variants include, but are not limited to, altered electrophoretic mobility (e.g., 2-dimensional electrophoresis), altered tryptic peptide digest, altered HEXA activity in cell-based or cell-free assay, alteration in ligand or antibody-binding pattern, and altered isoelectric point.

PRRT2 polypeptide with and without a mutation can be differentiated from each other and from other proteins by Western blot analysis. Methods of Western blot are well known in the art and are described for example in Burnette, 1981 (*Anal. Biochem.* 112 (2): 195-203). Briefly, protein is extracted from a sample obtained from a subject using standard techniques and is then subjected to SDS PAGE. The protein sample will include PRRT2 polypeptide. Following gel electrophoresis, proteins in the protein sample are transferred to a nitrocellulose or polyvinylidene fluoride (PVDF) membrane. The membrane is blocked with a suitable blocking agent to prevent subsequent non-specific binding of antibody to the membrane. Suitable blocking agents include bovine serum albumin and non-fat dry milk. After blocking and several washes with a suitable buffer, antibodies that specifically bind to the PRRT2 mutation being tested, antibodies that recognise and bind to a region of the PRRT2 polypeptide that is deleted, and/or antibodies that specifically bind to wild-type PRRT2 are allowed to bind to the protein sample of interest that has been transferred to the membrane. Following the binding of primary antibody to the membrane, excess antibodies are washed away with a suitable buffer. A suitable secondary antibody that is able to bind to the primary antibody is then applied, the secondary antibody being detectably labeled. Excess secondary antibody is then washed away with a suitable buffer and the detectable label of the secondary antibody is detected. Detection of the detectable label of the secondary antibody indicates the presence of the protein of interest—mutant or wild-type. If primary antibodies specific for a particular mutant PRRT2 polypeptide are used, then the mutant polypeptide is identified.

A variety of additional assays for measuring the presence of a mutant PRRT2 polypeptide can also be used. Such assays include dissociation-enhanced lanthanide fluoro immuno assay (DELFIA)), proteomics techniques, surface plasmon resonance, chemiluminescence, fluorescent polarization, phosphorescence, immunohistochemistry, matrix-assisted laser desorption/ionization mass spectrometry (MALDI-MS), as described in WO 2009/004576 (including surface enhanced laser desorption/ionization mass spectrometry (SELDI-MS), especially surface-enhanced affinity capture (SEAC), surface-enhanced need desorption (SEND) or surface-enhanced photo label attachment and release (SEPAR)), matrix-assisted laser desorptionfionization time-of-flight (MALDI-TOF) mass spectrometry, microcytometry, microarray, microscopy, fluorescence activated cell sorting (FACS), and flow cytometry.

On the basis of the range of assays available to test for mutations in PRRT2, in a further embodiment there is provided a method for testing a subject for a seizure or movement disorder-associated mutation, such as aBFIE- or ICCA-associated mutation, in the PRRT2 gene including the steps of:

(1) quantitatively amplifying, from a sample obtained from the subject, at least one exon of the PRRT2 gene using primers complementary to intron regions flanking each amplified exon;

(2) comparing the length of the amplification products for each amplified exon to the length of the amplification products obtained when a wild-type PRRT2 gene is amplified using the same primers, wherein differences in length between an amplified sample exon and the corresponding amplified wild-type exon reflect the occurrence of a truncating mutation in the sample PRRT2gene.

In one embodiment, the method further includes determining the nucleic acid sequence of the truncating mutation.

In further embodiment there is provided a method for testing a subject for a seizure or movement disorder-associated mutation, such as a BFIE- or ICCA-associated mutation, in the PRRT2 gene including the steps of:

(1) quantitatively amplifying, from a sample obtained from the subject, at least one exon of the PRRT2 gene using primers complementary to intron regions flanking each amplified exon;

(2) hybridising the fragments from (1) with fragments produced by amplification of the same exon in a wild-type PRRT2 gene, wherein an amplified exon from the subject that either does not hybridise to a corresponding wild-type fragment or forms a mismatched heteroduplex therewith reflects the occurrence of a mutation in the amplified exon.

In one embodiment, the method further includes determining the nucleic acid sequence of the mutated exon.

As indicated above, the present inventors have determined that the PRRT2 gene is associated with seizure and movement disorders, including BFIE and ICCA, through the identification of mutations in the PRRT2 gene.

Accordingly, in a third aspect the present provides an isolated nucleic acid molecule comprising an alteration in the PRRT2 gene, wherein said alteration produces a seizure and/or movement disorder phenotype. In some embodiments, the alteration is a frameshift mutation, a splice site mutation or a missense mutation. For example, in some embodiments the mutation may be one of c.629-630insC, c.649-650insC, IVS2+1G>T, IVS2+5G>A and c.950G>A, as described in detail above. In this regard, the nucleic acid molecule comprises the sequence set forth in one of SEQ ID NOs: 1, 3, 5, 6 and 7.

The present invention also contemplates a nucleic acid fragment of SEQ ID NOs: 1, 3, 5, 6 and 7, provided the fragment includes the relevant mutation. A nucleic acid fragment may comprise at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% nucleotide sequence identity to one of SEQ ID NOs: 1, 3, 5, 6 and 7, and contains the relevant mutation. The nucleic acid fragment may be of any length provided it includes at least about 20 contiguous nucleotides of one of SEQ ID NOs: 1, 3, 5, 6 and 7.

Accordingly, in a fourth aspect the present invention provides an isolated nucleic acid molecule comprising a fragment of the PRRT2 gene, wherein said nucleic acid molecule includes a mutation in PRRT2, said mutation selected from the group consisting of c.629-630insC, c.649-650insC, IVS2+1G>T, IVS2+5G>A, and c.950G>A.

In some embodiments, the nucleic acid molecule comprises: (1) a nucleotide sequence at least 95% identical to at least about 20 contiguous nucleotides of SEQ ID NO: 1 and includes the c.629-630insC mutation; (2) a nucleotide sequence at least 95% identical to at least about 20 contiguous nucleotides of SEQ ID NO: 3 and includes the c.649-650insC mutation; (3) a nucleotide sequence at least 95% identical to at least about 20 contiguous nucleotides of SEQ ID NO: 5 and includes the IVS2+1G>T mutation; (4) a nucleotide sequence at least 95% identical to at least about 20 contiguous nucleotides of SEQ ID NO: 6 and includes the IVS2+5G>A mutation; or (5) a nucleotide sequence at least 95% identical to at least about 20 contiguous nucleotides of SEQ ID NO: 7 and includes the c.950G>A mutation.

Any one or more of these PRRT2 fragments may be used in the aforementioned assays for testing for the presence of the alteration in the PRRT2 gene of a subject under investigation.

In a fifth aspect, the present invention provides an isolated polypeptide, wherein said polypeptide is a PRRT2 polypeptide comprising an alteration, wherein said alteration produces a seizure and/or movement disorder phenotype. In some embodiments, the alteration is a truncation mutation or an amino acid substitution mutation. For example, in some embodiments the mutation may be one of p.P210fsX224, p.R217fsX224 and p.S317N, as described in detail above. In this regard, the polypeptide comprises the sequence set forth in one of SEQ ID NOs: 2, 4 and 8.

The present invention also contemplates a polypeptide fragment of SEQ ID NOs: 2, 4 and 8, provided the fragment includes the relevant mutation. A polypeptide fragment may comprise at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100% amino acid sequence identity to one of SEQ ID NOs: 2, 4 and 8, and contains the relevant mutation. The polypeptide fragment may be of any length provided it includes at least about 20 contiguous amino acid residues of one of SEQ ID NOs: 2, 4 and 8.

Accordingly, in a sixth aspect the present invention provides an isolated polypeptide comprising a fragment of the PRRT2 polypeptide, wherein said polypeptide comprises a mutation in PRRT2, said mutation selected from the group consisting of a truncated PRRT2 polypeptide encoded by an IVS2+1G>T mutation (p.P210fsX224), a truncated PRRT2 polypeptide encoded by an IVS2+5G>A mutation (p.R217fsX224), or S317N.

In some embodiments, the polypeptide comprises: (1) an amino acid sequence at least 95% identical to at least about 20 contiguous amino acids of SEQ ID NO: 8 and includes the S317N mutation; and (2) a truncated PRRT2 polypeptide with an amino acid sequence that is at least 95% identical to SEQ ID NO: 2 or SEQ ID NO: 4.

The present invention also provides for the production of genetically modified (knock-out, knock-in and transgenic), non-human animal models comprising the nucleic acid molecules of the invention. Accordingly, in a seventh aspect the present invention provides a genetically modified non-human animal comprising a nucleic acid molecule according to the third or fourth aspects of the invention.

Genetically modified animals are useful for the study of PRRT2 gene function, to study the mechanisms by which the PRRT2 mutations of the invention give rise to seizure and movement disorders, to study the effects of the PRRT2 mutations on tissue development, for the screening of candidate pharmaceutical compounds, for the creation of explanted mammalian cell cultures which express the mutants, and for the evaluation of potential therapeutic interventions.

Animal species which are suitable for use in the animal models of the present invention include, but are not limited to, rats, mice, hamsters, guinea pigs, rabbits, dogs, cats, goats, sheep, pigs, and non-human primates such as monkeys and chimpanzees. For initial studies, genetically modified mice and rats are highly desirable due to the relative ease in generating knock-in, knock-out or transgenics of these animals, their ease of maintenance and their shorter life spans. For certain studies, transgenic yeast or invertebrates may be suitable and preferred because they allow for rapid screening and provide for much easier handling. For longer term studies, non-human primates may be desired due to their similarity with humans.

To create an animal model of a mutant PPRT2 gene of the present invention several methods can be employed. These include, but are not limited to, generation of a specific PPRT2 mutation in a homologous animal gene, insertion of a mutant human PRRT2 gene and/or a humanized animal PRRT2 gene by homologous recombination, insertion of a mutant human PPRT2 gene as genomic or minigene cDNA constructs using wild type, mutant or artificial promoter elements, or insertion of artificially modified fragments of the endogenous gene by homologous recombination. The modifications include insertion of mutant stop codons, the deletion of DNA sequences, or the inclusion of recombination elements (lox p sites) recognized by enzymes such as Cre recombinase.

To create transgenic mice in order to study gain of gene function in vivo, any mutant of the invention can be inserted into a mouse germ line using standard techniques such as oocyte microinjection. Gain of gene function can mean the over-expression of a gene and its protein product, or the genetic complementation of a mutation of the gene under investigation. For oocyte injection, one or more copies of the mutant gene can be inserted into the pronucleus of a just-fertilized mouse oocyte. This oocyte is then reimplanted into a pseudo-pregnant foster mother. The live-born mice can then be screened for integrants using analysis of tail DNA for the presence of the relevant human gene sequence. The transgene can be either a complete genomic sequence injected as a YAC, BAC, PAC or other chromosome DNA fragment, a cDNA with either the natural promoter or a heterologous promoter, or a minigene containing the whole coding region and other elements found to be necessary for optimum expression.

To generate knock-out mice or knock-in mice, gene targeting through homologous recombination in mouse embryonic stem (ES) cells may be applied. Knock-out mice are generated to study loss of gene function in vivo (for example to study the effects of the truncating mutations) while knock-in mice allow the study of gain of function or to study the effect of specific gene mutations. Knock-in mice are similar to transgenic mice however the integration site and copy number are defined in the former.

For knock-out mouse generation, gene targeting vectors can be designed such that they disrupt (knock-out) the protein coding sequence of the PRRT2 gene in the mouse genome. This disruption is typically mediated by homologous recombination (Joyner, 2000, *Gene Targeting: A Practical Approach*, Oxford University Press) in murine embryonic stem cells or can be mediated by other technologies such as siRNA vectors that target the relevant gene (Kunath et al., 2003, *Nature Biotechnol.* 21: 559-561). Knock-out animals will comprise a functional disruption of the PRRT2 gene such that the gene does not express a biologically active product. It can be substantially deficient in at least one functional activity coded for by the gene. Expression of the polypeptide encoded by the gene can be substantially absent (i.e. essentially undetectable amounts are made) or may be deficient in activity such as where only a portion of the gene product is produced. In contrast, knock-in mice can be produced whereby a gene targeting vector containing the mutant PRRT2 gene can integrate into a defined genetic locus in the mouse genome. For both applications, homologous recombination is catalysed by specific DNA repair enzymes that recognise homologous DNA sequences and exchange them via double crossover.

Gene targeting vectors are usually introduced into ES cells using electroporation. ES cell integrants are then isolated via an antibiotic resistance gene present on the targeting vector and are subsequently genotyped to identify those ES cell clones in which the gene under investigation has integrated into the locus of interest. The appropriate ES cells are then transmitted through the germline to produce a novel mouse strain.

In instances where gene ablation results in early embryonic lethality, conditional gene targeting may be employed. This allows genes to be deleted in a temporally and spatially controlled fashion. As above, appropriate ES cells are transmitted through the germline to produce a novel mouse strain, however the actual deletion of the gene is performed in the adult mouse in a tissue specific or time controlled manner. Conditional gene targeting is most commonly achieved by use of the cre/lox system. The enzyme ore is able to recognise the 34 base pair loxP sequence such that loxP flanked (or floxed) DNA is recognised and excised by ore. Tissue specific cre expression in transgenic mice enables the generation of tissue specific knock-out mice by mating gene targeted fleoxed mice with cre transgenic mice. Knock-out can be conducted in every tissue (Schwenk et al., 1995, *Nucleic Acids Res.* 23: 5080-5081) using the "delete" mouse or using transgenic mice with an inducible cre gene (such as those with tetracycline inducible cre genes), or knock-out can be tissue specific for example through the use of the CD19-cre mouse (Rickert et al., 1997, *Nucleic Acids Res.* 25: 1317-1318).

Once knock-in animals have been produced they can subsequently be used to study the extent and mechanisms of disease, and can be used for testing the effects that a change in genetic background has on the phenotype of the animal. This can be achieved in mice for instance by crossing a knock-in mouse of the invention with a mouse comprising a different genetic background, for example that of the DBA/2J, C3H/HeJ or Frings strains.

Using methods well known in the art, a mutant PRRT2 polypeptide of the present invention may be used to produce antibodies specific for the mutant polypeptide or to screen libraries of pharmaceutical agents to identify those that bind the mutant polypeptide. Furthermore, an antibody which specifically binds to a mutant PRRT2 polypeptide of the invention may be used directly as an antagonist or modulator, or indirectly as a targeting or delivery mechanism for bringing a pharmaceutical agent to cells or tissues that express the mutant polypeptide.

Accordingly, in an eighth aspect the present invention provides an antibody or fragment thereof which specifically binds to a polypeptide according to a fifth or sixth aspect of the invention.

Furthermore, in a ninth aspect, the present invention provides an antibody or fragment thereof which detects a polypeptide according to a fifth or sixth aspect of the invention, wherein said polypeptide comprises a truncation mutation, and wherein said antibody or fragment thereof binds to the truncated region of said polypeptide.

Such antibodies contemplated by this aspect of the invention may include, but are not limited to, polyclonal, monoclonal, chimeric, and single chain antibodies as would be understood by the person skilled in the art. For the production of antibodies, various hosts including rabbits, rats, goats, mice, humans, and others may be immunized by injection with a mutant polypeptide as described or with any fragment or oligopeptide thereof which has immunogenic properties. Various adjuvants may be used to increase immunological response and include, but are not limited to, Freund's, mineral gels such as aluminum hydroxide, and surface-active substances such as lysolecithin. Adjuvants used in humans include BCG (bacilli Calmette-Guerin) and *Corynebacterium parvum*.

It is preferred that the PRRT2 oligopeptides, peptides, or fragments used to induce antibodies to the mutant PRRT2 polypeptides of the invention have an amino acid sequence consisting of at least 5 amino acids, and, more preferably, of at least 10 amino acids. It is also preferable that these oligopeptides, peptides, or fragments are identical to a portion of the amino acid sequence of the natural protein and contain the entire amino acid sequence of a small, naturally occurring molecule. Short stretches of amino acids from polypeptides of the present invention may be fused with those of another protein, such as KLH, and antibodies to the chimeric molecule may be produced.

Monoclonal antibodies to a mutant PRRT2 polypeptide of the invention may be prepared using any technique which provides for the production of antibody molecules by continuous cell lines in culture. These include, but are not limited to, the hybridoma technique, the human B-cell hybridoma technique, and the EBV-hybridoma technique (for example, see Kohler et al., 1975, *Nature* 256: 495-497; Kozbor et al., 1985, *J. Immunol. Methods* 81:31-42; Cote et al., 1983, *Proc. Natl. Acad. Sci. USA* 80: 2026-2030; and Cole et al., 1984, *Mol. Cell Biochem.* 62: 109-120).

Antibodies may also be produced by inducing in vivo production in the lymphocyte population or by screening immunoglobulin libraries or panels of highly specific binding reagents as disclosed in the literature (for example, see Odlandi et al., 1989, *Proc. Natl. Acad. Sci. USA* 86: 3833-3837; and Winter and Milstein, 1991, *Nature* 349: 293-299).

Antibody fragments which contain specific binding sites for a mutant PRRT2 polypeptide of the invention may also be generated. For example, such fragments include, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (for example, see Huse et al., 1989, *Science* 246: 1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between a protein and its specific antibody. A two-site, monoclonal-based immunoassay utilizing antibodies reactive to two non-interfering epitopes is preferred, but a competitive binding assay may also be employed.

Having established a link between the PRRT2 gene and seizure and movement disorders, the present invention enables therapeutic applications for such disorders. For example, a mutant PRRT2 polypeptide, including a PRRT2 polypeptide mutant identified by the inventors, may be used to produce antibodies specific for the mutant polypeptide (as described above) or to screen libraries of pharmaceutical agents to identify those that bind the mutant polypeptide (see below).

In one embodiment, an antibody, which specifically binds to a mutant of the invention, may be used directly as an antagonist or modulator, or indirectly as a targeting or delivery mechanism for bringing a pharmaceutical agent to cells or tissues that express the mutant polypeptide.

The identification of PRRT2 as a gene involved in seizure and/or movement disorders enables methods for treating such disorders, including BFIE or ICCA. Restoration of functional PRRT2 gene expression or functional PRRT2 polypeptide may be of therapeutic benefit. Accordingly, a further aspect of the present invention relates to restoring functional PRRT2 gene and/or protein expression and/or activity. Numerous methods exist for restoring gene and protein expression and activity. For example, a vector expressing the wild-type PRRT2 nucleic acid may be administered to a subject in need of such treatment. Many methods for introducing vectors into cells or tissues are available each equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art.

A further aspect of the invention relates to treating a seizure and/or movement disorder, including BFIE or ICCA, by silencing of the mutant PRRT2 gene in an affected subject. One approach comprises administering a DNA molecule which is the complement (antisense) of a mutant PRRT2 nucleic acid, including a complement of any one of the PRRT2 nucleic acid mutants identified by the inventors, and which is, or encodes for, an RNA molecule that hybridizes with mRNA encoded by the mutant PRRT2, to a subject in need of such treatment.

Typically, a vector expressing the complement (antisense) of the mutant PRRT2 nucleic acid may be administered to a subject in need of such treatment. Methods for introducing vectors into cells or tissues are described above.

Additional antisense or gene-targeted silencing strategies may include, but are not limited to, the use of antisense oligonucleotides, injection of antisense RNA, transfection of antisense RNA expression vectors, and the use of RNA interference (RNAi) or short interfering RNAs (siRNA). Still further, catalytic nucleic acid molecules such as DNAzymes and ribozymes may be used for gene silencing. These molecules function by cleaving their target mRNA molecule rather than merely binding to it as in traditional antisense approaches.

According to still another aspect of the invention, a mutant PRRT2 nucleic acid or polypeptide, including the specific PRRT2 nucleic acid and polypeptide mutations identified by the inventors, as well as cells expressing these, are useful for the screening of candidate pharmaceutical agents, particularly those for the treatment of seizure or movement disorders such as BFIE and ICCA.

Agents that can be screened in accordance with the invention include, but are not limited to, peptides (such as soluble peptides), phosphopeptides and small organic or inorganic molecules (such as natural product or synthetic chemical libraries and peptidomimetics).

In one embodiment, a screening assay may include a cell-based assay utilising eukaryotic or prokaryotic host cells that are stably transformed with recombinant molecules expressing mutant PRRT2 polypeptide, in competitive binding assays. Binding assays (e.g. ELISA-based or competition-based assays) will measure the formation of complexes between a specific mutant PRRT2 polypeptide, and the agent being tested, or will measure the degree to which an agent being tested will inhibit or restore the formation of a complex between a specific mutant PRRT2 polypeptide, and its interactor or ligand. A change in activity may be observed in these assays by using standard methods including spectrophotometric, fluorimetric, calorimetric or chemi-luminescent means preferably providing for the automation or partial automation of the detecting step (e.g. by a microplate reader or use of a flow cytometer).

Non cell-based assays may also be used for identifying agents that can inhibit or restore binding between a mutant PRRT2 polypeptide, including those mutants identified by the inventors, and their interactors. Such assays are known in the art and include for example AlphaScreen technology (PerkinElmer Life Sciences, MA, USA). This application relies on the use of beads such that each interaction partner is bound to a separate bead via an antibody. Interaction of each partner will bring the beads into proximity, such that laser excitation initiates a number of chemical reactions ultimately leading to fluorophores emitting a light signal. Candidate agents that inhibit the binding of the mutant with its interactor will result in loss of light emission, while candidate agents that restore the binding of the mutant with its interactor will result in positive light emission. These assays ultimately enable identification and isolation of the candidate agents.

High-throughput drug screening techniques may also employ methods as described in WO84/03564 and Pirogova et al., 2011 (*Curr. Pharm. Biotechnol.* 12: 1117-1127), amongst others. For example, efficient technologies such as combinatorial chemistry, high throughput screening (HTS), virtual screening, de novo design and structure-based drug design are relevant to the present invention as they may provide an efficient means for identifying candidate therapeutics. As a more specific example, small peptide test agents synthesised on a solid substrate can be assayed for mutant polypeptide binding. Bound mutant PRRT2 polypeptide is then detected by methods well known in the art. In a variation of this technique, purified mutant PRRT2 polypeptides can be coated directly onto plates to identify interacting test agents.

The invention also contemplates the use of competition drug screening assays in which neutralizing antibodies capable of specifically binding a mutant PRRT2 polypeptide compete with a test agent for binding thereto. In this manner, the antibodies can be used to detect the presence of any peptide that shares one or more antigenic determinants of the mutant.

A mutant PRRT2 polypeptide, including those mutants identified by the inventors, may also be used for screening agents developed as a result of combinatorial library technology. This provides a way to test a large number of different substances for their ability to modulate activity of a polypeptide. An agent identified as a modulator of polypeptide function may be peptide or non-peptide in nature. Non-peptide "small molecules" are often preferred for many in vivo pharmaceutical applications. In addition, a mimic or mimetic of the substance may be designed for pharmaceutical use. The design of mimetics based on a known pharmaceutically active compound ("lead" compound) is a common approach to the development of novel pharmaceuticals. This is often desirable where the original active agent is difficult or expensive to synthesise or where it provides an unsuitable method of administration. In the design of a mimetic, particular parts of the original active agent that are important in determining the target property are identified. These parts or residues constituting the active region of the agent are known as its pharmacophore. Once found, the pharmacophore structure is modelled according to its physical properties using data from a range of sources including x-ray diffraction data and NMR. A template molecule is then selected onto which chemical groups which mimic the pharmacophore can be added. The selection can be made such that the mimetic is easy to synthesise, is likely to be pharmacologically acceptable, does not degrade in vivo and retains the biological activity of the lead compound. Further optimisation or modification can be carried out to select one or more final mimetics useful for in vivo or clinical testing.

Another alternative method for drug screening relies on structure-based rational drug design. Determination of the three dimensional structure of a mutant PRRT2 polypeptide, including those mutants identified by the inventors, allows for structure-based drug design to identify biologically active lead compounds.

Three dimensional structural models can be generated by a number of applications, some of which include experimental models such as x-ray crystallography and NMR and/or from in silico studies of structural databases such as the Protein Databank (PDB). In addition, three dimensional structural models can be determined using a number of known protein structure prediction techniques based on the primary sequences of the polypeptides (e.g. SYBYL—Tripos Associated, St. Louis, Mo.), de novo protein structure design programs (e.g. MODELER—MSI Inc., San Diego, Calif., or MOE—Chemical Computing Group, Montreal, Canada) or ab initio methods (e.g. see U.S. Pat. Nos. 5,331,573 and 5,579,250).

Once the three dimensional structure of a polypeptide has been determined, structure-based drug discovery techniques can be employed to design biologically-active agents based on these three dimensional structures. Such techniques are known in the art and include examples such as DOCK (University of California, San Francisco) or AUTODOCK (Scripps Research Institute, La Jolla, Calif.). A computational docking protocol will identify the active site or sites that are deemed important for protein activity based on a predicted protein model. Molecular databases, such as the Available Chemicals Directory (ACD) are then screened for molecules that complement the protein model.

Using methods such as these, potential clinical drug candidates can be identified and computationally ranked in order to reduce the time and expense associated with typical "wet lab" drug screening methodologies. The control response for the above referenced screening methodologies may include a baseline response detected in said cell or animal without exposure to the test agent or, alternatively, the control response may be a response following exposure to the test agent in cells or animals comprising a normal or wild-type complete PRRT2 coding sequence. The test agents or drug candidates may be selected from known and novel compounds, complexes and other substances which may, for example, be sourced from private or publicly accessible agent libraries (e.g. the Queensland Compound Library (Griffith University, Nathan, OLD, Australia) and the Molecular Libraries Small Molecule Repository (NIH Molecular Libraries, Bethesda, Md., USA). The test agent may therefore comprise a protein, polypeptide or peptide (e.g. a recombinantly expressed PRRT2 gene, protein or polypeptide, or a functional fragment or functional variant thereof), or a mimetic thereof (including so-called synthetic nucleic acid mimics, peptoids and retro-inverso peptides), but more preferably comprises a small organic molecule and especially one which complies or substantially complies with Lipinski's Rule of Five for "druglikeness" (Lipinski, C A at al., 2001, *Adv. Drug. Del. Rev.* 46: 3-26). The test agent may also be selected on the basis of structural analysis of known or novel compounds or may otherwise be designed following the further structural analysis of PRRT2 binding sites.

Agents identified through screening procedures as described above, and which are based on the use of a mutant PRRT2 nucleic acid molecule or polypeptide, including those mutants identified by the inventors, form a part of the present invention, as do pharmaceutical compositions containing these and a pharmaceutically acceptable carrier.

The present invention also provides a kit that can be used to perform the methods of the first or second aspects of the invention. For example, the kit may contain, in an amount sufficient for at least one assay, hybridization assay probes, amplification primers, and/or antibodies, which are specific for wild-type and mutant PRRT2 nucleic acids or PRRT2 polypeptides. These components have been described in detail above. Typically, the kit will also include instructions recorded in a tangible form (e.g. contained on paper or an electronic medium) for using the packaged probes, primers, and/or antibodies in a detection assay for determining the presence of a mutant PRRT2 nucleic acid or mutant PRRT2 polypeptide in a test sample.

Accordingly, in a tenth aspect, the present invention provides a kit for diagnosing or prognosing a seizure and/or movement disorder in a subject, or for identifying a subject with an increased likelihood of having an offspring predisposed to a seizure and/or movement disorder, said kit including one or more components for testing for the presence of an alteration in the PRRT2 gene in the subject.

In one embodiment, the one or more components are selected from the group consisting of: (i) an antibody or fragment thereof which specifically binds to a polypeptide according to a fifth or sixth aspect of the invention; (ii) an antibody or fragment thereof which detects a polypeptide according to a fifth or sixth aspect of the invention, wherein said polypeptide comprises a truncating mutation, and wherein said antibody or fragment thereof binds to the truncated region of said polypeptide; and (iii) a nucleic acid molecule which specifically hybridises to a nucleic acid molecule according to a third or fourth aspect of the invention.

The various components of the kit may be provided in a variety of forms. For example, the required enzymes, the nucleotide triphosphates, the probes, primers, and/or antibodies may be provided as a lyophilized reagent. These lyophilized reagents may be pre-mixed before lyophilization so that when reconstituted they form a complete mixture with the proper ratio of each of the components ready for use in the assay. In addition, the kit may contain a reconstitution reagent for reconstituting the lyophilized reagents of the kit.

In one example, the kit may comprise at least three lyophilized oligonucleotides, including a primer pair to PCR amplify a portion of PRRT2 nucleic acid, and a detectably labeled probe capable of hybridizing to the generated amplicon. In some kits, at least three lyophilized oligonucleotides are the primers for amplification of at least a portion of PRRT2 nucleic acid by semi-nested PCR.

Some kits may further comprise a solid support for anchoring the nucleic acid of interest on the solid support. The target nucleic acid may be anchored to the solid support directly or indirectly through a capture probe anchored to the solid support and capable of hybridizing to the nucleic acid of interest. Examples of such solid supports include, but are not limited to, beads, microparticles (for example, gold and other nano particles), microarray, microwells, and multiwell plates. The solid surface may comprise a first member of a binding pair and the capture probe or the target nucleic acid may comprise a second member of the binding pair. Binding of the binding pair members will anchor the capture probe or the target nucleic acid to the solid surface. Examples of such binding pairs include but are not limited to biotin/streptavidin, hormone/receptor, ligand/receptor, and antigen/antibody.

In other kits, lyophilized antibodies against PRRT2 wild-type and mutant polypeptide may be provided. In some kits a primary/secondary antibody pair may be provided. Some kits may further comprise a solid support for anchoring the PRRT2 wild-type and mutant polypeptides. Such anchoring of the PRRT2 wild-type and mutant polypeptides may be through biotin/streptavidin and antigen/antibody interactions as described above.

Typical packaging materials may include solid matrices such as glass, plastic, paper, foil, micro-particles and the like, capable of holding within fixed limits hybridization assay probes, and/or amplification primers. Thus, for example, the packaging materials can include glass vials used to contain sub-milligram (e.g. picogram or nanogram) quantities of a contemplated probe, primer, or antibody, or they can be microtiter plate wells to which probes, primers, or antibodies have been operatively affixed, i.e. linked so as to be capable of participating in an amplification and/or detection methods.

The kit may include instructions indicating the reagents and/or concentrations of reagents and at least one assay method parameter which might be, for example, the relative amounts of reagents to use per amount of sample. In addition, such specifics as maintenance, time periods, temperature, and buffer conditions may also be included.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

It is to be noted that where a range of values is expressed, it will be clearly understood that this range encompasses the upper and lower limits of the range, and all values in between these limits.

Furthermore, the term "about" as used in the specification means approximately or nearly and in the context of a numerical value or range set forth herein is meant to encompass variations of +/−10% or less, +/−5% or less, +/−1% or less, or +/−0.1% or less of and from the numerical value or range recited or claimed.

It will be apparent to the person skilled in the art that while the invention has been described in some detail for the purposes of clarity and understanding, various modifications and alterations to the embodiments and methods described herein may be made without departing from the scope of the inventive concept disclosed in this specification.

The invention is further illustrated in the following examples. The examples are for the purpose of describing particular embodiments only and are not intended to be limiting with respect to the above description.

Example 1

Identification of a Causative Gene for Seizure and Movement Disorders

The following study was conducted to identify genes causative for seizure and movement disorders. Families (and subjects therein) with epilepsy (benign familial infantile epilepsy) and/or a seizure disorder (ICCA) formed the basis of the study.

Patients and Controls

The study was approved by the Human Research Ethics Committees of Austin Health and the Women's and Children's Hospital. Individuals underwent detailed phenotyping using a validated seizure questionnaire. All previous medical records, EEG and neuroimaging data were obtained where available. Australian control samples were anonymous blood donors. Israeli control samples were unaffected, unrelated members of families recruited for studies into the genetic causes of epilepsy.

Genotyping

Microsatellite markers in regions linked to BFIE were genotyped either by electrophoresis on denaturing polyacrylamide gels followed by autoradiography, by denaturing gel electrophoresis using the GelScan 3000 (Corbett Research, Sydney, Australia) or by capillary electrophoresis using the ABI 3100 Avant DNA analyser with Genescan 400D ROX labelled size standards (Applied Biosystems, Carlsbad, Calif.). For the latter two methods, the forward primer of each pair was labelled with either HEX or FAM. Primer sequences for microsatellite markers were from UniSTS. LOD scores were calculated using the FASTLINK program.

Linkage

Linkage analysis was performed for families 1-9, 11 and 12 with BFIE or ICCA (FIG. 1). This analysis yielded maximum LOD scores for the chromosome 16 locus of 3.27, 3.0 and 2.71 for Families 1, 2 and 5 respectively. Families 3, 4, 6-9, 11 and 12 were consistent with linkage to chromosome 16. Linkage to the chromosome 1 locus was excluded for Families 1, 3, 5-7, 9 and 11. Linkage to the chromosome 19 locus was excluded for Families 1, 3 and 6-9 and 11. Linkage to SCN2A, the gene for the overlapping syndrome of benign familial neonatal-infantile seizures was excluded for families 1, 6-9 and 11-13. This is consistent with the causative gene in these families residing in the chromosome 16p11.2-q12.1 BFIE region.

Identification of Genes in the Chromosome 16 Linkage Interval

A sequence capture array was designed to capture coding sequences, minimal promoter sequences and microRNAs in the chromosome 16 linkage interval, which is between D16S3093 and D16S411. Sequence capture and amplification of captured sequences was performed by Roche-Nimblegen (Madison, Wis.). Massively parallel sequencing (MPS) of captured and amplified DNA was performed by GeneWorks (Adelaide, Australia) using the Illumina Genome Analyzer II. Sequences were mapped to a repeat masked version of the human genome (UCSC genome browser, hg18) using Mosaik 1.0.1388. All variants to a sequence depth greater than or equal to 10 reads and between 15 to 85% discordant with the reference sequence were identified using Consed v19. Variants were functionally annotated using SeattleSeq.

Massively parallel sequencing (MPS) was performed for one individual from each of families 1 and 5, which showed linkage to the chromosome 16 BFIE region. This sequencing identified unique variants in the brain-expressed genes A2LP, ARMC5 and BCKDK in the individual from Family 5. The variants in ARMC5 and BCKDK segregated with the phenotype in the family and these genes were screened by Sanger sequencing in a further ten patients from BFIE families consistent with linkage to chromosome 16. Only one additional unique coding variant was identified, and it was therefore concluded that neither of these genes was the causative gene for BFIE. Since MPS failed to identify the pathogenic mutation using the criteria specified, analyses shifted to sequences predicted as difficult to capture and sequence using this technology. Portions of PRRT2 fall into this category.

Sequencing and Screening of PRRT2 Variants

Probands from 23 families with BFIE or ICCA were sequenced for the coding regions of PRRT2 (NM_145239.2) by direct Sanger sequencing. Mutations were identified in 19 of the 23 families (83%). The mutations comprised two frameshifts (c.629-630insC, p.P210fsX15 and c.649-650insC, p.R217fsX8) and two splice site mutations (IVS2+1G>T, IVS2+5G>A) which are each predicted to cause protein truncation (FIG. 2). The fifth mutation was a missense mutation c.950G>A, p.S317N, which alters an amino acid residue in a PRRT2 transmembrane domain which has been evolutionarily conserved from zebrafish to humans, with the PRRT2 protein only found in vertebrates. Pathogenicity of this missense mutation is supported by the p.S317N substitution being predicted to be probably damaging by PolyPhen-2, and not tolerated by the SIFT (Sorting Tolerant from Intolerant) algorithm (http://sift.jcvi.org/).

Family members and controls were analysed for the c.629-630insC and the c.649-650insC mutations by direct sequencing. Controls and family members for the IVS2+1 and IVS2+5 mutations were screened by High-Resolution Melting (HRM) analysis using the LightScanner® (Idaho Technology, Salt Lake City, Utah). Controls for the c.950G>A mutation were screened by LightScanner and family members were Sanger sequenced. The PRRT2 mutations segregated with the BFIE or ICCA (BFIE and PKC) phenotype in each of the 19 families (FIG. 1, Table 2) and were not present in 92 controls or in dbSNP. The primer sequences and PCR conditions used for Sanger sequencing and screening are available on request.

TABLE 2

Clinical and Genetic Details of Families with PRRT2 Mutations

| Family number | No. with BFIE or ICCA | Mean age of seizure onset (range) [data on n] | Range of age of seizure offset [data on n] | Phenotype | Ethnic origin | Mutation |
|---|---|---|---|---|---|---|
| 1 | 9 | 9 m (7.5-11 m) [3] | N/A | BFIE | Israeli, Ashkenazi Jewish | IVS2 + 5G > A |
| 2 | 17 | 6.7 m (3-12 m) [7] | 12 m-25 m [7] | ICCA | Scottish | c.629-630insC (p.P210fsX224) |
| 3 | 3 | 6 m (5-8 m) [3] | 6 m-2 y [3] | BFIE | Israeli, Sephardi Jewish | IVS2 + 1G > T |
| 4 | 12 | 4.4 m (3-6 m) [8] | 5 m-2 y | BFIE | Australasian/ Western European | c.950G > A (p.S317N) |

TABLE 2-continued

Clinical and Genetic Details of Families with PRRT2 Mutations

| Family number | No. with BFIE or ICCA | Mean age of seizure onset (range) [data on n] | Range of age of seizure offset [data on n] | Phenotype | Ethnic origin | Mutation |
|---|---|---|---|---|---|---|
| 5 | 9 | 5.2 m (3.5-7 m) [9] | 5 m-14 m [9] | ICCA | Australasian/ Western European | c.649-650insC (p.R217fsX224)* |
| 6 | 7 | 6.4 m (5-11 m) [6] | 5-12 m [6] | BFIE | Australasian/ Western European | c.649-650insC (p.R217fsX224)* |
| 7 | 6 | 8.2 m (5-10 m) [5] | 10 m-23 m [5] | BFIE | Australasian/ Western European | c.649-650insC (p.R217fsX224)* |
| 8 | 6 | 9.5 m (8-13 m) [4] | 10 m-3 y [4] | BFIE | Australasian/ Western European | c.649-650insC (p.R217fsX224)* |
| 9 | 7 | 6.5 m (5-8 m) [6] | 6 m-2 y [5] | BFIE | Israeli, Sephardi Jewish | c.649-650insC (p.R217fsX224)* |
| 10 | 4 | 6.8 m (6-8 m) | <2.5 y | BFIE | Israeli, Sephardi Jewish | c.649-650insC (p.R217fsX224)* |
| 11 | 3 | 4.3 m (3-6 m) [3] | 3 m-2 y [3] | BFIE | Australasian/ Western European | c.649-650insC (p.R217fsX224)* |
| 12 | 4 | 4.5 m (4-5 m) [2] | 5 m-<1 y [2] | BFIE | Australasian/ Western European | c.649-650insC (p.R217fsX224)* |
| 13 | 3 | 4 m (4 m) [3] | 6 m-16 m [3] | BFIE | Swedish | c.649-650insC (P.R217fsX224)* |
| 14 | 3 | 4.3 m (4-5 m) [3] | 5 m-24 m [3] | BFIE | Australasian/ Western European | c.649-650insC (p.R217fsX224)* |
| 15 | 2 | 3.3 m (3-3.5 m) [2] | 4 m [2] | BFIE | Australasian/ Western European | c.649-650insC (p.R217fsX224)* |
| 16 | 2 | 10.7 m (5-18 m) [3] | 7 m-33 m [3] | BFIE | Australasian/ Western European | c.649-650insC (p.R217fsX224)* |
| 17 | 9 | 6.3 m (4-8 m) [4] | 5 m-8 m [4] | BFIE | Australasian/ Western European | c.649-650insC (p.R217fsX224)* |
| 18 | 3 | 6 m [1] | | ICCA | Australasian/ Western European | c.649-650insC (p.R217fsX224)* |
| 19 | 3 | 5.5 m (5-6 m) [2] | 6 m [2] | BFIE | Australasian/ Western European | c.649-650insC (p.R217fsX224)* |

Abbreviations:
m = months,
BFIE = benign familial infantile epilepsy,
ICCA = infantile convulsions and paroxysmal choreocathetosis,
N/A = not available.

In 19 families segregating a PRRT2 mutation, there were a total of 77 individuals affected with BFIE or ICCA with a mutation. In addition, there were 23 apparently unaffected mutation carriers (FIG. 1). However, an accurate clinical history regarding the occurrence of infantile seizures could not always be obtained for older family members, making the precise level of penetrance of the mutations difficult to determine. Only one individual (4-III-1) with infantile seizures lacked the familial PRRT2 mutation and was therefore considered a phenocopy. We also observed two non-synonymous PRRT2 sequence variants in controls: c.647C>T, P216L (rs76335820) in 6/115 (5.2%) Australian controls and one patient and c.644C>G, P215R in 1/97 (1%) Sephardic Jewish controls. As described above, sequence capture and massively parallel sequencing of the chromosome 16 linkage interval did not identify any other potentially deleterious mutations in Families 1 and 5.

Our results demonstrate that mutations in PRRT2 cause BFIE. We have also shown that the two distinct disorders, BFIE and ICCA, are allelic: that is, caused by mutations in the same gene. Detection of PRRT2 mutations in 14/17 (82%) of BFIE and 5/6 (83%) of ICCA families indicates that mutations in this gene are the most common cause of these distinctive epilepsy syndromes. Fifteen of the 19 mutation-positive families (79%) carry the same mutation, c.649-650insC, which is seen in 12 BFIE and 3 ICCA families. It is most likely that this mutation arose independently in at least some of the families given their diverse ethnic origins: Australasian/Western European (12), Swedish (1) and Sephardic Jewish Israeli (2). Furthermore, genotyping of three microsatellite markers closely linked to PRRT2 in families 5-8 (Australian) and 10 and 11 (Sephardic Jewish) did not show any common haplotypes.

With respect to the c.649-650insC mutation, this frameshift mutation is likely to be due to the sequence context in which it occurs. The insertion of a cytosine base occurs in a homopolymer of nine cytosine (C) bases adjacent to four guanines (G). This DNA sequence has the potential to form a hairpin-loop structure, possibly leading to DNA polymerase slippage and the insertion of an extra cytosine during DNA replication. Interestingly, one of the two substitution polymorphisms, c.647C>T, P216L, seen in this sequence was present in a higher percentage of controls than patients. Alleles carrying this polymorphism are potentially protected against the insertion mutation as the polymorphism alters the polycytosine tract, reducing its size from nine to six base pairs.

The mutations in Families 1 and 5 were not detected by massively parallel sequencing, despite coverage of PRRT2 on the capture array used for enrichment of sequences from the chromosome 16 BFIE region. The percentage of reads containing the common insertion mutation in Family 5 was below the threshold set for mutation calling. Also, the reads for the homopolymer tract showed a variable number of cytosines. This illustrates that MPS is not always a robust method of mutation detection, especially in "difficult" sequences such as homopolymer tracts or G/C rich regions.

The finding of PRRT2 mutations in BFIE reveals that the PRRT2 protein has a role in epilepsy. Three different mutations were detected in families with ICCA, so this syndrome is not only due to the common insertion mutation. It remains unclear why one individual should experience either BFIE or PKC or both of these phenotypes within a family—the pleiotropy is remarkable in terms of age of onset and anatomical substrate. Genetic background or the influence of the second PRRT2 allele modifying the phenotypic expression of a single mutation are possible explanations: the mechanisms underlying such variable expressivity are yet to be understood. Recently, a homozygous frameshift mutation of PRRT2 in a consanguineous Iranian family has been reported in an individual with intellectual disability (ID). Phenotypic heterogeneity is not uncommon for genes involved in epilepsy but is more unusual when considering epilepsy and movement disorders which engage different neuronal networks. We speculate that epilepsy and cognitive impairment may result from early expression of PRRT2 in brain regions associated with seizures and later expression in regions associated with movement.

The occurrence of either infantile seizures or PKC but not both disorders in some individuals with PRRT2 mutations may be due to incomplete penetrance of the mutation at one of the developmental stages at which the phenotype manifests. The genetic overlap of epilepsy and movement disorders has recently been recognised in glucose transporter 1 deficiency syndrome in which both paroxysmal exercise-induced dyskinesla and epilepsy co-occur in families and in individuals. The identification of PRRT2significantly extends our current knowledge of the molecular basis for early childhood epilepsies and continues to expand the importance of the role of non-ion channel genes in the pathogenesis of epilepsy. This finding also helps to complete an unambiguous molecular based classification framework to direct diagnosis, treatment and prognosis.

Example 2

Further Mutation Screening of the PRRT2 Gene

Figure 4:
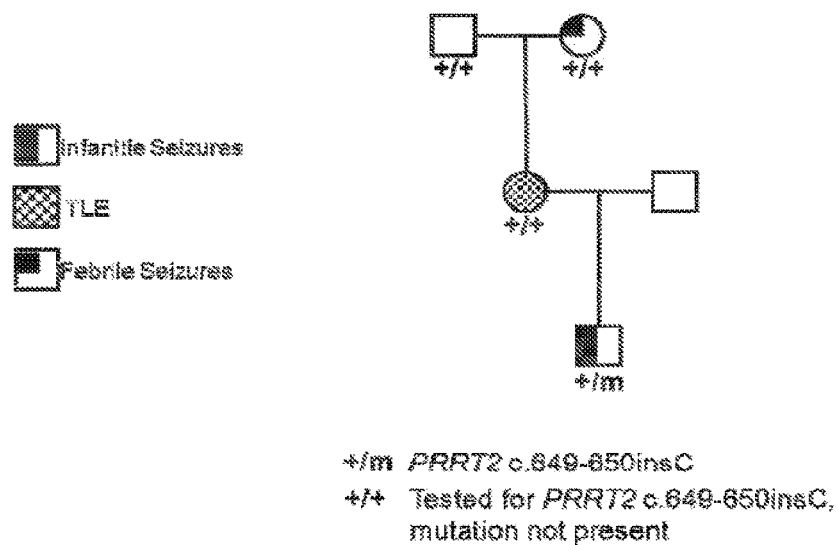
FIG. 4—A-K: Pedigrees of a further 11 families with BFIE, ICCA or sporadic infantile seizures as examined in Example 2, showing the segregation of the PRRT2 mutation within each family. Individuals with a mutation in PRRT2 are indicated by +/m and individuals tested for mutations and found to be negative are indicated by +/+.

Using the same mutation detection techniques as described in Example 1, additional subjects and families were screened for mutations in the PRRT2 gene. The screen included 10 sporadic infantile seizures cases, 5 ICCA families, 7 BFIE families, 5 PKC families and 3 with phenotypes not given. Pedigrees for 11 of the 12 families are shown in FIG. 4.

The mutation screening established that subjects in 5 of the 7 BFIE families, and all five of the ICCA families had mutations in the PRRT2 gene. All had the c.649-650insC mutation.

Collectively, the mutation screening performed to date has identified five mutations in the PRRT2 gene in individuals with seizure and movement disorders. The most common mutation was the c.649-650insC mutation giving rise to a truncated PRRT2 polypeptide (p.R217fsX224). This mutation was identified in 86% of subjects carrying a mutation in the gene, and therefore represents a mutation which can form the basis of a routine screening assay for diagnosing or prognosing seizure or movement disorders in subjects, or for identifying carriers for the mutation.

Example 3

Diagnostic Assays for Identifying Individuals with Seizure or Movement Disorders As indicated above, screening for the presence of the most common PRRT2 gene mutation (c.649-650insC) may form the basis of an assay for diagnosing seizure disorders such as epilepsy, or movement disorders such as PKD, in an individual. In one example, the PRRT2 c.649-650insC mutation can be screened for by PCR amplification using the oligonucleotide primers 5'-TCACTCACCACCCTCAAA-3' (SEQ ID NO: 12) and 5'-CATTCGATCCTCCTCAAC-3' (SEQ ID NO: 13), where one of the primers carries a fluorescent label such as HEX, followed by capillary electrophoresis using an ABI genetic analyser or similar. PCR amplification will produce an 85 base pair product in individuals that do not carry the c.649-650insC mutation. The sequence of the 85 base pair product is shown below and is represented by SEQ ID NO: 14.

```
5'-TCACTCACCACCCTCAAAAAAATCCCCCCCAGCCAATGGGGCC

CCCCCCCGAGTGCTGCAGCAGCTGGTTGAGGAGGATCGAATG-3'
```

Any insertion or deletion in this region of the PRRT2 gene will be seen as a change in PCR product length, as detected by routine procedures known in the art (such as capillary electrophoresis). Any change in PCR product length detected can be further investigated by sequencing the PCR product to identify the nature of the mutation.

Use of the PRRT2 gene in diagnostic assays to screen for individuals with seizure or movement disorders need not focus on the region of PRRT2 containing the c.649-650insC mutation. As shown in Example 1, four other mutations have been found in the PRRT2 gene by the present inventors, namely c.629-630insC, IVS2+1G>T, IVS2+5G>A, and c.950G>A. PCR-based assays as described above may also be utilised to specifically identify one or more of these mutations.

A further assay that may be employed for diagnostic purposes is the Multiplex Ligation-dependent Probe Amplification (MLPA) assay, as described in detail above. This assay may be used to detect deletions and partial duplications in a particular region of the PRRT2 gene, or across the whole PRRT2 gene. For example, the probes listed in Table 3 can be used in conjunction with a reference probe mix (MRC-Holland SALSA MLPA probemix P300-A2 Human DNA Reference-2) to detect large deletions and duplications affecting any region of PRRT2. Preparation of probe mixes and MLPA can be carried out according to the protocols provided in "Designing synthetic MLPA probes" and "Multiplex Ligation-dependent Probe Amplification (MLPAO) General Protocol" from MRC-Holland.

TABLE 3

Sequences of PRRT2 MLPA probes (5'-3')

| Exon | LPO | RPO - 5' phosphorylated | Probe length |
|---|---|---|---|
| 1 | GGGTTCCCTAAGGGTTGGATG GGATGAGCACACGGGAGAGGA GAAGAGGGA (SEQ ID NO: 15) | GACCCGCCGCCTCCCTCCCTCC CTAGCTGATCTAGATTGGATCTT GCTGGCAC (SEQ ID NO: 16) | 104 |
| 2-1 | GGGTTCCCTAAGGGTTGGATTC TATCTCCTCCTCTTCCAGGGTTT GCCGCTGTCT (SEQ ID NO: 17) | CTGCTATTCCATCCTCCCCATAG GGGCTCTCTCTTTCTAGATTGG ATCTTGCTGGCAC (SEQ ID NO 18) | 113 |
| 2-2 | GGGTTCCCTAAGGGTTGGATCT ACCCAGGAGGACCCCACCCCT GAGA (SEQ ID NO: 19) | TTCTGTCTGAGAGTGTAGGGGA AAAGCATTCTAGATTGGATCTTG CTGGCAC (SEQ ID NO: 20) | 99 |
| 2-3 | GGGTTCCCTAAGGGTTGGAGA CTACATCATCCTTGCCATCCTGT CCTGCTTCTGCCCCATGTGGCC TGTCAA (SEQ ID NO: 21) | CATCGTGGCCTTCGCTTATGCT GTCATGGTCTAGATTGGATCTT GCTGGCAC (SEQ ID NO: 22) | 124 |
| 3 | GGGTTCCCTAAGGGTTGGATAG CCAAGCTCTTAAGCATCGTGGC GCTGGTGGGGGAGTCCTCA (SEQ ID NO 23) | TCATCATCCCCTCCTGCGTCAT CAACTTAGTTCTAGATTGGATCT TGCTGGCAC (SEQ ID NO: 24) | 118 |
| 4 | GGGTTCCCTAAGGGTTGGAGA CCAAGGGAGCCTGAGCGGCCT TGTTTACAGCTTCTGTCCTGCTC CTGCAT (SEQ ID NO: 25) | CTTGCCAGGCTCCTCTGCCAAC TGTAGGCCTGCCTCATCTCTAG ATTGGATCTTGCTGGCAC (SEQ ID NO: 26) | 133 |

Gene-specific sequences are underlined and primer binding sequences are in bold.

Example 4

Functional Analysis of PRRT2 Mutations

To determine the effect that a particular PRRT2 mutation has on protein function, and ultimately cell function, a range of methods can be employed. One of those methods includes the production of a genetically modified animal, such as a genetically modified mouse, that harbours the particular PRRT2 mutation being analysed. Methods for the production of genetically modified animals are described in detail above.

Those skilled in the art will appreciate that the invention described herein is susceptible to variations and modifications other than those specifically described. It is to be understood that the invention includes all such variations and modifications. The invention also includes all of the steps, features, compositions and compounds referred to, or indicated in this specification, individually or collectively, and any and all combinations of any two or more of the steps or features.

---

The invention claimed is:

1. A nucleic acid probe comprising a sequence that is at least 96% identical to at least 20 contiguous nucleotides of SEQ ID NO: 1 and includes a C at position 630 of SEQ ID NO: 1, or the complement thereof;
   wherein the nucleic acid probe specifically and selectively hybridizes to a PRRT2 sequence comprising a frameshift mutation in exon 2 of the PRRT2 gene that is c.629-630 insC, or the complement thereof; and
   wherein the nucleic acid probe is labelled with a fluorescent moiety.

2. The nucleic acid probe of claim 1, wherein the nucleic acid probe is fixed to a solid support.

3. An array for detecting a mutation in a PRRT2 nucleic acid, comprising:
   a nucleic acid probe comprising a sequence that is at least 96% identical to at least 20 contiguous nucleotides of SEQ ID NO: 1 and includes a C at position 630 of SEQ ID NO: 1, or the complement thereof;
   wherein the nucleic acid probe specifically and selectively hybridizes to a PRRT2 sequence comprising a frameshift mutation in exon 2 of the PRRT2 gene that is c.629-630 insC, or the complement thereof; and
   wherein the nucleic acid probe is labelled with a fluorescent moiety.

4. The nucleic acid probe of claim 2, wherein the solid support is a bead, microparticle, microarray, microwell, or multiwell plate.

* * * * *